(12) United States Patent
Rieger et al.

(10) Patent No.: US 7,989,431 B2
(45) Date of Patent: *Aug. 2, 2011

(54) 2-PROPYNYL ADENOSINE ANALOGS WITH MODIFIED 5'-RIBOSE GROUPS HAVING A2A AGONIST ACTIVITY

(75) Inventors: Jayson M. Rieger, Charlottesville, VA (US); Joel M. Linden, Charlottesville, VA (US); Timothy L. Macdonald, Charlottesville, VA (US); Gail W. Sullivan, Charlottesville, VA (US); Lauren J. Murphree, Rockville, MD (US); Robert Alan Figler, Earlysville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/487,235

(22) Filed: Jun. 18, 2009

(65) Prior Publication Data

US 2009/0253647 A1 Oct. 8, 2009

Related U.S. Application Data

(63) Continuation of application No. 11/196,529, filed on Aug. 2, 2005, now Pat. No. 7,605,143.

(60) Provisional application No. 60/598,018, filed on Aug. 2, 2004.

(51) Int. Cl.
*A01N 43/04* (2006.01)
*A61K 31/70* (2006.01)

(52) U.S. Cl. .......................... 514/46; 514/45
(58) Field of Classification Search ................ None
See application file for complete search history.

(56) References Cited

U.S. PATENT DOCUMENTS

| | | |
|---|---|---|
| 3,892,777 A | 7/1975 | Gruenman et al. |
| 4,012,495 A | 3/1977 | Schmiechen et al. |
| 4,193,926 A | 3/1980 | Schmiechen et al. |
| 4,242,345 A | 12/1980 | Brenner et al. |
| 4,665,074 A | 5/1987 | Amschler |
| 4,824,660 A | 4/1989 | Angello et al. |
| 4,879,296 A | 11/1989 | Daluge et al. |
| 4,938,949 A | 7/1990 | Borch et al. |
| 4,956,345 A | 9/1990 | Miyasaka et al. |
| 4,965,271 A | 10/1990 | Mandell et al. |
| 4,968,697 A | 11/1990 | Hutchison |
| 5,070,877 A | 12/1991 | Mohiuddin et al. |
| 5,096,906 A | 3/1992 | Mandell et al. |
| 5,124,455 A | 6/1992 | Lombardo |
| 5,140,015 A | 8/1992 | Olsson et al. |
| 5,189,027 A | 2/1993 | Miyashita et al. |
| 5,272,153 A | 12/1993 | Mandell et al. |
| 5,278,150 A | 1/1994 | Olsson et al. |
| 5,298,508 A | 3/1994 | Jacobson et al. |
| 5,364,862 A | 11/1994 | Spada et al. |
| 5,561,134 A | 10/1996 | Spada et al. |
| 5,565,462 A | 10/1996 | Eitan et al. |
| 5,593,973 A | 1/1997 | Carter |
| 5,593,975 A | 1/1997 | Cristalli |
| 5,593,976 A | 1/1997 | Mongelli et al. |
| 5,665,754 A | 9/1997 | Feldman et al. |
| 5,668,139 A | 9/1997 | Belardinelli et al. |
| 5,696,254 A | 12/1997 | Mansour et al. |
| 5,731,296 A | 3/1998 | Sollevi |
| 5,756,706 A | 5/1998 | Mansour et al. |
| 5,776,940 A | 7/1998 | Daluge et al. |
| 5,854,081 A | 12/1998 | Linden et al. |
| 5,877,180 A | 3/1999 | Linden et al. |
| 5,932,558 A | 8/1999 | Cronstein et al. |
| 5,998,386 A | 12/1999 | Feldman |
| 6,004,945 A | 12/1999 | Fukunaga |
| RE36,494 E | 1/2000 | Olsson et al. |
| 6,020,321 A | 2/2000 | Cronstein et al. |
| 6,020,339 A | 2/2000 | Perrier et al. |
| 6,034,089 A | 3/2000 | Han et al. |
| 6,060,481 A | 5/2000 | LaNoue et al. |
| 6,117,878 A | 9/2000 | Linden et al. |

(Continued)

FOREIGN PATENT DOCUMENTS

EP 0488336 B1 5/1995

(Continued)

OTHER PUBLICATIONS

*The Merck Manual of Diagnosis and Therapy*, Beers, M.A., et al. (eds.), Merck and Company, (Jan. 1999), 924-925.
*Taber's Cyclopedic Medical Dictionary, 19th Edition*, Venes, et al. (eds.), F. A. Davis, Philadelphia, (2001), 960-961.
"U.S. Appl. No. 09/333,387, Non-Final Office Action mailed Jul. 13, 2000", 5 pgs.
"U.S. Appl. No. 09/333,387, Notice of Allowance mailed Mar. 7, 2001", 4 pgs.
"U.S. Appl. No. 09/333,387, Notice of Allowance mailed Aug. 25, 2000", 2 pgs.

(Continued)

*Primary Examiner* — Traviss C McIntosh, III
(74) *Attorney, Agent, or Firm* — Schwegmann, Lundberg & Woessner, P.A.

(57) ABSTRACT

The invention provides compounds having the following general formula (I):

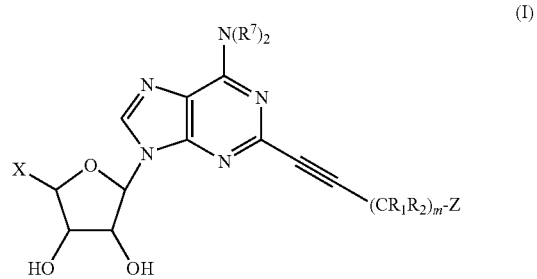

wherein X, $R^1$, $R^2$, $R^7$ and Z are as described herein.

20 Claims, 2 Drawing Sheets

U.S. PATENT DOCUMENTS

| | | | |
|---|---|---|---|
| 6,232,297 B1 | 5/2001 | Linden et al. | |
| 6,303,619 B1 | 10/2001 | Linden et al. | |
| 6,322,771 B1 | 11/2001 | Linden et al. | |
| 6,326,359 B1 | 12/2001 | Monaghan et al. | |
| 6,339,072 B2 | 1/2002 | Martin et al. | |
| 6,350,735 B1 | 2/2002 | Monaghan | |
| 6,387,889 B1 | 5/2002 | Endo et al. | |
| 6,407,076 B1 | 6/2002 | Box et al. | |
| 6,448,235 B1 | 9/2002 | Linden et al. | |
| 6,514,949 B1 | 2/2003 | Linden et al. | |
| 6,525,032 B2 | 2/2003 | Mantrell et al. | |
| 6,531,457 B2 | 3/2003 | Linden et al. | |
| 6,545,002 B1 | 4/2003 | Linden et al. | |
| 6,624,158 B2 | 9/2003 | Mantell et al. | |
| 6,670,334 B2 | 12/2003 | Linden | |
| 6,936,596 B2 | 8/2005 | Konno et al. | |
| 7,214,665 B2 | 5/2007 | Linden et al. | |
| 7,378,400 B2 * | 5/2008 | Rieger et al. | 514/46 |
| 7,427,606 B2 | 9/2008 | Linden et al. | |
| 7,605,143 B2 * | 10/2009 | Rieger et al. | 514/46 |
| 7,737,127 B2 | 6/2010 | Linden et al. | |
| 2001/0027185 A1 | 10/2001 | Linden et al. | |
| 2002/0032168 A1 | 3/2002 | Mantrell et al. | |
| 2002/0058641 A1 | 5/2002 | Mantell et al. | |
| 2002/0072597 A1 | 6/2002 | Mantell et al. | |
| 2003/0013675 A1 | 1/2003 | Yeadon et al. | |
| 2003/0162742 A1 | 8/2003 | Linden et al. | |
| 2003/0186926 A1 | 10/2003 | Linden et al. | |
| 2005/0182018 A1 | 8/2005 | Linden et al. | |
| 2005/0282831 A1 | 12/2005 | Beauglehole et al. | |
| 2006/0040889 A1 | 2/2006 | Rieger et al. | |
| 2006/0217343 A1 | 9/2006 | Rieger et al. | |
| 2007/0232559 A1 | 10/2007 | Linden et al. | |
| 2008/0009460 A1 | 1/2008 | Linden et al. | |
| 2008/0027022 A1 | 1/2008 | Linden et al. | |
| 2009/0162282 A1 | 6/2009 | Thompson et al. | |
| 2009/0162292 A1 | 6/2009 | Thompson et al. | |
| 2009/0280059 A1 | 11/2009 | Rieger et al. | |
| 2009/0298788 A1 | 12/2009 | Rieger et al. | |
| 2010/0152127 A1 | 6/2010 | Linden et al. | |

FOREIGN PATENT DOCUMENTS

| | | |
|---|---|---|
| EP | 0700908 A1 | 3/1996 |
| EP | 1150991 B1 | 11/2001 |
| EP | 1194440 A2 | 4/2002 |
| HU | 174074 | 10/1979 |
| WO | WO-93/22328 A1 | 11/1993 |
| WO | WO-95/11681 A1 | 5/1995 |
| WO | WO-96/02553 A2 | 2/1996 |
| WO | WO-96/04280 A1 | 2/1996 |
| WO | WO-9847509 A1 | 10/1998 |
| WO | WO-98/57651 A1 | 12/1998 |
| WO | WO-98/57661 A1 | 12/1998 |
| WO | WO-99/34804 A1 | 7/1999 |
| WO | WO-99/38877 A2 | 8/1999 |
| WO | WO-99/41267 A1 | 8/1999 |
| WO | WO-99/62518 A1 | 12/1999 |
| WO | WO-99/63938 A2 | 12/1999 |
| WO | WO-99/67263 A1 | 12/1999 |
| WO | WO-99/67264 A1 | 12/1999 |
| WO | WO-99/67265 A1 | 12/1999 |
| WO | WO-99/67266 A1 | 12/1999 |
| WO | WO-00/23457 A1 | 4/2000 |
| WO | WO-0044763 A2 | 8/2000 |
| WO | WO-00/72799 A2 | 12/2000 |
| WO | WO-00/78777 | 12/2000 |
| WO | WO-0078774 A2 | 12/2000 |
| WO | WO-01/94368 A1 | 12/2001 |
| WO | WO-02/09701 A1 | 2/2002 |
| WO | WO-02/22630 A1 | 3/2002 |
| WO | WO-02/096462 A1 | 12/2002 |
| WO | WO-03/004137 A1 | 1/2003 |
| WO | WO-03/014137 A1 | 2/2003 |
| WO | WO-03/029264 A2 | 4/2003 |
| WO | WO-03/086408 A1 | 10/2003 |
| WO | WO-2005/097140 A2 | 10/2005 |
| WO | WO-2006/015357 A2 | 2/2006 |
| WO | WO-2006/023272 A1 | 3/2006 |
| WO | WO-2006/028618 A1 | 3/2006 |
| WO | WO-2007/092936 A2 | 8/2007 |

OTHER PUBLICATIONS

"U.S. Appl. No. 09/333,387, Response filed Aug. 28, 2000 to Non-Final Office Action mailed Jul. 13 2000", 2 pgs.

"U.S. Appl. No. 09/333,387, Supplemental Amendment filed Aug. 28, 2000", 2 pgs.

"U.S. Appl. No. 10/263,379, Advisory Action mailed Mar. 1, 2006", 7 pgs.

"U.S. Appl. No. 10/263,379, Advisory Action mailed Apr. 11, 2006", 5 pgs.

"U.S. Appl. No. 10/263,379, Final Office Action mailed Nov. 1, 2006", 6 pgs.

"U.S. Appl. No. 10/263,379, Final Office Action mailed Nov. 9, 2005", 17 pgs.

"U.S. Appl. No. 10/263,379, Final Office Action mailed Nov. 23, 2004", 46 pgs.

"U.S. Appl. No. 10/263,379, Non Final Office Action mailed Apr. 25, 2005", 15 pgs.

"U.S. Appl. No. 10/263,379, Non Final Office Action mailed Jun. 14, 2006", 10 pgs.

"U.S. Appl. No. 10/263,379, Non Final Office Action mailed Jun. 17, 2004", 54 pgs.

"U.S. Appl. No. 10/263,379, Notice of Allowance mailed Dec. 12, 2006", 5 pgs.

"U.S. Appl. No. 10/263,379, Response filed Feb. 8, 2006 to Final Office Action mailed Nov. 9, 2005", 19 pgs.

"U.S. Appl. No. 10/263,379, Response filed Feb. 23, 2005 to Final Office Action mailed Nov. 23, 2004", 20 pgs.

"U.S. Appl. No. 10/263,379, Response filed Apr. 4, 2006 to Advisory Action mailed Mar. 1, 2006", 19 pgs.

"U.S. Appl. No. 10/263,379, Response filed May 2, 2006 to Advisory Action mailed Apr. 11, 2006", 15 pgs.

"U.S. Appl. No. 10/263,379, Response filed Sep. 11, 2006 to Non Final Office Action mailed Jun. 14, 2006", 15 pgs.

"U.S. Appl. No. 10/263,379, Response filed Sep. 26, 2005 to Non Final Office Action mailed Apr. 25, 2005", 19 pgs.

"U.S. Appl. No. 10/263,379, Response filed Oct. 18, 2004 to Non Final Office Action mailed Jun. 17, 2004", 25 pgs.

"U.S. Appl. No. 10/263,379, Response filed Nov. 21, 2006 to Final Office Action mailed Nov. 1, 2006", 13 pgs.

"U.S. Appl. No. 10/412,726, Final Office Action mailed Jul. 23, 2008", 15 pgs.

"U.S. Appl. No. 10/412,726, Final Office Action mailed Oct. 8, 2004", 7 pgs.

"U.S. Appl. No. 10/412,726, Final Office Action mailed Dec. 5, 2005", 13 pgs.

"U.S. Appl. No. 10/412,726, Non-Final Office Action mailed Mar. 16, 2005", 15 pgs.

"U.S. Appl. No. 10/412,726, Non-Final Office Action mailed Apr. 7, 2004", 8 pgs.

"U.S. Appl. No. 10/412,726, Non Final Office Action mailed Oct. 30, 2006", 12 pgs.

"U.S. Appl. No. 10/412,726, Response filed Feb. 8, 2005 to Final Office Action mailed Oct. 8, 2004", 22 pgs.

"U.S. Appl. No. 10/412,726, Response filed Apr. 27, 2007 to Non Final Office Action mailed Oct. 30, 2006", 23 pgs.

"U.S. Appl. No. 10/412,726, Response filed May 5, 2006 to Final Office Action mailed Dec. 5, 2005", 23 pgs.

"U.S. Appl. No. 10/412,726, Response filed Jul. 9, 2004 to Non Final office action mailed Apr. 7, 2004", 20 pgs.

"U.S. Appl. No. 10/412,726, Response filed Sep. 16, 2005 to Non Final office action mailed Mar. 16, 2005", 25 pgs.

"U.S. Appl. No. 10/412,726, Final Office Action mailed Jul. 19, 2007", 10 pgs.

"U.S. Appl. No. 10/412,726, Response filed Apr. 10, 2008 to Non-Final Office Action mailed Feb. 22, 2008", 30 pgs.

"U.S. Appl. No. 10/412,726, Response filed Oct. 31, 2007 to Final Office Action mailed Jul. 19, 2007", 28 pgs.

"U.S. Appl. No. 10/412,726, Non-Final Office Action mailed Feb. 22, 2008", OARN, 10 Pgs.

"U.S. Appl. No. 11/196,529, Response filed Aug. 7, 2008 to Non Final Office Action mailed Jun. 23, 2008", 21 pgs.

"U.S. Appl. No. 11/196,529, Response filed Dec. 19, 2008 to Final Office Action mailed Dec. 2, 2008", 19 pgs.

"U.S. Appl. No. 11/196,798, Non-Final Office Action mailed Mar. 31, 2008", 30 Pgs.

"U.S. Appl. No. 11/196,798, Response filed May 21, 2008 to Non Final Office Action mailed Apr. 21, 2008", 18 pgs.

"U.S. Appl. No. 11/196,802, Notice of Allowance mailed Mar. 28, 2008.", 33 pgs.

"International Search Report for corresponding PCT Application No. PCT/US2005/027474", (Jan. 25, 2006), 5 pgs.

"International Search Report for corresponding PCT Application No. PCT/US2005/027479", (Sep. 6, 2006), 6 pgs.

"New Zealand Application Serial No. 556354, Examination Report mailed Jul. 11, 2007", 21 pgs.

"PCT Application No. PCT/US07/61919, International Search Report mailed Nov. 7, 2007", 3 pgs.

"PCT Application No. PCT/US07/61919, Written Opinion mailed Nov. 7, 2007", 8 pgs.

Abiru, T., et al., "Nucleosides and nucleotides. 107. 2-(cycloalkylalkynyl)adenosines: adenosine $A_2$ receptor agonists with potent antihypertensive effects", *Journal of Medicinal Chemistry*, 35(12), (Jun. 12, 1992), 2253-2260.

Adah, S. A, et al., "Synthesis of complex ethynyladenosines using organic triflic enolates in palladium-catalyzed reactions: Potential agonists for the adenosine $A_2$ receptor", *Tetrahedron*, 53(20), (May 19, 1997), 6747-6754.

Ali, H., et al., "Methylxanthines Block Antigen-induced Responses in RBL-2H3 Cells Independently of Adenosine Receptors or Cyclic AMP: Evidence for Inhibition of Antigen Binding to IgE", *Journal of Pharmacology and Experimental Therapeutics*, 258, (1991), 954-962.

Andersson, P., et al., "Anti-anaphylactic and anti-inflammatory effects of xanthines in the lung", *Curr. Clin. Pract. Ser.*, (1985), 187-192.

Baraldi, P. G., et al., "Synthesis and Biological Activity of a New Series of $N^6$-Arylcarbamoyl, 2-(Ar)alkynyl-$N^6$-arylcarbamoyl, and $N^6$-Carboxamido derivatives of adenosine-5'-N-ethyluronamide as $A_1$ and $A_3$ Adenosine receptor agonists", *Journal of Medicinal Chemistry*, 41(17), (Aug. 13, 1998), 3174-3185.

Berkich, D. A., et al., "Evidence of Regulated Coupling of $A_1$ Adenosine Receptors by Phosphorylation in Zucker Rats.", *American Journal of Physiology*, 268 (4), (Apr. 1995), E693-E704.

Bhattacharya, S., et al., "Effects of Long-term Treatment With the Allosteric Enhancer, PD81,723, on Chinese Hamster Ovary Cells Expressing Recombitant Human $A_1$ Adenosine Receptors", *Molecular Pharmacology*, 50 (1), , (Jul. 1996), 104-111.

Bhattacharya, S., et al., "The Allosteric Enhancer, PD 81,723, Stabilizes Human $A_1$ Adenosine Receptor Coupling to G Proteins", *Biochimica et Biophysica Acta*, 1265 (1), , (Feb. 1995), 15-21.

Bridges, A. J., et al., "$N^6$-[2-(3,5-Dimethoxyphenyl)-2-(2-Methylphenyl)-Ethyl]Adenosine and its Uronamide Derivatives. Novel Adenosine Agonists With Both High Affinity and High Selectivity for the Adenosine $A_2$ Receptor", *Journal of Medicinal Chemistry*, 31(7), (Jul. 1988), 1282-1285.

Bruns, R. F., "Adenosine Receptors—Roles and Pharmacology", *Biological Actions of Extracellular ATP*, 603, Annals of the New York Academy of Sciences, (1990), pp. 211-226.

Bruns, R. F., et al., "Characterization of the $A_2$ Adenosine Receptor Labeled by [$^3$H]NECA in Rat Striatal Membranes", *Molecular Pharmacology*, 29, , (1986), 331-346.

Buster, B., et al., "The Effect of Adenosine Receptor Agonists on Neutrophil Pleocytosis and Blood-Brain Barrier Pathophysiology in Experimental Bacterial Meningitis", *Abstract of the Interscience Conference on Antimicrobial Agents and Chemotherapy*, 37, Abstract No. B-72, (1997), p. 39.

Camaioni, E, et al., "Adenosine receptor agonists: synthesis and bilogical evaluation of the diastereoisomers of 2-(3-Hydroxy-3-phenyl-1-propyn-1-yl)NECA", *Bioorganic & Medicinal Chemistry*, 5(12), (Dec. 1997), 2267-2275.

Carruthers, A. M., et al., "Hypotensive Responses to the Putative Adenosine $A_3$ Receptor Agonist $N^6$-2-(4-Aminophenyl)-Ethyladenosine in the Rat", *Drug Development Research*, 30, (1993), 147-152.

Cassada, D. C., et al., "Adenosine $A_{2A}$ agonist reduces paralysis after spinal cord ischemia: correlation with $A_{2A}$ receptor expression on motor neurons", *Annals of Thoracic Surgery*, 74(3), (Sep. 2002), 846-849; discussion 849-850.

Cassada, D. C., et al., "Adenosine $A_{2A}$ analogue ATL-146e reduces systemic tumor necrosing factor-α and spinal cord capillary platelet-endothelial cell adhesion molecule-1 expression after spinal cord ischemia", *Journal of Vascular Surgery*, 35(5), (May 2002), 994-998.

Cassada, D. C., et al., "Adenosine $A_{2A}$ analogue improves neurologic outcome after spinal cord trauma in the rabbit.", *Journal of Trauma-Injury Infection & Critical Care*, 53(2), (Aug. 2002), 225-229.

Cassada, D. C., et al., "Adenosine Analogue Reduces Spinal Cord Reperfusion Injury in a Time-Dependent Fashion", *Surgery*, 130(2), (Aug. 2001), 230-35.

Cassada, D C, et al., "An adenosine $A_{2A}$ agonist, ATL-146e, reduces paralysis and apoptosis during rabbit spinal cord reperfusion.", *Journal of Vascular Surgery*, 34(3), (Sep. 2001), 482-488.

Cassada, D C, et al., "Systemic adenosine $A_{2A}$ agonist ameliorates ischemic reperfusion injury in the rabbit spinal cord", *Annals of Thoracic Surgery*, 72(4), (Oct. 2001), 1245-1250.

Cembrzynska-Nowak, M, et al., "Elevated Release of Tumor Necrosis Factor-alpha and Interferon-gamma by Bronchoalveolar Leukocytes From Patients With Bronchial Asthma.", *American Review of Respiratory Disease*, 147(2), (1993), 291-295.

Chies, J. A. B., et al., "Sickle Cell Disease: A Chronic Inflammatory Condition", *Medical Hypotheses*, 57(1), (2001), 46-50.

Cothran, D. L., et al., "Ontogeny of Rat Myocardial $A_1$ Adenosine Receptors", *Biol Neonate*, 68 (2), , (1995), pp. 111-118.

Cristalli, G., "2-Alkynyl Derivatives of Adenosine an Adenosine-5'-N-ethyluronamide as Selective Agonists at $A_2$ Adenosine Receptors", *Journal of Medicinal Chemistry*, 35 (13), (1992), pp. 2363-2368.

Cristalli, G., et al., "2-Alkynyl derivatives of adenosine-5'-N-ethyluronamide: selective $A_2$ adenosine receptor agonists with potent inhibitory activity on platelet aggregation.", *J Med Chem.*, 37(11), (May 27, 1994), 1720-6.

Cristalli, G., et al., "2-Aralkynyl and 2-Heteroalkynyl Derivatives of Adenosine-5'-N-ethyluronamide as Selective $A_{2a}$ Adenosine Receptor Agonists", *J. Med. Chem.*, 38 (9), (1995), 1462-1472.

Cristalli, G., et al., "Characterization of Potent Ligands at Human Recombinant Adenosine Receptors", *Drug Development Research*, 45, Research Overview, (1998), 176-181.

Cronstein, B N., et al., "Neutrophil Adherence to Endothelium is Enhanced Via Adenosine $A_1$ Receptors and Inhibited Via Adenosine $A_2$ Receptors", *The Journal of Immunology*, 148 (7), (1992), pp. 2201-2206.

Cronstein, B. N., "Adenosine Modulates the Generation of Superoxide Anion by Stimulated Human Neutrophils Via Interaction With a Specific Cell Surface Receptor", *Annals New York Academy of Science*, 451, (1985), 291-314.

Cronstein, B. N., "Adenosine; A Physiologic Modulator of Superoxide Anion Generated by Human Neutrophils. Adenosine Acts Via an $A_2$ Receptor on Human Neutrophils", *Journal of Immunology*, 135 (2), (1985), 1366-1371.

Cronstein, B. N., "Engagement of Adenosine Receptors Inhibits Hydrogen Peroxide (H2O2) Release by Activated Human Neutrophils", *Clinical Immunology and Immunopathology*, 42(1), (1987), 76-85.

Cronstein, B. N., "Methotrexate Inhibits Leukocyte Influx Into Inflammatory Sites Via the Adenosine (A2) Receptor", *Clinical Research*, 41 (2), (1993), p. 244A.

Cronstein, B. N., et al., "Occupancy of Adenosine Receptors Raises Cyclic AMP Alone and in Synergy With Occupancy of Chemoattractant Receptors and Inhibits Membrane Depolarization", *Biochemical Journal*, 252 (3), (1988), 709-715.

Cronstein, B. N., "The Adenosine/Neutrophil Paradox Resolved: Human Neutrophils Possess Both $A_1$ and $A_2$ Receptors That Promote Chemotaxis and Inhibits $O_2$ Generation, Respectively", *Journal of Clinical Investigation*, 85(4), (1990), 1150-1157.

Day, Y., et al., "$A_{2A}$ adenosine receptors on bone marrow-derived cells protect liver from ischemia-reperfusion injury", *The Journal of Immunology*, 174(8), (Apr. 15, 2005), 5040-5046.

Day, Y. J., et al., "Renal Protection from Ischemia Mediated by $A_{2A}$ Adenosine Receptors on Bone Marrow-Derived Cells.", *Journal of Clinical Investigation*, 112(6), (2003), 883-891.

Day, Y.-J., et al., "Protection From Ischemic Liver Injury by Activation of $A_{2A}$ Adenosine Receptors During Reperfusion: Inhibition of Chemokine Induction", *American Journal of Physiology Gastrointestinal and Liver Physiology*, 286, (2004), G285-293.

De La Harpe, J., "Adenosine Regulates the Respiratory Burst of Cytokine-Triggered Human Neutrophils Adherent to Biological Surfaces", *Journal of Immunology*, 143(2), (1989), 596-602.

De Moraes, V. L., et al., "Effect of Cyclo-Oxygenase Inhibitors and Modulators of Cyclic AMP Formation on Lipopolysaccharide-Induced Neutrophil Infiltration in Mouse Lung", *British Journal of Pharmacology*, 117, , (1996), pp. 1792-1796.

De Sarro, G., et al., "Effects of adenosine Receptor Agonists and Antagonists on Audiogenic Seizure-sensible DBA / 2 mice", *European Journal of Pharmacology*, 371, (1999), 137-145.

De Zwart, M, et al., "5-N-Substituted Carboxamidoadenosines as Agonists for Adenosine Receptors", *Journal of Medicinal Chemistry*, 42 (8), (Apr. 22, 1999), 1384-1392.

Dechatelet, L R., et al., "Mechanism of the Luminol-Dependent Chemiluminescence of Human Neutrophils", *The Journal of Immunology*, 129 (4), (1982), pp. 1589-1593.

Dinarello, C. A., "Interleukin-1 and Tumor Necrosis Factor: Effector Cytokines in Autoimmune Diseases", *Seminars in Immunology*, 4, (1992), 133-145.

Doyle, M. P., et al., "Nucleoside-induced Arteriolar Constriction: a Mast Cell-dependent Response.", *American Journal of Physiology*, 266(5), (May 1994), H2042-H2050.

Elzein, E., et al., "Design, Synthesis and Biological Evaluation of 2-(4-Substituted-N-Pyrazolyl)-Adenosine Derivatives as Novel Short Acting Adenosine A2A Receptor Agonists", (Abstract No. 061), *Drug Development Research*, 50 (1), Abstracts From Purines 2000: Biochemical, Pharmacological, and Clinical Perspectives: (May 2000), p. 64.

Fang, G. D., et al., "DWH146e (DWH), A New Selective Adenosine A2a Receptor Agonist, Improves Survival in *E. coli* O26:B6 Lipopolysaccharide (LPS)-Induced Experimental Murine Endotoxemia", *Journal of Investigative Medicine*, Abstract No. 797, (2000), p. 148A.

Fenster, M. S., et al., "Activation of adenosine $A_{2a}$ receptors inhibits mast cell degranulation and mast cell-dependent vasoconstriction", *Microcirculation*, 7(2), (Apr. 2000), 129-135.

Feoktistov, I., et al., "Adenosine $A_{2B}$ receptors", *The American Society for Pharmacology and Experimental Therapeutics*, 49(4), (1997), 381-402.

Feoktistov, I., et al., "Role of Adenosine in Asthma", *Drug Development Research*, 39, (1996), 333-336.

Ferrante, A., "Optimal Conditions for Simultaneous Purification of Mononuclear and Polymorphonuclear Leucocytes From Human Blood by the Hypaque-Ficoll Method", *Journal of Immunological Methods*, 36(2), (1980), 109-117.

Figler, R. A., et al., "Reconstitution of Bovine $A_1$ Adenosine Receptors and G Proteins in Phospholipid Vesicles: .βγ Subunit Composition Influences Guanine Nucleotide Exchange and Agonist Binding", *Biochemistry*, 36 (51), , (1997), 16288-16299.

Figler, R. A., et al., "Reconstitution of Recombinant Bovine $A_1$ Adenosine Receptors in Sf9 Cell Membranes with Recombinant G Proteins of Defined Composition.", *Molecular Pharmcology*, 50(6), (Dec. 1996), 1587-1595.

Firestein, G. S., "Adenosine Regulating Agents: A Novel Approach to Inflammation and Inflammatory Arthritis", *Clinical Research*, 41(2), (1993), p. 170A.

Fiser, S M, et al., "Adenosine $A_{2A}$ receptor activation decreases reperfusion injury associated with high-flow reperfusion.", *Journal of Thoracic & Cardiovascular Surgery*, 124(5), (Nov. 2002), 973-978.

Fozard, J. R., et al., "Adenosine $A_3$ Receptors Mediate Hypotension in the Angiotensin II-supported Circulation of the Pithed Rat", *British Journal of Pharmacology*, 109(1), (1993), 3-5.

Francis, J. E., "Highly Selective Adenosine $A_2$ Receptor Agonists in a Series of N-Alkylated 2-Aminoadenosines", *Journal of Medicinal Chemistry*, 34 (8), (1991), 2570-2579.

Frangogiannis, N. G., et al., "The Role of the Neutrophil in Myocardial Ischemia and Reperfusion", *Myocardial Iscehmia: Mechanisms, Reperfusion, Protection*, M. Karmazyn, Editor, Birkhauser Verlag Basel, (1996), 236-284.

Gao, Z, et al., "Purification of $A_1$ Adenosine Receptor-G-protein Complexes: Effects of Receptor Down-regulation and Phosphorylation on Coupling", *Biochemical Journal*, 338 (Pt3), (1999), 729-736.

Gao, Z., et al., "$A_{2B}$ Adenosine and $P2Y_2$ Receptors Stimulate Mitogen-activated Protein Kinase in Human Embryonic Kidney-293 Cells. Cross-talk Between Cyclic AMP and Protein Kinase c Pathways", *Journal of Biological Chemistry*, 274(9), (Feb. 26, 1999), 5972-5980.

Gilchrist, A., et al., "Antagonists of the Receptor-G Protein Interface Block Gi-coupled Signal Transduction", *Journal of Biological Chemistry*, 273 (24), (Jun. 12, 1998), 14912-14919.

Girardi, N, et al., "Inflammatory Aneurysm of the Ascending Aorta and Aortic Arch", *Ann Thor. Surg.*, 64, (1997), 251-253.

Glover, D K, et al., "Pharmacological stress myocardial perfusion imaging with the potent and selective $A_{2A}$ adenosine receptor agonists ATL193 and ATL146e administered by either intravenous infusion or bolus injection", *Circulation*, 104(10), (Sep. 4, 2001), 1181-1187.

Glover, D. K., et al., "Bolus Injection of DWH-146E, A Novel Adenosine $A_{2A}$ Receptor Agonist for Use in Vasodilator Stress Imaging", (Abstract No. 44.20), *Journal of Nuclear Cardiology*, 7 (4), (Sep. 23, 2000), 1 pg.

Glover, D. K., et al., "Characterization of a New, Highly Selective Adenosine $A_{2A}$ Receptor Agonist with Potential Use in Pharmacologic Stress Perfusion Imaging", *Circulation*, 100, (Abstract Only), (1999), 1 pg.

Glover, D. K., et al., "Pharmacological stress thallium scintigraphy with 2-cyclohexylmethylidenehydrazinoadenosine (WRC-0470). A novel, short-acting adenosine $A_{2A}$ receptor agonist.", *Circulation*, 94(7), (Oct. 1, 1996), 1726-1732.

Glover, D. K., et al., "Vasodilator Stress Imaging Using New Adenosine $A_{2A}$ Receptor Agonists Administered by Bolus Injection", *J. Am. Coll. Cardiol.*, 35, Abstract, (2000), 1 pg.

Griswold, D. E., et al., "Effect of Selective Phosphodieasterase Type IV Inhibitor, Rolipram, on Fluid and Cellular Phases of Inflammatory Response", *Inflammation*, 17(3), (1993), 333-344.

Hanlon, W. A., "rTNFα Facilitate Human Polymorphonuclear Leukocyte Adherence to Fibrinogen Matrices With Mobilization of Specific and Tertiary But Not Azurophilic Granule Markers", *Journal of Leukocyte Biology*, 50 (1), (1991), 43-48.

Hartung, H. P., "Immune-Mediated Demyelination", *Annals of Neurology*, 33 (6), (Jun. 1993), 563-567.

Heller, L. J., et al., "Effect of Adenosine on Histamine Release and Atrioventricular Conduction During Guinea Pig Cardiac Anaphylaxis", *Circulation Research*, 62(6), (Jun. 1988), 1147-1158.

Hogan, C. J., et al., "Inhibiting the inflammatory response in joint sepsis", *Arthroscopy*, 17(3), (Mar. 2001), 311-315.

Holmes, D, R., et al., "Restenosis After Percutaneous Transluminal Coronary Angioplasty (PTCA): A Report From the PTCA Registry of the National Heart, Lung, and Blood Institute", *American Journal of Cardiology*, 53, (1984), 77C-81C.

Homma, H, et al., "Nucleosides and nucleotides. 112. 2-(1-Hexyn-1-yl)adenosine-5'-uronamides: a new entry of selective $A_2$ adenosine receptor agonists with potent antihypertensive activity.", *Journal of Medicinal Chemistry*, 35(15), (Jul. 1992), 2881-90.

Hussain, T., et al., "125I-APE Binding to Adenosine Receptors in Coronary Artery: Photoaffinity Labeling With 125I-azidoAPE", *The Journal of Pharmacology and Experimental Therapeutics*, 276 (1), , (Jan. 1996), 284-288.

Hutchison, A. J., "2-(Arylalkylamino)Adenosine-5'-Uronamides: A New Class of Highly Selective Adenosine $A_2$ Receptor Ligands", *Journal of Medicinal Chemistry*, 33 (7), (1990), pp. 1919-1924.

Hutchison, A. J., "CGS 21680C, an $A_2$ Selective Adenosine Receptor Agonist With Preferential Hypotensive Activity", *The Journal of Pharmacology and Experimental Therapeutics*, 251 (1), (1989), 47-55.

Iannone, M. A., "Effects of Adenosine on Human Neutrophil Function and Cyclic AMP Content", *In: Topics and Perspectives in Adenosine Research*, Eds. E. Gerlach et al., Springer-Verlag, Berlin, Germany, (1986), 286-298.

Imagawa, D. K., et al., "The Role of Tumor Necrosis Factor in Allograft Rejection", *Transplantation*, 51, , (Jan. 1991), 57-62.

Ishiwata, K., et al., "Further Characterization of a CNS Adenosine A2a Receptor Ligand [11C]KF18446 with in vitro Autoradiography and in vivo Tissue Uptake", (Abstract No. 346544), *Annals of Nuclear Medicine*, 14(2), Abstract Only, Obtained from Chemicals Abstracts, 133, , HCAPlus Accession No. 480897 (2000), (2000), 81-89.

Ito, B. R., et al., "Role of Cardiac Mast Cells in Complement C5a-induced Myocardial Ischemia", *American Journal of Physiology—Heart and Circulatory Physiology*, 264(5), (May 1993), H1346-H1354.

Jarvis, M. F., "[3H]CGS 21680, A Selective $A_2$ Adenosine Receptor Agonist Directly Labels $A_2$ Receptors in Rat Brain.", *Journal of Pharmacology and Experimental Therapeutics*, 251(3), (Dec. 1989), 888-893.

Jolly, S. R., "Effects of Lodoxamide on Ischemic Reperfused Myocardium", *Journal of Cardiovascular Pharmacology*, 4(3), (1982), 441-448

Kaminuma, O., et al., "Effect of T-440, a Novel Type IV Phosphodiesterase Inhibitor, on Allergen-Induced Immediate and Late Asthmatic Reaction and Leukocyte Infiltration into the Airways of Guinea Pigs", *International Archives of Allergy & Immunology*, 112(4), (1997), 406-411.

Keller, A. M., "Acute Reoxygeneration Injury in the Isolated Rat Heart: Role of Resident Cardiac Mast Cells", *Circulation Research*, 63(6), (Dec. 1988), 1044-1052.

Kennedy, A. P., et al., "Covalent Modification of Transmembrane Span III of the $A_1$ Adenosine Receptor With an antagonist Photoaffinity Probe.", *Molecular Pharmacology*, 50, , (Oct. 1996), 789-798.

Klotz, Karl-Norbert, et al., "2-Substituted N-ethylcarboxamidoadenosine derivatives as high-affinity agonists at human $A_3$ adenosine receptors", *Naunyn-Schmiedebergs Archives of Pharmacology*, 360(2), (Aug. 1999), 103-108.

Knapp, C. M., et al., "The Type IV Phosphodiester Inhibitors, Ro 20-1724 and Rolipram,Block the Initiation of Cocaine Self Administration", *Pharmocology, Biochemistry and Behavior*,62(1), (Jan. 1999), 151-158.

Kollias-Baker, C., et al., "Allosteric Enhancer PD 81,723 Acts by Novel Mechanism to Potentiate Cardiac Actions of Adenosine", *Circulation Research*, 75(6), (Dec. 1994), 961-971.

Koshiba, M, et al., "Patterns of $A_{2A}$ Extracellular Adenosine Receptor Expression in Different Functional Subsets of Human Peripheral T Cells. Flow Cytometry Studies With Anti-$A_{2A}$ Receptors Monoclonal Antibodies.", *Molecular Pharmacology*, 55 (3), , (Mar. 1999), 614-624.

Koshiba, M., "Patterns of A2A Extracellular Adenosine Receptor Expression in Different Functional Subsets of Human Peripheral T Cells", (Abstract No. 703.38), *The FASEB Journal*, ,(1999), p. A944.

Lappas, C. M, et al., "$A_{2A}$ adenosine receptor induction inhibits IFN-γ production in murine CD4+ T cells", *Journal of Immunology*, 174(2), (Jan. 15, 2005), 1073-1080.

LeClerc, G., et al., "Percutaneous Arterial Gene Transfer in a Rabbit Model", *Journal of Clinical Investigation*, 90 (3), (1992), 936-944.

Legrand-Poels, S., et al., "Activation of Human Immunodeficiency Virus Type 1 by Oxidative Stress", *AIDS Research and Human Retroviruses*, 6(12), (1990), 1389-1397.

Lette, J., et al., "Safety of Dipyridamole Testing in 73,806 Patients: The Multicenter Dipyridamole Safety Study", *Journal of Nuclear Cardiology*, 2 (1), , (1995), 3-17.

Linden, J, "Cloned Adenosine $A_3$ Receptors: Pharmacological Properties, Species Differences and Receptor Functions.", *Trends in Pharmacological Sciences*, 15 (8), (Aug. 1994), 298-306.

Linden, J, et al., "The Structure and Function of $A_1$ and $A_{2B}$ Adenosine Receptors", *Life Science*, 62 (17/18), , (1998), 1519-1524.

Linden, J., et al., "(125I)Aminobenzyladenosine, a New Radioligand with Improved Specific Binding to Adenosine Receptors in Heart", *Circulation Research*, 56 (2), (Feb. 1985), 279-284.

Linden, J., "Allosteric Enhancement of Adenosine Receptors", *In: Purinergic Approaches in Experimental Therapeutics, Chapter 5*, Edited by K.A. Jacobson et al., and Published by Wiley-Liss, Inc., (1997), 85-97.

Linden, J., "Calculating the Dissociation Constant of an Unlabeled Compound from the Concentration Required to Displace Radiolabel Binding by 50%", *Journal of Cyclic Nucleotide Research*, 8 (3), (1982), pp. 163-172.

Linden, J., et al., "Chapter 2—Adenosine Receptors", *In: Handbook of Receptors and Channels—G Protein Coupled Receptors*, Peroutka, S. J., Editor, CRC Press, Boca Raton, FL, (1994), 29-44.

Linden, J., "Chapter 2—Recombinant Techniques as Applied to the Study of $A_1$ Adenosine Receptors", *In: Adenosine and Adenine Nucleotides: From Molecular Biology to Integrative Physiology*, Belardinelli, L., Editor, Kluwer Academic Publishers, Boston, (1995), 15-19.

Linden, J., et al., "Molecular Cloning and Functional Expression of a Sheep $A_3$ Adenosine Receptor with Widespread Tissue Distribution", *Molecular Pharmacology* 44(3), (1993), 524-532.

Link, A. A., et al., "Ligand-Activation of the Adenosine A2a Receptors Inhibits IL-12 Production by Human Monocytes", *The Journal of Immunology*, 164, (2000), 436-442.

Luthin, D. R., et al., "Adenosine Receptors", *Biomembranes*, 2B, (1996), 321-347.

Luthin, D. R., "Characterization of Two Affinity States of Adenosine $A_{2a}$ Receptors With a New Radioligand, 2-[2-(4-amino-3-[$^{125}$I]iodophenyl) Ethylamino]Adenosine.", *Molecular Pharmacology*, 47 (2), (Feb. 1995), 307-313.

Luthin, D. R., et al., "Comparison of $A_4$ and $A_{2a}$ Binding Sites in Striatum and COS Cells Transfected With Adesosine $A_{2a}$ Receptors.", *The Journal of Pharmacology and Experimental Therapeutics*, 272, , (Feb. 1995), 511-518.

Luthin, D. R., et al., "Photoaffinity Labeling With 2(−)[2-(4-azido-3(−)[$^{125}$I]-iodophenyl)ethylamino]Adenosine and Autoradiography With 2(−)[2-(4-amino-3(−)[$^{125}$I]iodophenyl)ethylamino]Adenosine of $A_{2a}$ Adenosine Receptor in Rat Brain.", *Journal of Neurochemistry*, 65 (5), , (Nov. 1995), 2072-2079.

Mager, P. P., "Neural network approaches applied to selective $A_{2a}$ adenosine receptor agonists", *Med. Chem. Res.*, 8(6), (1998), 277-290.

Mahan, L. C., et al., "Cloning and Expression of an A1 Adenosine Receptor from Rat Brain", *Molecular Pharmacology*, 40 (1), , (Jul. 1991), 1-7.

Mannel, D. N., "Tumor Necrosis Factor: A Cytokine Involved in Toxic Effects of Endotoxin", *Reviews of Infectious Diseases*, 9, (1987), S602-S606.

March, J., "", *Advanced Organic Chemistry: Reactions, Mechanisms, and Structure*, Fourth Edition, John Wiley & Sons, (1992), p. 400.

Martin, P. L., et al., "Characterization of 8-(N-Methylisopropyl)Amino-N$^6$-(5'-Endohydroxy-endonorbornyl)-9-methyladenine (WRC-0571), a Highly Potent and Selective, Nonxanthine Antagonist of $A_1$ Adenosine Receptors.", *The Journal of Pharmacology and Experimental Therapeutics*, 276(2), (Feb. 1996), 490-499.

Martin, P. L., et al., "Pharmacology of 2-cyclohexylmethylidenehydrazinoadenosine (WRC-0470), a Novel, Short-acting Adenosine $A_{2A}$ Receptor Agonist That Produces Selective Coronary Vasodilation.", *Drug Development Research*, 40 (4), , (1997), 313-324.

Matherne, G. P., et al., "Transgenic $A_1$ Adenosine Receptor Overexpression Increases Myocardial Resistance to Ischemia", *Proceedings of the National Academy of Science*, 94, (Jun. 1997), 6541-6546.

Matsuyama, T., "Cytokines and HIV Infection: is AIDS a Tumor Necrosis Factor Disease?", *AIDS*, 5(12), (1991), 1405-1417.

McGarrity, S. T., "Inhibition of Neutrophil Superoxide Anion Generation by Platelet Products: Role of Adenine Nucleotides", *Journal of Leukocyte Biology*, 44(5), (1988), 411-421.

McGarrity, S. T., "Regulation of Human Neutrophil Function by Adenine Nucleotides", *Journal of Immunology*, 142(6), (1989), 1986-1994.

McLaughlin, D. P., et al., "Hemodynamic and Metabolic Correlates of Dipyridamole-induced Myocardial Thallium-201 Perfusion Abnormalities in Multivessel Coronary Artery Disease.", *American Journal of Cardiology*, 73 (16), , (Jun. 1994), 1159-1164.

McPherson, J A, "Adenosine $A_{2A}$ receptor stimulation reduces inflammation and neointimal growth in a murine carotid ligation model", *Arteriosclerosis, Thrombosis & Vascular Biology*, 21(5), (May 2001), 791-796.

McPherson, J. A., et al., "Effect of Prolonged Adenosine A2A Receptor Activation on Neointimal Formation in the Injured Mouse Carotid Artery", (Abstract No. 299.2), *The FASEB Journal*, (1999), p. A367.

McPherson, J. A., et al., "Prolonged Adenosine A2a Receptor Stimulation Reduces Inflammation and Neointima Formation in a Murine Carotoid Ligation Model", (Abstract No. 3652), *Supplement to Circulation*, 100 (18), (Nov. 2, 1999), 1 pg.

Miyamoto, F, et al., "Retinal Cytokine Response in Mouse Alkali-Burned Eye", *Opthalmic Research*, 30, (1997), 168-171.

Mizumura, T., et al., "PD 81,723, an Allosteric Enhancer of the $A_1$ Adenosine Receptor, Lowers the Threshold for Ischemic Preconditioning in Dogs.", *Circulation Research*, 79 (3), , (Sep. 1996), 415-423.

Molnar-Kimber, K. L., et al., "Modulation of TNFα and IL-1β From Endotoxin-Stimulated Monocytes by Selective PDE Isozyme Inhibitors", *Agents & Actions*, 39, , (1993), C77-C79.

Mumby, S. M., et al., "G-protein α-subunit expression, myristoylation, and membrane association in COS cells", *Proceedings of the National Academy of Sciences*, 87 (2), , (Jan. 1990), 728-732.

Nabel, E. G., "Site-Specific Gene Expression in Vivo by Direct Gene Transfer into the Arterial Wall", *Science*, 249, (1990), 1285-1288.

Newman, K. D., "Adenovirus-mediated Gene Transfer into Normal Rabbit Arteries Results in Prolonged Vascular Cell Activation, Inflammation and Neointimal Hyperplasia", *Journal of Clinical Investigation*, 96 (6), (1995), 2955-2965.

Nielson, C. P., "Effects of Adenosine on Polymorphonuclear Leucocyte Function, Cyclic 3': 5'-adenosine Monophosphate, and Intracellular Calcium", *British Journal of Pharmacology*, 97(3), (1989), 882-888.

Niiya, K., "2-(N'-Alkylidenehydrazino)Adenosines: Potent and Selective Coronary Vasodilators", *Journal of Medicinal Chemistry*, 35(24), (1992), 4557-4561.

Nolte, D., et al., "Reduction of Postischemic Leukocyte-Endothelium Interaction by Adenosine Via $A_2$ Receptor", *Naunyn-Schmiedeberg's Archives of Pharmacology*, 346(2), (1992), 234-237.

Okusa, M D, et al., "$A_{2A}$ Adenosine Receptor-Mediated Inhibition of Renal Injury and Neutrophil Adhesion", *American Journal of Physiology—Renal Fluid & Electrolyte Physiology*, 279(5), (2000), F809-F818.

Okusa, M D, et al., "Enhanced Protection from Renal Ischemia: Reperfusion Injury With A2A-Adenosine Receptor Activation and PDE 4 Inhibition", *Kidney International*, 59(6), (2001), 2114-2125.

Okusa, M. D., et al., "Selective $A_{2A}$ adenosine receptor activation reduces ischemia-reperfusion injury in rat kidney", *Am. J. Physiol.*, vol. 277 (3, Pt 2), (1999), F404-F412.

Olsson, R. A., et al., "$N^6$ Substituted N-Alkyladenosine-5'-Uronamides: Bifunctional Ligands Having Recognition Groups for A1 and A2 Adenosine Receptors", *Journal of Medicinal Chemistry*, 29 (9), (1986), 1683-1689.

O'Regan, M. H., et al., "Adenosine Receptor Agonists Inhibit the Release of γ-Aminobutyric Acid (GABA) From the Ischemic Rat Cerebral Cortex", *Brain Research*, 582(1), (1992), 22-26.

Peart, J, et al., "Adenosine-mediated cardioprotection in ischemic-reperfused mouse heart.", *Journal of Cardiovascular Pharmacology*, 39(1), (Jan. 2002), 117-129.

Peet, N. P., et al., "Conformationally Restrained, Chiral (Phenylisopropyl)Amino-Substituted Pyrazolo[3,4-d]Pyrimidines and Purines With Selectivity for Adenosine $A_1$ and $A_2$ Receptors", *Journal of Medicinal Chemistry*, 35 (17), (1992), 3263-3269.

Peirce, S. M., "Selective $A_{2A}$ adenosine receptor activation reduces skin pressure ulcer formation and inflammation", *American Journal of Physiology—Heart & Circulatory Physiology*, 281(1), (Jul. 2001), H67-H74.

Peirce, S. M., et al., "Attenuation of I/R Injury in Skin Using a Selective A2A Adenosine Receptor Agonist", (Abstract No. 333.1), *FASEB Journal*, 14 (4), , (Mar. 15, 2000), p. A466.

Pennell, R. L., et al., "Inflammatory abdominal aortic aneurysms: A thirty-year review", *Journal of Vascular Surgery*, 2, (1985), 859-869.

Pfister, J. R., et al., "Synthesis and Biological Evaluation of the Enantiomers of the Potent and Selective $A_1$- adenosine Antagonist 1,3-dipropyl-8[2-(5,6-epoxynorbonyl)]-xanthine", *Journal of Medicinal Chemistry*, 40 (12), (1997), 1773-1778.

Pulle, V., et al., "Design, Synthesis and Pharmacological Evaluation of 2(1-Alkyl-Pyrazol-4-YL) Adenosine Derivatives as Short Acting Adenosine A2A Receptor Agonists", (Abstract No. 062), *Drug Development Research*, 50 (1), Abstracts From Purines 2000: Biochemical, Pharmacological and Clinical Perspectives:, (May 2000), p. 64.

Raitt, M. H., et al., "Abnormal Q Waves are Common Early in AMI and Do Not Predict Decreased Myocardial Salvage With Thrombolytic Therapy", *Special Issue Journal of American College of Cardiology*, Abstract No. 895-77, (Feb. 1994), p. 195A.

Ranhosky, A., et al., "The Safety of Intravenous Dipyridamole Thallium Myocardial Perfusion Imaging", *Circulation*, 81(4), , (Apr. 1990), 1205-1209.

Rieger, J. M., et al., "Design, Synthesis, and Evaluation of Novel $A_{2A}$ Adenosine Receptor Agonists", *Journal of Medicinal Chemistry*, 44(4), (2001), 531-539.

Riou, L M, et al., "Influence of propranolol, enalaprilat, verapamil, and caffeine on adenosine $A_{2A}$-receptor-mediated coronary vasodilation", *Journal of the American College of Cardiology*, 40(9), (Nov. 6, 2002), 1687-1694.

Roberts, P. A., et al., "Inhibition by Adenosine of Reactive Oxygen Metabolite Production by Human Polymorphonuclear Leucocytes", *Biochemical Journal*, 227(2), (1985), 669-674.

Robeva, A. S., et al., "Double Tagging Recombitant $A_1$- and $A_{2A}$-Adenosine Receptors With Hexahistidine and the FLAG Epitope. Development of an Efficient Generic Protein Purification Procedure.", *Biochemical Pharmacology*, 51(4), (Feb. 1996), 545-555.

Robeva, A. S., et al., "Molecular Characterization of Recombinant Human Adenosine Receptors", *Drug Development Research*, 39, , (1996), 243-252.

Rosin, D. L., et al., "Immunohistochemical Localization of Adenosine $A_{2A}$ Receptors in the Rat Central Nervous System", *The Journal of Comparative Neurology*, 401, , (1998), pp. 163-186.

Ross, R., "The Pathogenesis of Atherosclerosis: A Perspective for the 1990s", *Nature*, 362, (Apr. 29, 1993), 801-809.

Ross, S. D., et al., "Selective Adenosine-$A_{2A}$ Activation Reduces Lung Reperfusion Injury Following Transplantation", *Journal of Heart & Lung Transplantation*, 18(10), (1999), 994-1002.

Ross, S. D, et al., "Selective Adenosine-A2A Activation Reduces Lung Reperfusion Injury Following Transplantation", *Journal of Heart and lung transplantation*, 18 (1), (Abstract Only), Proceedings of the Nineteenth Annual Meeting and Scientific Sessions of the International Society for Heart and Lung Transplantation, San Francisco, CA, (Jan. 1999), p. 72.

Rothe, G. A., et al., "Flow Cytometric Measurement of the Respiratory Burst Activity of Phagocytes Using Dihydrorhodamine 123", *Journal of Immunological Methods*, 138(1), (1991), 133-135.

Sawmiller, D. R., et al., "Effects of Xanthine Amine Congener on Hypoxic Resistence and Venous and Epicardial Adenosine Concentrations.", *Cardiovascular Research*, 28 (5), , (May 1994), 604-609.

Schiffmann, S. N., et al., "Distribution of adenosine $A_2$ receptor mRNA in the human brain", *Neuroscience Letters*, 130, , (1991), pp. 177-181.

Schlack, W., et al., "Adenosine $A_2$-Receptor Activation at Reperfusion reduces Infarct Size and Improves Myocardial Wall Function in Dog Heart", *Journal of Cardiovascular Pharmacology*, 22, (1993), 89-96.

Schrier, D. J., et al., "The Effects of Adenosine Agonists on Human Neutrophil Function", *Journal of Immunology*, 137(10), (1986), 3284-3289.

Seekamp, A., "Ischemia—Reperfusion Injury", *Agents and Actions Supplements*, 41, (1993), 137-152.

Sharief, M. K., et al., "Elevated Serum Levels of Tumor Necrosis Factor-alpha in Guillain-Barre Syndrome", *Annals of Neurology*, 33, , (Jun. 1993), 591-596.

Sharma, H S, et al., "Role of cytokines in myocardial ischemia and reperfusion", *Med. of Inflamm.*, 6, (1987), 175-183.

Sheardown, M. J, "Unexpected Neuroprotection Observed with the Adenosine $A_{2A}$ Receptor Agonist CGS 21860", *Drug Development Research*, 39, (1996), 108-114.

Shepherd, R. K., et al., "Adenosine-induced Vasoconstriction in Vivo. Role of the Mast Cell and A3 Adenosine Receptor.", *Circulation Research*, 78 (4), , (Apr. 1996), 627-634.

Sipka, S., "Adenosine Induced Delay of Expression of AIDS Virus, HIV, in H9T Cells", *Acta. Biochimica et Biophysica Hungarica*, 23(1), (1988), 75-82.

Siragy, H. M., et al., "Sodium Intake Markedly Alters Renal Interstitial Fluid Adenosine", *Hypertension*, 27 (3 Pt 1), , (Mar. 1996), 404-407.

Smits, P., et al., "Cardiovascular effects of two xanthines and the relation to adenosine antagonism", *Clinical Pharmacology and Therapeutics*, 45(6), (1989), 593-599.

Sullivan, G W., et al., "Interactions of Human Neutrophils with Leukotoxic Streptococci", *Infection and Immunity*, 30 (1), (1980), 272-280.

Sullivan, G. W., "Adenosine (ADO) Modulates Endotoxin and TNF-Induced PMN Activation", *Clinical Research*, 41(2), (1993), p. 172A.

Sullivan, G. W, et al., "Neutrophil $A_{2A}$ adenosine receptor inhibits inflammation in a rat model of meningitis: synergy with the type IV phosphodiesterase inhibitor, rolipram", *J Infect Dis.*, 180(5), (Nov. 1999), 1550-60.

Sullivan, G. W., et al., "Role of $A_{2A}$ Adenosine Receptors in Inflammation", *Drug Development Research*, 45 (3/4), (1998), 103-112.

Sullivan, G. W., et al., "The role of inflammation in vascular diseases", *Journal of Leukocyte Bilogy*, 67, (May 2000), pp. 591-602.

Sullivan, G. W., et al., "The Specific Type IV Phosphodiesterase Inhibitor Rolipram Combined with Adenosine Reduces Tumor Necrosis Factor-a-Primed Neutrophil Oxidative Activity", *International Journal of Immunonopharmacology*, 17(10), (1995), 793-803.

Sullivan, G. W., "Two Methylxanthines, Pentoxifylline (PTX) and Caffeine (CAF) Have Divergent Effects on Tumor Necrosis Factor (TNF)-Primed Human Neutrophil (PMN) Activation", *Clinical Research*, 41(2), (1993), p. 172A.

Sullivan, G. W., et al., "Cyclic AMP-Dependent Inhibition of Human Neutrophil Oxidative Activity by Substitued 2-Propynylcyclohexyl Adenosine $A_{2A}$ Receptor Agonists", *British Journal of Pharmacology*, 132(5), (2001), 1017-1026.

Takiguchi, Y., et al., "Early administration of YT-146, an adenosine $A_2$ receptor agonist, inhibits neointimal thickening after rat femoral artery endothelium injury", *European Journal of Pharmacology 281*, (1995), 205-207.

Topol, E. J., et al., "Randomised Trial of Coronary Intervention With Antibody Against Platelet IIb/IIIa integrin for Reduction of Clinical Restenosis: Results at Six Months", *The Lancet*, 343(8902), (1994), 881-886.

Tracey, K. J., "Cachectin/Tumor Necrosis Factor Induces Cachexia, Anemia, and Inflammation", *Journal of Experimental Medicine*, 167, (Mar. 1988), 1211-1227.

Tucker, A. L., et al., "$A_1$ adenosine receptors. Two amino acids are responsible for species differences in ligand recognition", *Journal of Biological Chemistry*, 269(45), (Nov. 11, 1994), 27900-27906.

Ueeda, M., et al., "2- Alkoxyadenosines: Potent and Selective Agonists at the Coronary Artery $A_2$Adenosine Receptor", *Journal of Medicinal Chemistry*, 34(4), (1991),1334-1339.

Ukena, D., et al., "Species Differences in Structure-Activity Relationships of Adenosine Agonists and Xanthine Antagonists at Brain A1 Adenosine Receptors", *FEBS Letters*, 209 (1), (Dec. 1986), 122-128.

Underwood, D. C., et al., "Inhibition of Antigen-Induced Bronchoconstriction and Eosinophil Infiltration in the Guinea by the Cyclic AMP-Specific Phosphodiesterase Inhibitor, Rolipram", *The Journal of Pharmacology and Experminetal Therapeutics*, 266(1), (1993), 306-313.

Van Calker, D., et al., "Adenosine Regulates via Two Different Types of Receptors, the Accumulation of Cyclic Amp in Cultured Brain Cells", *Journal of Neurochemistry*, 33, (1979), 999-1005.

Van Calker, D., et al., "Carbamazepine Distinguishes Between Adenosine Receptors That Mediate Different Second Messenger Responses", *European Journal of Pharmacology*, 206 (4), (1991), 285-290.

Vittori, S, et al., "2-alkenyl and 2-alkyl derivatives of adenosine and adenosine-5'-N-ethyluronamide: different affinity and selectivity of E- and Z-diastereomers at $A_{2A}$ adenosine receptors", *Journal of Medicinal Chemistry*, 39(21), (Oct. 1996), 4211-4217.

Volpini, R., et al., "Synthesis of Di- and Tri-Substituted Adenosine Derivatives and Their Affinities at Human Adenosine Receptor Subtypes", *Nucleosides & Nucleotides*, 18 (11,12), (1999), 2511-2520.

Walker, B. A., et al., "Adenosine $A_{2a}$ Receptor Activation Delays Apoptosis in Human Neutrophils", *The American Association of Immunologists*, , (1997), 2926-2931.

Walker, D. I., et al., "Inflammatory Aneurysms of the Abdominal Aorta", *Brit. J. Surg.*, 59, (1972), 609-614.

Wan, A. A., et al., "Binding of the Adenosine $A_2$ Receptor Ligand ($^3$H)CGS 21680 to Human and Rat Brain: Evidence for Multiple Affinity Sites", *Journal of Neurochemistry*, (1990), 1763-1771.

Wolff, A. A., et al., "Ventricular Arrhythmias Parallel Cardiac Histamine Efflux After Coronary Artery Occlusion in the Dog", *Agents and Actions*, 25 (3/4), (1988), 296-306.

Yoneyama, F., "Vasodepressor Mechanisms of 2-(1-octynyl)-Adenosine (YT-146), a Selective Adenosine $A_2$ Receptor Agonist, Involve the Opening of Glibenclamide-sensitive $K^+$ Channels", *European Journal of Pharmacology*, 213 (1), (1992), 199-204.

Zablocki, J., et al., "Novel Short Acting Coronary Vasodilators That Are Functionally Selective for the A2A Receptor Based on 2-Heterocyclic Substituted Adenosine Derivatives", *Drug Development Research*, 50(1), Abstracts From Purines 2000: Biochemical, Pharmacological and Clinical Perspectives: (Abstract No. 059), (May 2000), p. 63.

"U.S. Appl. No. 09/827,083, Preliminary Amendment mailed Apr. 5, 2001", 5 pgs.

"U.S. Appl. No. 09/827,083, 312 Amendment filed Dec. 10, 2002", 2 pgs.

"U.S. Appl. No. 09/827,083, Notice of Allowance mailed Sep. 10, 2002", 6 pgs.

"U.S. Appl. No. 10/263,379, Response filed Apr. 23, 2004 to Restriction Requirement mailed Mar. 24, 2004", 2 pgs.

"U.S. Appl. No. 10/263,379, Restriction Requirement mailed Mar. 24, 2004", 4 pgs.

"U.S. Appl. No. 10/379,154, Final Office Action mailed Feb. 17, 2004", 4 pgs.

"U.S. Appl. No. 10/379,154, Final Office Action mailed Mar. 30, 2006", 5 pgs.

"U.S. Appl. No. 10/379,154, Non-Final Office Action mailed Jun. 17, 2004", 4 pgs.

"U.S. Appl. No. 10/379,154, Non-Final Office Action mailed Aug. 1, 2005", 5 pgs.

"U.S. Appl. No. 10/379,154, Non-Final Office Action mailed Aug. 8, 2003", 4 pgs.

"U.S. Appl. No. 10/379,154, Non-Final Office Action mailed Dec. 15, 2004", 5 pgs.

"U.S. Appl. No. 10/379,154, Notice of Allowance mailed Jan. 4, 2007", 5 pgs.

"U.S. Appl. No. 10/379,154, Response filed May 16, 2005 to Non-Final Office Action mailed Dec. 15, 2004", 7 pgs.

"U.S. Appl. No. 10/379,154, Response filed May 17, 2004 to Final Office Action mailed Feb. 17, 2004", 6 pgs.

"U.S. Appl. No. 10/379,154, Response filed May 31, 2006 to Final Office Action mailed Mar. 30, 2006", 7 pgs.

"U.S. Appl. No. 10/379,154, Response filed Sep. 17, 2004 to Non-Final Office Action Jun. 17, 2004", 6 pgs.

"U.S. Appl. No. 10/379,154, Response filed Nov. 6, 2003 to Non-Final Office Action mailed Aug. 8, 2003", 8 pgs.

"U.S. Appl. No. 10/379,154, Response filed Dec. 1, 2005 to Non-Final Office Action mailed Aug. 1, 2005", 7 pgs.

"U.S. Appl. No. 10/379,154, 312 Amendment filed Apr. 4, 2007", 3 pgs.

"U.S. Appl. No. 10/412,726, Examiner Interview Summary mailed Mar. 21, 2007", 3 pgs.
"U.S. Appl. No. 10/412,726, Examiner Interview Summary mailed Apr. 23, 2007", 4 pgs.
"U.S. Appl. No. 10/412,726, Examiner Interview Summary mailed Apr. 26, 2007", 4 pgs.
"U.S. Appl. No. 10/412,726, Examiner Interview Summary mailed Jul. 11, 2006", 5 pgs.
"U.S. Appl. No. 10/412,726, Non-Final Office Action mailed Apr. 16, 2010", 5 pgs.
"U.S. Appl. No. 10/412,726, Notice of Allowance mailed Mar. 12, 2009", 6 pgs.
"U.S. Appl. No. 11/196,529, Final Office Action mailed Dec. 2, 2008", 10 pgs.
"U.S. Appl. No. 11/196,529, Non-Final Office Action mailed Jun. 23, 2008", 11 pgs.
"U.S. Appl. No. 11/196,529, Notice of Allowance mailed Feb. 24, 2009", 8 pgs.
"U.S. Appl. No. 11/196,529, Preliminary Amendment filed Nov. 7, 2005", 20 pgs.
"U.S. Appl. No. 11/196,798, Non-Final Office Action mailed Sep. 17, 2008", 6 pgs.
"U.S. Appl. No. 11/196,798, Notice of Allowance mailed Feb. 24, 2009", 5 pgs.
"U.S. Appl. No. 11/196,798, Response filed Feb. 8, 2008 to Restriction Requirement mailed Jan. 9, 2008", 18 pgs.
"U.S. Appl. No. 11/196,798, Response filed Dec. 17, 2008 to Non-Final Office Action mailed Sep. 17, 2008", 17 pgs.
"U.S. Appl. No. 11/196,798, Restriction Requirement mailed Jan. 9, 2008", 6 pgs.
"U.S. Appl. No. 11/196,802, Preliminary Amendment filed Nov. 10, 2005", 16 pgs.
"U.S. Appl. No. 11/196,802, Response filed Feb. 8, 2008 to Restriction Requirement mailed Jan. 9, 2008", 16 pgs.
"U.S. Appl. No. 11/196,802, Restriction Requirement mailed Jan. 9, 2008", 6 pgs.
"U.S. Appl. No. 11/672,868, Examiner Interview Summary mailed Nov. 5, 2009", 2 pgs.
"U.S. Appl. No. 11/672,868, Preliminary Amendment mailed Feb. 12, 2008", 15 pgs.
"U.S. Appl. No. 11/673,360, Final Office Action mailed Dec. 17, 2009", 27 pgs.
"U.S. Appl. No. 11/673,360, Response filed Jun. 17, 2010 to Final Office Action mailed Dec. 17, 2009", 25 pgs.
"U.S. Appl. No. 11/691,374, Final Office Action mailed Jun. 17, 2009", 14 pgs.
"U.S. Appl. No. 11/691,374, Non Final Office Action mailed Sep. 29, 2009", 6 pgs.
"U.S. Appl. No. 11/691,374, Non-Final Office Action mailed Jan. 12, 2009", 40 pgs.
"U.S. Appl. No. 11/691,374, Notice of Allowance mailed Feb. 1, 2010", 7 pgs.
"U.S. Appl. No. 11/691,374, Preliminary Amendment filed Mar. 26, 2007", 3 pgs.
"U.S. Appl. No. 11/691,374, Preliminary Amendment filed Jun. 12, 2007", 21 pgs.
"U.S. Appl. No. 11/691,374, Response filed Apr. 13, 2009 to Non Final Office Action mailed Jan. 12, 2009", 23 pgs.
"U.S. Appl. No. 11/691,374, Response filed Aug. 17, 2009 to Final Office Action mailed Jun. 17, 2009", 14 pgs.
"U.S. Appl. No. 11/691,374, Response filed Dec. 3, 2009 to Non Final Office Action mailed Sep. 29, 2009", 16 pgs.
"U.S. Appl. No. 11/739,680, Preliminary Amendment filed Apr. 24, 2007", 3 pgs.
"U.S. Appl. No. 11/739,680, Non-Final Office Action mailed Mar. 31, 2009", 20 pgs.
"U.S. Appl. No. 11/739,680, Supplemental Preliminary Amendment filed Jul. 18, 2007", 6 pgs.
"U.S. Appl. No. 12/487,265, Non-Final Office Action mailed Dec. 18, 2009", 5 pgs.
"U.S. Appl. No. 12/487,265, Notice of Allowance mailed Apr. 6, 2010", 4 pgs.
"U.S. Appl. No. 12/487,265, Response filed Jan. 21, 2010 to Non Final Office Action mailed Dec. 18, 2009", 7 pgs.
"Argentina Application Serial No. P000100433, Response filed to Office Action mailed Oct. 20, 2008", (w/ English Translation of Claims), 9 pgs.
"Australian Application Serial No. 2002362443, Examiner's First Report mailed May 29, 2007", 4 pgs.
"Australian Application Serial No. 2002362443, Response filed May 1, 2008 to Examiner's First Report mailed May 29, 2007", 46 pgs.
"Australian Patent Application No. 2005201255, Examiner's First Report mailed Apr. 13, 2007", 2 pgs.
"Australian Patent Application No. 2005201255, Response filed Oct. 2, 2007 to Examiner's Report mailed Apr. 13, 2007", 8 pgs.
"Australian Patent Application No. 27454/00, Examiner's Report mailed Feb. 20, 2003", 1 pgs.
"Australian Patent Application No. 27454/00, Response filed Oct. 19, 2004 to Examiner's Report mailed Feb. 20, 2003", 14 pgs.
"Canadian Patent Application No. 2,361,614, Office Action mailed Jul. 20, 2007", 2 pgs.
"Canadian Patent Application No. 2,361,614, Response filed Nov. 7, 2007 to Office Action mailed Jul. 20, 2007'", 9 pgs.
"Chinese Application Serial No. 200580033215.2, Office Action mailed Mar. 16, 2010", 6 pgs.
"European Application Serial No. 02800432.3, Communication mailed Jan. 13, 2005", 3 pgs.
"European Application Serial No. 02800432.3, Communication mailed Aug. 30, 2005", 2 pgs.
"European Application Serial No. 02800432.3, Communication mailed Sep. 20, 2004", 6 pgs.
"European Application Serial No. 02800432.3, Communication mailed Oct. 16, 2006", 5 pgs.
"European Application Serial No. 02800432.3, Response filed Feb. 21, 2007 to Communication mailed Oct. 16, 2006", 19 pgs.
"European Application Serial No. 02800432.3, Response filed Nov. 1, 2005 to Communication mailed Aug. 30, 2005", 19 pgs.
"European Application Serial No. 05803845.6, Communication mailed Jul. 26, 2007", 3 pgs.
"European Application Serial No. 05803845.6, Response filed Dec. 17, 2007 to Communication mailed Jul. 26, 2007", 28 pgs.
"European Patent Application No. 00905833.0, Response filed May 14, 2003 to Communication mailed Nov. 13, 2002", 12 pgs.
"European Patent Application No. 00905833.0, Communication mailed Nov. 13, 2002", 3 pgs.
"Indian Application Serial No. 00383/KOLNP/2004, Examination Report mailed Jun. 8, 2007", 1 pg.
"Indian Application Serial No. 00383/KOLNP/2004, First Examination Report mailed Aug. 28, 2006", 2 pgs.
"Indian Application Serial No. 00383/KOLNP/2004, Response filed Mar. 6, 2007 to First Examination Report mailed Aug. 28, 2006", 33 pgs.
"Indian Application Serial No. 00383/KOLNP/2004, Response filed Aug. 2, 2007 to Examination Report mailed Jun. 8, 2007", 19 pgs.
"Indian Application Serial No. 00383/KOLNP/2004, Voluntary Amendment filed Apr. 26, 2007", 4 pgs.
"Indian Patent Application No. IN/PCT/2001/00763, First Examination Report mailed Aug. 31, 2007", 12 pgs.
"Indian Patent Application No. IN/PCT/2001/00763, Response filed Apr. 4, 2008 to First Examination Report mailed Aug. 31, 2007", 55 pgs.
"International Application Serial No. PCT/US00/02324, International Search Report mailed Oct. 20, 2000", 8 pgs.
"International Application Serial No. PCT/US00/02324, Written Opinion mailed Dec. 1, 2000", 6 pgs.
"International Application Serial No. PCT/US2005/027475, International Search Report mailed Jan. 23, 2006", 6 pgs.
"International Application Serial No. PCT/US2005/027475, Written Opinion mailed Jan. 23, 2006", 8 pgs.
"International Application Serial No. PCT/US2005/027479, International Search Report mailed Sep. 6, 2006", 6 pgs.
"International Application Serial No. PCT/US2005/027479, Written Opinion mailed Sep. 6, 2006", 10 pgs.
"International Application Serial No. No. PCT/US02/31383, International Search Report mailed May 2, 2003", 8 pgs.

"Japanese Application No. 2003-532511, Office Action mailed Apr. 28, 2009", 4 pgs.

"Japanese Application Serial No. 2007-524924, Amended Claims filed Aug. 1, 2008", (w/ English Translation of Amended Claims), 29 pgs.

"Malaysian Patent Application No. PI20000343, Response filed Mar. 7, 2005 to Substantive Examination Adverse Report mailed Dec. 7, 2004", 14 pgs.

"Malaysian Patent Application No. PI20000343, Substantive Examination Examiner's Report to the Registrar mailed Dec. 7, 2004", 2 pgs.

"New Zealand Applicaiton Serial No. 553288, Examination report mailed Mar. 19 2010", 2 pgs.

"New Zealand Application Serial No. 532062, First Examination Report mailed May 14, 2004", 1 pg.

"New Zealand Application Serial No. 532062, Response filed Feb. 9, 2006 to Second Examination Report mailed Dec. 13, 2005", 8 pgs.

"New Zealand Application Serial No. 532062, Response filed Jul. 6, 2005 to First Examination Report mailed May 14, 2004", 6 pgs.

"New Zealand Application Serial No. 532062, Second Examination Report mailed Dec. 13, 2005", 2 pgs.

"New Zealand Application Serial No. 532062, Examination Report mailed May 11, 2006", 1 pg.

"New Zealand Application Serial No. 532062, Response filed May 24, 2006 to Examination Report mailed May 11, 2006", 16 pgs.

"New Zealand Application Serial No. 545787, First Examination Report mailed Mar. 14, 2006", 2 pgs.

"New Zealand Application Serial No. 545787, Fourth Examination Report mailed Oct. 11, 2007", 2 pgs.

"New Zealand Application Serial No. 545787, Reponse filed Nov. 12, 2007 to Examination Report mailed Oct. 11, 2007", 5 pgs.

"New Zealand Application Serial No. 545787, Response filed Jul. 5, 2007 to Examination Report mailed Jan. 11, 2007", 5 pgs.

"New Zealand Application Serial No. 545787, Response filed Aug. 14, 2007 to Examination Report mailed Jul. 11, 2007", 11 pgs.

"New Zealand Application Serial No. 545787, Response filed Dec. 13, 2006 to Examination Report mailed Mar. 14, 2006", 21 pgs.

"New Zealand Application Serial No. 545787, Second Examination Report mailed Jan. 11, 2007", 4 pgs.

"New Zealand Application Serial No. 545787, Third Examination Report mailed Jul. 11, 2007", 2 pgs.

"New Zealand Application Serial No. 553288, Response filed Mar. 5, 2010 to Examination Report mailed Apr. 29, 2009", 34 pgs.

"New Zealand Application Serial No. 553288, Response filed Mar. 23, 2010 to Examination Report mailed Mar. 19, 2010", 4 pgs.

"New Zealand Application Serial No. 553288, Response filed May 26, 2010 to Examination Report mailed Apr. 12, 2010", 5 pgs.

"New Zealand Application Serial No. 553288, Subsequent Examiners Report mailed Apr. 12, 2010", 2 Pgs.

"New Zealand Application Serial No. 556354, Response filed Jul. 4, 2008 to Examination Report mailed Jul. 11, 2007", 22 pgs.

"New Zealand Application Serial No. 556354, First Examination Report mailed Jul. 11, 2007", 21 pgs.

"New Zealand Application Serial No. 556354, Response filed Sep. 10, 2008 to Examination Report mailed Jul. 17, 2008", 12 pgs.

"New Zealand Application Serial No. 556354, Second Examination Report mailed Jul. 17, 2008", 1 pg.

"Norweigan Application Serial No. 20013507, Office Action mailed Oct. 24, 2005", (w/ English Translation), 10 pgs.

"Norweigan Application Serial No. 20013507, Response filed Feb. 6, 2006 to Office Action mailed Oct. 24, 2005", 94 pgs.

"Norweigan Application Serial No. 20013507, Response filed Apr. 26, 2005 to Office Action mailed Nov. 2, 2004", 16 pgs.

"Norweigan Application Serial No. 20013507, Response filed Oct. 17, 2005 to Office Action mailed Jun. 1, 2005", 23 pgs.

"Norweigan Patent Application No. 20013507, Office Action mailed Jun. 1, 2005", 3 pgs.

"Norweigan Patent Application No. 20013507, Office Action mailed Nov. 2, 2004", 5 pgs.

"Russian Application Serial No. 2001124348, Official Action mailed Sep. 29, 2003", (w/ English Translation), 9 pgs.

"Russian Application Serial No. 2001124348, Response filed Jan. 30, 2004 to Official Action mailed Sep. 29, 2003", (w/ English Translation of Claims), 48 pgs.

"Singapore Application Serial No. 200401458-5, Invitation to Respond to Written Opinion mailed Nov. 17, 2006", 12 pgs.

"Singapore Application Serial No. 200401458-5, Response filed Apr. 16, 2007 to Invitation to Respond to Written Opinion mailed Nov. 17, 2006", 30 pgs.

Entman, M. L., et al., "Inflammation in the course of early myocardial ischemia", *FASEB Journal*, vol. 5, (1991), 2529-2537.

"U.S. Appl. No. 12/712,022, Non-Final Office Action mailed Nov. 9, 2010", 53 pgs.

"U.S. Appl. No. 12/712,022, Response filed Feb. 7, 2011 to Non Final Office Action mailed Nov. 9, 2010", 27 pgs.

"European Application Serial No. 05803845.6, Response filed Feb. 9, 2011 to Non Final Office Action mailed Oct. 19, 2010", 3 pgs.

"European Application Serial No. 10181920.9, Extended European Search Report mailed Nov. 30, 2010", 11 pgs.

"U.S. Appl. No. 12/487,265, Notice of Allowance mailed Sep. 7, 2010", 6 pgs.

"Chinese Application Serial No. 200580033215.2, Office Action Response Filed Aug. 2, 2010", 34 pgs.

"New Zealand Application Serial No. 585697,First Examiner Report mailed Jun. 3, 2010", 2 Pgs.

* cited by examiner

2-PROPYNYL ADENOSINE ANALOGS WITH MODIFIED 5'-RIBOSE GROUPS HAVING A2A AGONIST ACTIVITY

RELATED APPLICATIONS

This application is a continuation of U.S. patent application entitled: "2-PROPYNYL ADENOSINE ANALOGS WITH MODIFIED 5'-RIBOSE GROUPS HAVING $A_{2A}$ AGONIST ACTIVITY", filed Aug. 2, 2005, Ser. No. 11/196,529, now U.S. Pat. No. 7,605,143 which claims priority from a provisional application entitled: "2-PROPYNYL ADENOSINE ANALOGS and COMPOSITIONS WITH MODIFIED 5'-RIBOSE GROUPS HAVING $A_{2A}$ AGONIST ACTIVITY", filed on Aug. 2, 2004, Ser. No. 60/598,018, the entire contents of which are included herein by reference in their entirety.

GOVERNMENT FUNDING

The invention described herein was made with government support under Grant Number (RO1-HL37942), awarded by the National Institutes of Health. The United States Government has certain rights in the invention.

BACKGROUND OF THE INVENTION

The inflammatory response serves the purpose of eliminating harmful agents from the body. There is a wide range of pathogenic insults that can initiate an inflammatory response including infection, allergens, autoimmune stimuli, immune response to transplanted tissue, noxious chemicals, and toxins, ischemia/reperfusion, hypoxia, mechanical and thermal trauma. Inflammation normally is a very localized action, which serves in expulsion, attenuation by dilution, and isolation of the damaging agent and injured tissue. The body's response becomes an agent of disease when it results in inappropriate injury to host tissues in the process of eliminating the targeted agent, or responding to a traumatic insult.

As examples, inflammation is a component of pathogenesis in several vascular diseases or injuries. Examples include: ischemia/reperfusion injury (N. G. Frangogiannis et al., in Myocardial Ischemia: Mechanisms, Reperfusion, Protection, M. Karmazyn, ed., Birkhuser Verlag (1996) at 236-284; H. S. Sharma et al., Med. of Inflamm., 6, 175 (1987)), atherosclerosis (R. Ross, Nature, 362, 801 (1993)), inflammatory aortic aneurysms (N. Girardi et al., Ann. Thor. Surg., 64, 251 (1997); D. I. Walker et al., Brit. J. Surg., 59, 609 (1972); R. L. Pennell et al., J. Vasc. Surg., 2, 859 (1985)), and restenosis following balloon angioplasty (see, R. Ross cited above). The cells involved with inflammation include leukocytes (i.e., the immune system cells—neutrophils, eosinophils, lymphocytes, monocytes, basophils, macrophages, dendritic cells, and mast cells), the vascular endothelium, vascular smooth muscle cells, fibroblasts, and myocytes.

The release of inflammatory cytokines such as tumor necrosis factor-alpha (TNFα) by leukocytes is a means by which the immune system combats pathogenic invasions, including infections. TNFα stimulates the expression and activation of adherence factors on leukocytes and endothelial cells, primes neutrophils for an enhanced inflammatory response to secondary stimuli and enhances adherent neutrophil oxidative activity. See, Sharma et al., cited herein. In addition, macrophages/dendritic cells act as accessory cells processing antigen for presentation to lymphocytes. The lymphocytes, in turn, become stimulated to act as pro-inflammatory cytotoxic cells.

Generally, cytokines stimulate neutrophils to enhance oxidative (e.g., superoxide and secondary products) and non-oxidative (e.g., myeloperoxidase and other enzymes) inflammatory activity. Inappropriate and over-release of cytokines can produce counterproductive exaggerated pathogenic effects through the release of tissue-damaging oxidative and non-oxidative products (K. G. Tracey et al., J. Exp. Med., 167, 1211 (1988); and D. N. Mannel et al., Rev. Infect. Dis., 9 (suppl. 5), S602-S606 (1987)). For example, TNFα can induce neutrophils to adhere to the blood vessel wall and then to migrate through the vessel to the site of injury and release their oxidative and non-oxidative inflammatory products.

Although monocytes collect slowly at inflammatory foci, given favorable conditions, the monocytes develop into long-term resident accessory cells and macrophages. Upon stimulation with an inflammation trigger, monocytes/macrophages also produce and secrete an array of cytokines (including TNFα), complement, lipids, reactive oxygen species, proteases and growth factors that remodel tissue and regulate surrounding tissue functions.

For example, inflammatory cytokines have been shown to be pathogenic in: arthritis (C. A. Dinarello, Semin. Immunol., 4, 133 (1992)); ischemia (A. Seekamp et al., Agents-Actions-Supp., 41, 137 (1993)); septic shock (D. N. Mannel et al., Rev. Infect. Dis., 9 (suppl. 5), S602-S606 (1987)); asthma (N. M. Cembrzynska et al., Am. Rev. Respir. Dis., 147, 291 (1993)); organ transplant rejection (D. K. Imagawa et al., Transplantation, 51, 57 (1991); multiple sclerosis (H. P. Hartung, Ann. Neurol., 33, 591 (1993)); AIDS (T. Matsuyama et al., AIDS, 5, 1405 (1991)); and in alkali-burned eyes (F. Miyamoto et al., Opthalmic Res., 30, 168 (1997)). In addition, superoxide formation in leukocytes has been implicated in promoting replication of the human immunodeficiency virus (HIV) (S. Legrand-Poels et al., AIDS Res. Hum. Retroviruses, 6, 1389 (1990)).

It is well known that adenosine and some analogs of adenosine that non-selectively activate adenosine receptor subtypes decrease neutrophil production of inflammatory oxidative products (B. N. Cronstein et al., Ann. N.Y. Acad. Sci., 451, 291 (1985); P. A. Roberts et al., Biochem. J., 227, 669 (1985); D. J. Schrier et al., J. Immunol., 137, 3284 (1986); B. N. Cronstein et al., Clinical Immunol. and Immunopath., 42, 76 (1987); M. A. Iannone et al., in Topics and Perspective in Adenosine Research, E. Gerlach et al., eds., Springer-Verlag, Berlin, p. 286 (1987); S. T. McGarrity et al., J. Leukocyte Biol., 44, 411-421 (1988); J. De La Harpe et al., J. Immunol., 143, 596 (1989); S. T. McGarrity et al., J. Immunol., 142, 1986 (1989); and C. P. Nielson et al., Br. J. Pharmacol., 97, 882 (1989)). For example, adenosine has been shown to inhibit superoxide release from neutrophils stimulated by chemoattractant such as the synthetic mimic of bacterial peptides, f-met-leu-phe (fMLP), and the complement component $C_5a$ (B. N. Cronstein et al., J. Immunol., 135, 1366 (1985)). Adenosine can decrease the greatly enhanced oxidative burst of PMN (neutrophil) first primed with TNF-α and then stimulated by a second stimulus such as f-met-leu-phe (G. W. Sullivan et al., Clin. Res., 41, 172A (1993)). Additionally, it has been reported that adenosine can decrease the rate of HIV replication in a T-cell line (S. Sipka et al., Acta. Biochim. Biopys. Hung., 23, 75 (1988)). However, there is no evidence that in vivo adenosine has anti-inflammatory activity (G. S. Firestein et al., Clin. Res., 41, 170A (1993); and B. N. Cronstein et al., Clin. Res., 41, 244A (1993)).

It has been suggested that there is more than one subtype of adenosine receptor on neutrophils that can have opposite effects on superoxide release (B. N. Cronstein et al., J. Clin. Invest., 85, 1150 (1990)). The existence of $A_{2A}$ receptor on neutrophils was originally demonstrated by Van Calker et al. (D. Van Calker et al., Eur. J. Pharmacology, 206, 285 (1991)).

There has been progressive development of compounds that are more and more potent and/or selective as agonists of $A_{2A}$ adenosine receptors (AR) based on radioligand binding assays and physiological responses. Initially, compounds with little or no selectivity for $A_{2A}$ receptors were developed, such as adenosine itself or 5'-carboxamides of adeno sine, such as 5'-N-ethylcarboxamidoadeno sine (NECA) (B. N. Cronstein et al., J. Immunol., 135, 1366 (1985)). Later, it was shown that addition of 2-alkylamino substituents increased potency and selectivity, e.g., CV1808 and CGS21680 (M. F. Jarvis et al., J. Pharmacol. Exp. Ther., 251, 888 (1989)). 2-Alkoxy-substituted adenosine derivatives such as WRC-0090 are even more potent and selective as agonists at the coronary artery $A_{2A}$ receptor (M. Ueeda et al., J. Med. Chem., 34, 1334 (1991)). The 2-alklylhydrazino adenosine derivatives, e.g., SHA 211 (also called WRC-0474) have also been evaluated as agonists at the coronary artery $A_{2A}$ receptor (K. Niiya et al., J. Med. Chem., 35, 4557 (1992)).

There is one report of the combination of relatively non-specific adenosine analogs, R-phenylisopropyladenosine (R-PIA) and 2-chloroadenosine (Cl-Ado) with a phosphodiesterase (PDE) inhibitor resulting in a lowering of neutrophil oxidative activity (M. A. Iannone et al., Topics and Perspectives in Adenosine Research, E. Garlach et al., eds., Springer-Verlag, Berlin, pp. 286-298 (1987)). However, R-PIA and Cl-Ado analogs are actually more potent activators of $A_1$ adenosine receptors than of $A_{2A}$ adenosine receptors and, thus, are likely to cause side effects due to activation of $A_1$ receptors on cardiac muscle and other tissues causing effects such as "heart block."

R. A. Olsson et al. (U.S. Pat. No. 5,278,150) disclose selective adenosine $A_2$ receptor agonists of the formula:

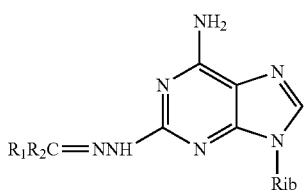

wherein Rib is ribosyl, $R_1$ can be H and $R_2$ can be cycloalkyl. The compounds are disclosed to be useful for treating hypertension, atherosclerosis and as vasodilators.

Olsson et al. (U.S. Pat. No. 5,140,015) disclose certain adenosine $A_2$ receptor agonists of formula:

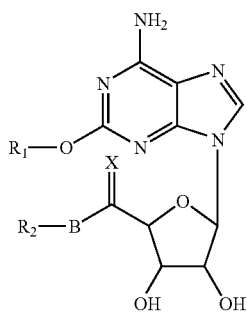

wherein C(X) $BR_2$ can be $CH_2OH$ and $R_1$ can be alkyl- or alkoxyalkyl. The compounds are disclosed to be useful as vasodilators or an antihypertensives.

Linden et al. (U.S. Pat. No. 5,877,180) is based on the discovery that certain inflammatory diseases, such as arthritis and asthma, may be effectively treated by the administration of compounds which are selective agonists of $A_{2A}$ adenosine receptors, preferably in combination with a Type IV phosphodiesterase inhibitor. An embodiment of the Linden et al. invention provides a method for treating inflammatory diseases by administering an effective amount of an $A_{2A}$ adenosine receptor of the following formula:

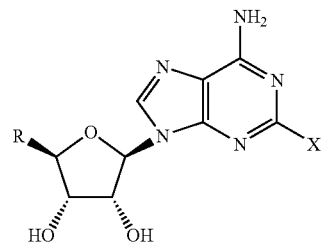

wherein R and X are as described in the patent.

In one embodiment, the Linden et al. invention involves the administration of a Type IV phosphodiesterase (PDE) inhibitor in combination with the $A_{2A}$ adenosine receptor agonist. The Type IV phosphodiesterase (PDE) inhibitor includes racemic and optically active 4-(polyalkoxyphenyl)-2-pyrrolidones of the following formula:

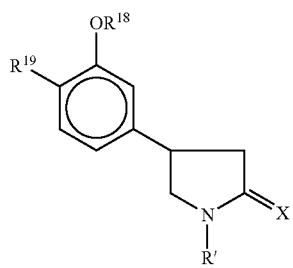

wherein RN, $R^{18}$, $R^{19}$ and X are as disclosed and described in U.S. Pat. No. 4,193,926. Rolipram is an example of a suitable Type IV PDE inhibitor included within the above formula.

G. Cristalli (U.S. Pat. No. 5,593,975) discloses 2-arylethynyl, 2-cycloalkylethynyl or 2-hydroxyalkylethynyl derivatives, wherein the riboside residue is substituted by carboxy amino, or substituted carboxy amino ($R_3HNC(O)$—). 2-Alkynylpurine derivatives have been disclosed in Miyasaka et al. (U.S. Pat. No. 4,956,345), wherein the 2-alkynyl group is substituted with ($C_3$-$C_{16}$)alkyl. The '975 compounds are disclosed to be vasodilators and to inhibit platelet aggregation, and thus to be useful as anti-ischemic, anti-atherosclerosis and anti-hypertensive agents.

Recently, U.S. Pat. No. 6,232,297 to Linden, et al. disclosed compounds having the general formula:

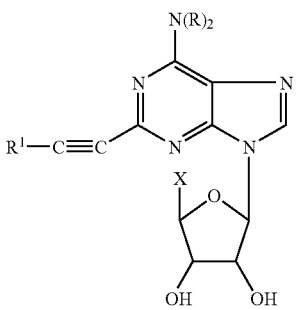

wherein each R is H, X is ethylaminocarbonyl and $R^1$ is 4-carboxycyclo-hexylmethyl (DWH-146a), $R^1$ is 4-methoxycarbonylcyclohexylmethyl (DWH-146e) or R is 4-acetoxymethyl-cyclohexylmethyl (JMR-193). These compounds are reported to be $A_{2A}$ agonists.

However, a continuing need exists for selective $A_2$ adenosine receptor agonists useful for therapeutic applications, which have reduced side effects. In addition, a continuing need exists for selective A2 adenosine receptor agonists useful for use as pharmacological stressors in stress imaging or in other ventricular function imaging techniques, that preferably have reduced side effects, while being chemically stable and short-acting.

SUMMARY OF THE INVENTION

The present invention comprises compounds and methods of their use for the treatment of inflammatory activity in mammalian tissue. The inflammatory tissue activity can be due to pathological agents or can be due to physical, chemical or thermal trauma, or the trauma of medical procedures, such as organ, tissue or cell transplantation, angioplasty (PCTA), inflammation following ischemia/reperfusion, or grafting. The present compounds comprise a novel class of 2-alkynyladenosine derivatives, substituted at the ethyn-2-yl position by substituted cycloalkyl and heterocycle (heterocyclic) moieties. Preferably, the riboside residue is modified at the 5'-position by substituting an N-(cycloalkyl)carboxyamino ("aminocarbonyl") moiety ("X") or a 5- or 6-membered heterocyclic ring. Thus, the present invention provides a method for inhibiting the inflammatory response in a mammal, such as a human subject, and protecting the tissue subject to the response, by administering an effective amount of one or more compounds of the invention.

The compounds of the invention have general formula (I):

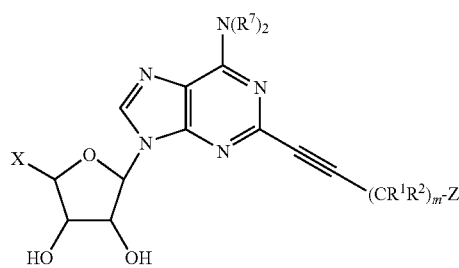

(I)

wherein
Z is $CR^3R^4R^5$ or $NR^4R^5$;

each $R^1$ is independently hydrogen, halo, —$OR^a$, —$SR^a$, ($C_1$-$C_8$)alkyl, cyano, nitro, trifluoromethyl, trifluoromethoxy, $C_{3-8}$cycloalkyl, heterocycle, heterocycle($C_1$-$C_8$)alkylene-, aryl, aryl($C_1$-$C_8$)alkylene-, heteroaryl, heteroaryl($C_1$-$C_8$)alkylene-, —$CO_2R^a$, $R^aC(=O)O$—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$—, —$OPO_3R^a$, $R^aOC(=S)$—, $R^aC(=S)$—, —$SSR^a$, $R^aS(=O)$—, $R^aS(=O)_2$—, —N=$NR^a$, or —$OPO_2R^a$;

each $R^2$ is independently hydrogen, halo, ($C_1$-$C_8$)alkyl, ($C_3$-$C_8$)cycloalkyl, heterocycle, heterocycle($C_1$-$C_8$)alkylene-, aryl, aryl($C_1$-$C_8$)alkylene-, heteroaryl, or heteroaryl ($C_1$-$C_8$)alkylene-; or $R^1$ and $R^2$ and the atom to which they are attached is C=O, C=S or C=$NR^c$.

$R^4$ and $R^5$ together with the atoms to which they are attached form a saturated or partially unsaturated, or aromatic ring having 3, 4, 5, 6, 7, 8, 9 or 10 ring atoms optionally comprising 1, 2, 3, or 4 heteroatoms selected from non-peroxide oxy (—O—), thio (—S—), sulfinyl (—SO—), sulfonyl (—S(O)$_2$—) or amine (—$NR^a$) in the ring;

wherein any ring comprising $R^4$ and $R^5$ is substituted with from 1 to 14 $R^6$ groups;

wherein each $R^6$ is independently hydrogen, halo, —$OR^a$, —$SR^a$, ($C_1$-$C_8$)alkyl, cyano, nitro, trifluoromethyl, trifluoromethoxy, ($C_1$-$C_8$)cycloalkyl, ($C_1$-$C_8$)cycloalkyl($C_1$-$C_8$) alkylene-, ($C_6$-$C_{12}$)bicycloalkyl, heterocycle or heterocycle ($C_1$-$C_8$)alkylene-, aryl, aryl($C_1$-$C_8$)alkylene-, heteroaryl, heteroaryl($C_1$-$C_8$)alkylene-, $CO_2R^a$, $R^aC(=O)O$—, $R^aC(=O)$, —$OC_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$—, $OPO_3R^a$, $R^aOC(=S)$—, $R^aC(=S)$—, —$SSR^a$, $R^aS(=O)$—, —$NNR^a$, —$OPO_2R^a$, or two $R^6$ groups and the atom to which they are attached is C=O, or C=S; or two $R^6$ groups together with the atom or atoms to which they are attached can form a carbocyclic or a heterocyclic ring comprising from 1 to 6 carbon atoms and 1, 2, 3, or 4 heteroatoms selected from non-peroxide oxy (—O—), thio (—S—), sulfinyl (—SO—), sulfonyl (—S(O)$_2$—), phosphine (—OP(O)$_2$—, or amine (—$NR^a$) in the ring;

$R^3$ is hydrogen, halo, —$OR^a$, —$SR^a$, ($C_1$-$C_8$)alkyl, cyano, nitro, trifluoromethyl, trifluoromethoxy, ($C_3$-$C_8$)cycloalkyl, ($C_1$-$C_8$)cycloalkyl-($C_1$-$C_8$)alkylene-, heterocycle, heterocycle($C_1$-$C_8$)alkylene-, aryl, aryl($C_1$-$C_8$)alkylene-, heteroaryl, heteroaryl($C_1$-$C_8$)alkylene-, —$CO_2R^a$, $R^aC(=O)$O—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$, —$OPO_3R^a$, $R^aOC(=S)$—, $R^aC(=S)$—, —$SSR^a$, $R^aS(=O)$—, $R^aS(=O)_2$—, —$NNR^a$, —$OPO_2R^a$; or if the ring formed from $CR^4R^5$ is aryl or heteroaryl or partially unsaturated then $R^3$ can be absent;

each $R^7$ is independently hydrogen, ($C_1$-$C_8$)alkyl, ($C_3$-$C_8$) cycloalkyl, ($C_1$-$C_8$)cycloalkyl($C_1$-$C_8$)alkylene-, heterocycle, heterocycle ($C_1$-$C_8$)alkylene-, aryl, aryl($C_1$-$C_8$)alkylene, heteroaryl, or heteroaryl($C_1$-$C_8$)alkylene-;

X is —$CH_2OR^e$, —$CO_2R^e$, —$CH_2OC(O)R^e$, —$C(O)NR^eR^f$, —$CH_2SR^e$, —$C(S)OR^e$, —$CH_2OC(S)R^e$ or $C(S)NR^eR^f$, —$CH_2N(R^e)(R^f)$, or a group having the formula

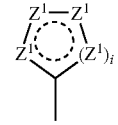

wherein each $Z^1$ is non-peroxide —O—, —S(O)$_p$—, —C($R^8$)$_j$—, or —N($R^8$)—;

provided that at least one $Z^1$ is non-peroxide —O—, —S(O)$_p$—, or —N($R^8$)—;

each $R^8$ is independently hydrogen, ($C_1$-$C_8$)alkyl, ($C_1$-$C_8$) alkenyl, ($C_3$-$C_8$)cycloalkyl, ($C_1$-$C_8$)alkyl($C_3$-$C_8$)cycloalkyl, ($C_3$-$C_8$)cycloalkenyl, ($C_1$-$C_8$)alkyl($C_3$-$C_8$)cycloalkenyl, aryl, aryl($C_1$-$C_8$)alkylene, heteroaryl, or heteroaryl($C_1$-$C_8$) alkylene-; wherein any of the alkyl or alkenyl groups of $R^8$ are optionally interrupted by —O—, —S—, or —N($R^a$)—;

$R^e$ is cyclopropyl, cyclobutyl, cyclopentyl, cyclohexyl;

$R^f$ is hydrogen, ($C_1$-$C_8$)alkyl, or ($C_1$-$C_8$)alkyl substituted with 1-3 ($C_1$-$C_8$)alkoxy, ($C_3$-$C_8$)cycloalkyl, ($C_1$-$C_8$)alkylthio, amino acid, aryl, aryl($C_1$-$C_8$)alkylene, heteroaryl, or heteroaryl($C_1$-$C_8$)alkylene; and wherein any of the alkyl, alkenyl, cycloalkyl, cycloalkenyl, heterocycle, aryl, or heteroaryl, groups of $R^1$, $R^2$, $R^3$, $R^6$, $R^7$ and $R^8$ is optionally substituted on carbon with one or more (e.g. 1, 2, 3, or 4) substituents selected from the group consisting of halo, —$OR^a$, —$SR^a$, ($C_1$-$C_8$)alkyl, cyano, nitro, trifluoromethyl, trifluoromethoxy, ($C_3$-$C_8$)cycloalkyl, ($C_6$-$C_{12}$)bicycloalkyl, heterocycle or heterocycle($C_1$-$C_8$)alkylene-, aryl, aryloxy, aryl($C_1$-$C_8$)alkylene-, heteroaryl, heteroaryl($C_1$-$C_8$)alkylene-, —$CO_2R^a$, $R^aC$(=O)O—, $R^aC$(=O)—, —$OCO_2R^a$, $R^aR^bNC$(=O)O—, $R^bOC$(=O)N($R^a$)—, $R^aR^bN$—, $R^aR^bNC$(=O)—, $R^aC$(=O)N($R^b$)—, $R^aR^bNC$(=O)N($R^b$)—, $R^aR^bNC$(=S)N($R^b$)—, —$OPO_3R^a$, $R^aOC$(=S)—, $R^aC$(=S), —$SSR^a$, $R^aS$(=O)$_p$—, $R^aR^bNS$(O)$_p$—, N=$NR^a$, and —$OPO_2R^a$;

wherein any ($C_1$-$C_8$)alkyl, ($C_3$-$C_8$)cycloalkyl, ($C_6$-$C_{12}$)bicycloalkyl, ($C_1$-$C_8$)alkoxy, ($C_1$-$C_8$)alkanoyl, ($C_1$-$C_8$)alkylene, or heterocycle, is optionally partially unsaturated;

$R^a$ and $R^b$ are each independently hydrogen, ($C_1$-$C_{18}$)alkyl, or ($C_1$-$C_{18}$)alkyl substituted with 1-3 ($C_1$-$C_{18}$)alkoxy, ($C_3$-$C_8$)cycloalkyl, ($C_1$-$C_{18}$)alkylthio, amino acid, aryl, aryl($C_1$-$C_{18}$)alkylene, heteroaryl, or heteroaryl($C_1$-$C_{18}$)alkylene; or $R^a$ and $R^b$, together with the nitrogen to which they are attached, form a pyrrolidino, piperidino, morpholino, or thiomorpholino ring; and $R^c$ is hydrogen or ($C_1$-$C_6$)alkyl;

m is 0, 1, 2, 3, 4, 5, 6, 7, or 8; i is 1, or 2; each j is independently 1, or 2; and each p is independently 0, 1, or 2; or a pharmaceutically acceptable salt thereof.

In another embodiment, the compounds of the invention have general formula (I):

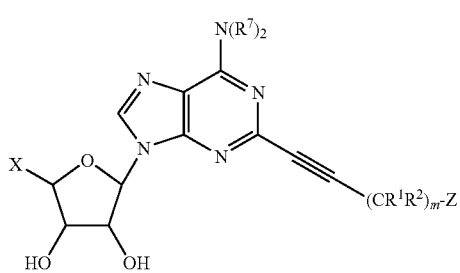

(I)

wherein

Z is $CR^3R^4R^5$ or $NR^4R^5$;

each $R^1$ is independently hydrogen, halo, —$OR^a$, —$SR^a$, ($C_1$-$C_8$)alkyl, cyano, nitro, trifluoromethyl, trifluoromethoxy, $C_{3-8}$cycloalkyl, heterocycle, heterocycle($C_1$-$C_8$)alkylene-, aryl, aryl($C_1$-$C_8$)alkylene-, heteroaryl, heteroaryl($C_1$-$C_8$)alkylene-, —$CO_2R^a$, $R^aC$(=O)O—, $R^aC$(=O)—, —$OCO_2R^a$, $R^aR^bNC$(=O)O—, $R^bOC$(=O)N($R^a$)—, $R^aR^bN$—, $R^aR^bNC$(=O)—, $R^aC$(=O)N($R^b$)— $R^aR^bNC$(=O)N($R^b$)—, $R^aR^bNC$(=S)N($R^b$)—, —$OPO_3R^a$, $R^aOC$(=S)—, $R^aC$(=S)—, —$SSR^a$, $R^aS$(=O)—, $R^aS$(=O)$_2$—, —N=$NR^a$, or —$OPO_2R^a$;

each $R^2$ is independently hydrogen, halo, ($C_1$-$C_8$)alkyl, ($C_3$-$C_8$)cycloalkyl, heterocycle, heterocycle($C_1$-$C_8$)alkylene-, aryl, aryl($C_1$-$C_8$)alkylene-, heteroaryl, or heteroaryl($C_1$-$C_8$)alkylene-; or $R^1$ and $R^2$ and the atom to which they are attached is C=O, C=S or C=$NR^c$.

$R^4$ and $R^5$ together with the atoms to which they are attached form a saturated or partially unsaturated, or aromatic ring having 3, 4, 5, 6, 7, 8, 9 or 10 ring atoms optionally comprising 1, 2, 3, or 4 heteroatoms selected from non-peroxide oxy (—O—), thio (—S—), sulfinyl (—SO—), sulfonyl (—S(O)$_2$—) or amine (—$NR^a$—) in the ring;

wherein any ring comprising $R^4$ and $R^5$ is substituted with from 1 to 14 $R^6$ groups;

wherein each $R^6$ is independently hydrogen, halo, —$OR^a$, —$SR^a$, ($C_1$-$C_8$)alkyl, cyano, nitro, trifluoromethyl, trifluoromethoxy, ($C_1$-$C_8$)cycloalkyl, ($C_1$-$C_8$)cycloalkyl($C_1$-$C_8$)alkylene-, ($C_6$-$C_{12}$)bicycloalkyl, heterocycle or heterocycle($C_1$-$C_8$)alkylene-, aryl, aryl($C_1$-$C_8$)alkylene-, heteroaryl, heteroaryl($C_1$-$C_8$)alkylene-, $CO_2R^a$, $R^aC$(=O)O—, $R^aC$(=O), —$OC_2R^a$, $R^aR^bNC$(=O)O—, $R^bOC$(=O)N($R^a$)—, $R^aR^bN$—, $R^aR^bNC$(=O)—, $R^aC$(=O)N($R^b$)—, $R^aR^bNC$(=O)N($R^a$)—, $R^aR^bNC$(=S)N($R^a$)—, —$OPO_3R^a$, $R^aOC$(=S)—, $R^aC$(=S)—, —$SSR^a$, $R^aS$(=O)—, —N$NR^a$, —$OPO_2R^a$, or two $R^6$ groups and the atom to which they are attached is C=O, or C=S; or two $R^6$ groups together with the atom or atoms to which they are attached can form a carbocyclic or a heterocyclic ring comprising from 1 to 6 carbon atoms and 1, 2, 3, or 4 heteroatoms selected from non-peroxide oxy (—O—), thio (—S—), sulfinyl (—SO—), sulfonyl (—S(O)$_2$—), phosphine (—OP(O)$_2$—, or amine (—$NR^a$—) in the ring;

$R^3$ is hydrogen, halo, —$OR^a$, —$SR^a$, ($C_1$-$C_8$)alkyl, cyano, nitro, trifluoromethyl, trifluoromethoxy, ($C_3$-$C_8$)cycloalkyl, ($C_1$-$C_8$)cycloalkyl-($C_1$-$C_8$)alkylene-, heterocycle, heterocycle($C_1$-$C_8$)alkylene-, aryl, aryl($C_1$-$C_8$)alkylene-, heteroaryl, heteroaryl($C_1$-$C_8$)alkylene-, —$CO_2R^a$, $R^aC$(=O)O—, $R^aC$(=O)—, —$OCO_2R^a$, $R^aR^bNC$(=O)O—, $R^bOC$(=O)N($R^a$)—, $R^aR^bN$—, $R^aR^bNC$(=O)—, $R^aC$(=O)N($R^b$)—, $R^aR^bNC$(=O)N($R^b$)—, $R^aR^bNC$(=S)N($R^b$), —$OPO_3R^a$, $R^aOC$(=S)—, $R^aC$(=S)—, —$SSR^a$, $R^aS$(=O)—, $R^aS$(=O)$_2$—, —$NNR^a$, —$OPO_2R^a$; or if the ring formed from $CR^4R^5$ is aryl or heteroaryl or partially unsaturated then $R^3$ can be absent;

each $R^7$ is independently hydrogen, ($C_1$-$C_8$)alkyl, ($C_3$-$C_8$)cycloalkyl, ($C_1$-$C_8$)cycloalkyl($C_1$-$C_8$)alkylene-, heterocycle, heterocycle ($C_1$-$C_8$)alkylene-, aryl, aryl($C_1$-$C_8$)alkylene, heteroaryl, or heteroaryl($C_1$-$C_8$)alkylene-;

X is —$CH_2OR^e$, —$CO_2R^e$, —$CH_2OC(O)R^e$, —$C(O)NR^eR^f$, —$CH_2SR^e$, —$C(S)OR^e$, —$CH_2OC(S)R^e$ or $C(S)NR^eR^f$, —$CH_2N(R^e)(R^f)$, or a group having the formula

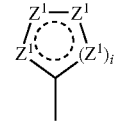

wherein each $Z^1$ is non-peroxide —O—, —S(O)$_p$—, —$C(R^8)_j$—, or —$N(R^8)$—; provided that at least one $Z^1$ is non-peroxide —O—, —S(O)$_p$—, or —$N(R^8)$—;

each $R^8$ is independently hydrogen, ($C_1$-$C_8$)alkyl, ($C_1$-$C_8$)alkenyl, ($C_3$-$C_8$)cycloalkyl, ($C_1$-$C_8$)alkyl($C_3$-$C_8$)cycloalkyl, ($C_3$-$C_8$)cycloalkenyl, ($C_1$-$C_8$)alkyl($C_3$-$C_8$)cycloalkenyl, aryl, aryl($C_1$-$C_8$)alkylene, heteroaryl, or heteroaryl($C_1$-$C_8$)alkylene-; wherein any of the alkyl or alkenyl groups of $R^8$ are optionally interrupted by —O—, —S—, or —N($R^a$)—;

$R^e$ is cyclopropyl, cyclobutyl, cyclopentyl, cyclohexyl;

$R^f$ is hydrogen, ($C_1$-$C_8$)alkyl, or ($C_1$-$C_8$)alkyl substituted with 1-3 ($C_1$-$C_8$)alkoxy, ($C_3$-$C_8$)cycloalkyl, ($C_1$-$C_8$)alkylthio, amino acid, aryl, aryl($C_1$-$C_8$)alkylene, heteroaryl, or heteroaryl($C_1$-$C_8$)alkylene; and wherein any of the alkyl, alkenyl, cycloalkyl, cycloalkenyl, heterocycle, aryl, or heteroaryl, groups of $R^1$, $R^2$, $R^3$, $R^6$, $R^7$ and $R^8$ is optionally substituted on carbon with one or more (e.g. 1, 2, 3, or 4) substituents selected from the group consisting of halo, —OR$^a$, —SR$^a$, (C$_1$-C$_8$)alkyl, cyano, nitro, trifluoromethyl, trifluoromethoxy, (C$_3$-C$_8$)cycloalkyl, (C$_6$-C$_{12}$)bicycloalkyl, heterocycle or heterocycle(C$_1$-C$_8$)alkylene-, aryl, aryloxy, aryl(C$_1$-C$_8$)alkylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—R$^a$R$^b$NC(=O)N(R$^b$)—, R$^a$R$^b$NC(=S)N(R$^b$)—, —OPO$_3$R$^a$, R$^a$OC(=S)—, R$^a$C(=S), —SSR$^a$, R$^a$S(=O)$_p$—, R$^a$R$^b$NS(O)$_p$—, N=NR$^a$, and —OPO$_2$R$^a$;

wherein any (C$_1$-C$_8$)alkyl, (C$_3$-C$_8$)cycloalkyl, (C$_6$-C$_{12}$)bicycloalkyl, (C$_1$-C$_8$)alkoxy, (C$_1$-C$_8$)alkanoyl, (C$_1$-C$_8$)alkylene, or heterocycle, is optionally partially unsaturated;

R$^a$ and R$^b$ are each independently hydrogen, (C$_1$-C$_8$)alkyl, or (C$_1$-C$_8$)alkyl substituted with 1-3 (C$_1$-C$_8$)alkoxy, (C$_3$-C$_8$)cycloalkyl, (C$_1$-C$_8$)alkylthio, amino acid, aryl, aryl(C$_1$-C$_8$)alkylene, heteroaryl, or heteroaryl(C$_1$-C$_8$)alkylene; or R$^a$ and R$^b$, together with the nitrogen to which they are attached, form a pyrrolidino, piperidino, morpholino, or thiomorpholino ring; and R$^c$ is hydrogen or (C$_1$-C$_6$)alkyl;

m is 0, 1, 2, 3, 4, 5, 6, 7, or 8; i is 1, or 2; each j is independently 1, or 2; and each p is independently 0, 1, or 2; or a pharmaceutically acceptable salt thereof.

The invention provides a compound of formula I for use in medical therapy, preferably for use in treating inflammation or protecting mammalian tissue from inflammation such as an inflammatory response, e.g., resulting from allergy, trauma or ischemia/reperfusion injury, as well as the use of a compound of formula I for the manufacture of a medicament for the treatment of an inflammatory response due to a pathological condition or symptom in a mammal, such as a human, which is associated with inflammation.

The invention also includes the use of a combination of these compounds with type IV phosphodiesterase inhibitors to preferably cause synergistic decreases in the inflammatory response mediated by leukocytes.

The invention also provides a pharmaceutical composition comprising an effective amount of the compound of Formula (I), or a pharmaceutically acceptable salt thereof, in combination with a pharmaceutically acceptable diluent or carrier, and optionally, in combination with a Type IV phosphodiesterase (PDE) inhibitor. Preferably, the composition is presented as a unit dosage form.

Additionally, the invention provides a therapeutic method for preventing or treating a pathological condition or symptom in a mammal, such as a human, wherein the activity of A$_{2A}$ adenosine receptors is implicated and agonism of said receptors is desired, comprising administering to a mammal in need of such therapy, an effective amount of a compound of formula I, or a pharmaceutically acceptable salt thereof. It is believed that activation of A$_{2A}$ adenosine receptors inhibits inflammation by affecting neutrophils, mast cells, monocytes/macrophages, platelets T-cells and/or eosinophils. Inhibition of these inflammatory cells results in tissue protection following tissue insults.

In addition, the present invention provides a therapeutic method for treating biological diseases that includes the administration of an effective amount of a suitable antibiotic agent, antifungal agent or antiviral agent in conjunction with an A$_{2A}$ adenosine receptor agonist. If no anti-pathogenic agent is known the A$_{2A}$ agonist can be used alone to reduce inflammation, as may occur during infection with antibiotic resistant bacteria, or certain viruses such as those that cause SARS or Ebola. Optionally, the method includes administration of a type IV PDE inhibitor. The A$_{2A}$ adenosine receptor agonist can provide adjunctive therapy for treatment conditions such as, the inflammation, caused by sepsis, for example, human uremic syndrome when administered with antibiotics in the treatment of bio-terrorism weapons, such as anthrax, tularemia, *Escherichia coli*, plague and the like. The present invention also provides adjunctive therapy for treatment of lethal bacterial, fungal and viral infections such as anthrax, tularemia, *escherichia* and plague comprising administration of an antibacterial agent, an antifungal agent or an antiviral agent in conjunction with selective, A$_{2A}$ adenosine receptor agonists.

The present invention provides a therapeutic method for treating biological diseases that provoke inflammation either alone or in combination with a disease killing medicine. These include bacteria in combination with antibiotics, including but not limited to bacteria that cause anthrax, tularemia, plague, lyme disease and anthrax. Also included are viruses including but not limited to those that cause RSV, severe acute respiratory syndrome (SARS), influenza and Ebola with or without anti-viral therapy. Also included are yeast and fungal infections with or without anti-yeast or anti-fungal agents.

The antibacterial agent, antifungal agent or antiviral agent can be co-administered (e.g., simultaneously) with the A$_{2A}$ adenosine receptor agonist or they can be can be administered either simultaneously or as a mixture or they can be administered subsequently. The subsequent administration of the A$_{2A}$ adenosine receptor agonists can be prior to the agent, within minutes or up to about 48 hours after the administration of the agent. Preferably the administration of the A$_{2A}$ adenosine receptor agonists will be within about 24 hours and more preferably within about 12 hours.

The method of the invention will also be useful for treating patients with sepsis, severe sepsis, and potentially, the systemic inflammatory response syndrome, in addition to septic shock. The A$_{2A}$AR agonists exert multiple anti-inflammatory effects early in the inflammatory cascade, and thus a short course of an A$_{2A}$AR agonists could produce profound benefit in serious, life-threatening infectious and inflammatory disorders of humans, including inhalational anthrax, tularemia, *escherichia* and plague.

The anti-inflammatory effect of A$_{2A}$AR agonists has been documented in vivo, in experimental models of meningitis, peritonitis and arthritis. The potentially fatal syndrome of bacterial sepsis is an increasingly common problem in acute care units. Sepsis and septic shock, now the eleventh leading cause of death in the United States, are increasing in frequency. Current estimates indicate that about 900,000 new cases of sepsis (approximately 60% Gram negative) occur in the United States annually with an estimated crude mortality rate of 35%. Furthermore, the mortality rate, as assessed in recent clinical trials, is approximately 25%, while approximately 10% of patients die from their underlying disease. Shock develops in approximately 200,000 cases annually with an attributable mortality rate of 46% (92,000 deaths). Sepsis accounts for an estimated $ 5-10 billion annually in health care expenditures. It is now widely appreciated that among hospitalized patients in non-coronary intensive care units, sepsis is the most common cause of death. Sepsis syndrome is a public health problem of major importance. A$_{2A}$AR agonists are anticipated to have use as a new and unique adjunctive therapeutic approach to reduce morbidity and mortality. It is believed that this treatment will improve the outcome in systemic anthrax, tularemia, *escherichia* and plague.

The agonists of A$_{2A}$ adenosine receptors of the invention can inhibit neutrophil, macrophage and T cell activation and thereby reduce inflammation caused by bacterial and viral infections. The compounds, in conjunction with antibiotics or antiviral agents can prevent or reduce mortality caused by sepsis or hemolytic uremic syndrome or other inflammatory conditions. The effects of adenosine $A_{2A}$ agonists are enhanced by type IV phosphodiesterase inhibitors such as rolipram.

The invention also provides a pharmaceutical composition comprising an effective amount of the compound of formula (I), or a pharmaceutically acceptable salt thereof, in combination with a pharmaceutically acceptable diluent or carrier. Preferably, the composition is presented as a unit dosage form, and can be adapted for parenteral, e.g., intravenous infusion.

The invention also provides a compound of formula I for use in medical therapy (e.g., for use as an adjunct in the treatment of potentially lethal bacterial infections, such as, anthrax, tularemia, *Escherichia*, plague, or other bacterial or viral infections, and treatment of systemic intoxification caused by bacterial and/or viral infections, as well as the use of a compound of formula I for the manufacture of a medicament for reducing inflammation caused by the bacteria or virus or the treatment thereof in a mammal, such as a human. The compounds of the invention are also useful for treatment of treating systemic intoxification wherein the bacterial or viral agents cause inflammation either directly or as a result of treatment, e.g., with an antibiotic or antiviral agent.

Sepsis is a severe illness caused by overwhelming infection of the bloodstream by toxin-producing bacteria or viruses. The infection, which can manifest as inflammation, can be caused by the bacteria or virus pathogens directly or from the treatment thereof, i.e., the death of the pathogens due to treatment with antibacterial or antiviral agents. Sepsis can be also be viewed as the body's response to an infection. The infection can be caused by microorganisms or "germs" (usually bacteria) invade the body, can be limited to a particular body region (e.g., a tooth abscess) or can be widespread in the bloodstream (often referred to as "septicemia" or "blood poisoning")

The systemic intoxification or inflammatory shock is often referred to as Septic shock; Bacteremic shock; Endotoxic shock; Septicemic shock; or Warm shock.

Septic shock is a serious, abnormal condition that occurs when an overwhelming infection leads to low blood pressure and low blood flow. Vital organs, such as the brain, heart, kidneys, and liver may not function properly or may fail. Septic shock occurs most often in the very old and the very young. It also occurs in people with underlying illnesses. Any bacterial organism can cause septic shock. Fungi and viruses may also cause this condition. Toxins released by the bacteria, fungi or viruses may cause direct tissue damage, and may lead to low blood pressure and/or poor organ function. These toxins can also produce a vigorous inflammatory response from the body, which contributes to septic shock.

In another aspect, the present invention also provides a method to treat severe acute respiratory syndrome (SARS), comprising administering to a mammal in need of said therapy, an effective anti-inflammatory amount of an agonists of $A_{2A}$ adenosine receptor, optionally with a PDE-IV inhibitor, such as, rolipram.

The present invention provides compounds and methods of their use for detecting the presence of, and assessing the severity of, coronary artery stenoses in a mammal, such as a human or domestic animal. Preferably, the compounds of the invention are used as pharmacological stress-inducing agents or stressors that are useful in pharmacological stress imaging for the detection and assessment of coronary artery disease.

The specific compounds of the invention useful as stress-inducing agents are potent and selective at $A_{2A}$ adenosine receptors, but are also short-acting, so that they are rapidly cleared by the body following the imaging process.

Thus, the present invention provides a method for detecting the presence and severity of coronary artery stenoses in a mammal, such as a human subject, comprising (1) administering an amount of one or more compounds of the general formula (I) and (2) performing a technique on said mammal to detect and/or determine the severity of said coronary artery stenoses.

The invention provides a compound of formula (I) for use in medical diagnostic procedures, preferably for use in detecting the presence of, and assessing the severity of, coronary artery stenoses in a human subject. The present invention provides the use of a compound of formula (I) for the manufacture of a pharmacologic vasodilator agent which could be used with clinical perfusion imaging techniques for diagnosing and assessing the extent of coronary artery disease. Preferred perfusion imaging techniques are planar or single photon emission computed tomography (SPECT) gamma camera scintigraphy, positron emission tomography (PET), nuclear magnetic resonance (NMR) imaging, magnetic resonance imaging (MRI) imaging, perfusion contrast echocardiography, digital subtraction angiography (DSA) and ultrafast X-ray computed tomography (CINE CT).

The invention also provides a pharmaceutical composition comprising an effective amount of the compound of formula (I), or a pharmaceutically acceptable salt thereof, in combination with a pharmaceutically acceptable diluent or carrier. Preferably, the composition is presented as a unit dosage form, and can be adapted for parenteral, e.g., intravenous infusion.

DETAILED DESCRIPTION OF THE INVENTION

Figure 1:
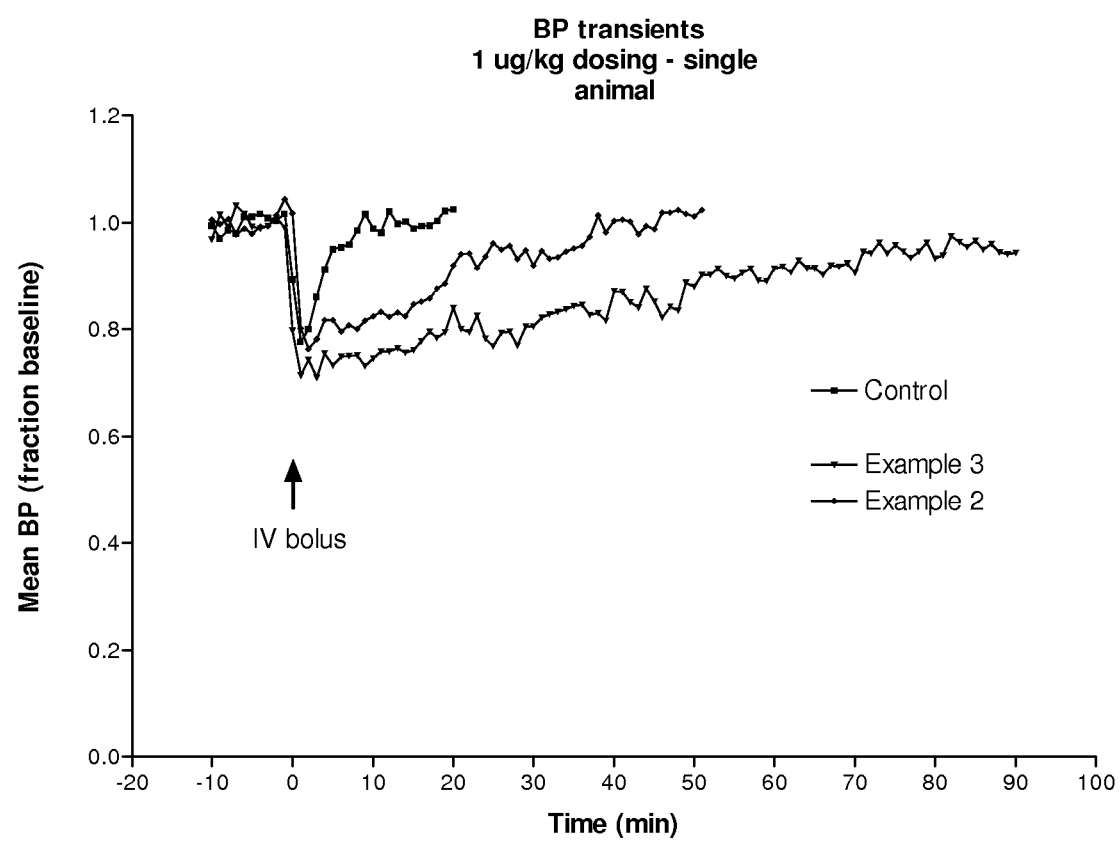
FIG. 1 is an illustration of the duration of action of $A_{2A}$ agonists by monitoring the reduction of blood pressure in rats after administration of compounds of the present invention compared with other $A_{2A}$ agonists.

The following definitions are used, unless otherwise described. Halo is fluoro, chloro, bromo, or iodo. Alkyl, alkoxy, aralkyl, alkylaryl, etc. denote both straight and branched alkyl groups; but reference to an individual radical such as "propyl" embraces only the straight chain radical, a branched chain isomer such as "isopropyl" being specifically referred to. Aryl includes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that the compounds of formula (I) have more than one chiral center and may be isolated in optically active and racemic forms. Preferably, the riboside moiety of formula (I) is derived from D-ribose. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, or enzymatic techniques, by synthesis from optically-active starting materials, by chiral synthesis, or by chromatographic separation using a chiral stationary phase) and how to determine adenosine agonist activity using the tests described herein, or using other similar tests which are well known in the art.

Among the inflammatory responses that can be treated (including treated prophylactically) with a compound of formula I, optionally with a Type IV PDE inhibitor, are inflammation due to:

(a) autoimmune stimulation (autoimmune diseases), such as lupus erythematosus, multiple sclerosis, infertility from endometriosis, type I diabetes mellitus including the destruction of pancreatic islets leading to diabetes and the inflammatory consequences of diabetes, including leg ulcers, Crohn's disease, ulcerative colitis, inflammatory bowel disease, osteoporosis and rheumatoid arthritis;

(b) allergic diseases such as asthma, hay fever, rhinitis, poison ivy, vernal conjunctivitis and other eosinophil-mediated conditions;

(c) skin diseases such as psoriasis, contact dermatitis, eczema, infectious skin ulcers, healing of open wounds, cellulitis;

(d) infectious diseases including sepsis, septic shock, encephalitis, infectious arthritis, endotoxic shock, gram negative shock, Jarisch-Herxheimer reaction, anthrax, plague, tularemia, ebola, shingles, toxic shock, cerebral malaria, bacterial meningitis, acute respiratory distress syndrome (ARDS), chronic obstructive pulmonary disease (COPD), lyme disease, HIV infection, (TNFα-enhanced HIV replication, TNFα inhibition of reverse transcriptase inhibitor activity);

(e) wasting diseases: cachexia secondary to cancer and HIV;

(f) organ, tissue or cell transplantation (e.g., bone marrow, cornea, kidney, lung, liver, heart, skin, pancreatic islets) including transplant rejection, and graft versus host disease;

(g) adverse effects from drug therapy, including adverse effects from amphotericin B treatment, adverse effects from immunosuppressive therapy, e.g., interleukin-2 treatment, adverse effects from OKT3 treatment, contrast dyes, antibiotics, adverse effects from GM-CSF treatment, adverse effects of cyclosporine treatment, and adverse effects of aminoglycoside treatment, stomatitis and mucositis due to immunosuppression;

(h) cardiovascular conditions including circulatory diseases induced or exasperated by an inflammatory response, such as ischemia, atherosclerosis, peripheral vascular disease, restenosis following angioplasty, inflammatory aortic aneurysm, vasculitis, stroke, spinal cord injury, congestive heart failure, hemorrhagic shock, ischemia/reperfusion injury, vasospasm following subarachnoid hemorrhage, vasospasm following cerebrovascular accident, pleuritis, pericarditis, and the cardiovascular complications of diabetes;

(i) dialysis, including pericarditis, due to peritoneal dialysis;

(j) gout; and (k) chemical or thermal trauma due to burns, acid, alkali and the like.

Of particular interest and efficacy is the use of the present compounds to limit inflammatory responses where the ischemia/reperfusion injury is caused by angioplasty or thrombolysis. Also of particular interest and efficacy is the use of the present compounds to limit inflammatory responses due to organ, tissue or cell transplantation, i.e., the transplantation of allogeneic or xenogeneic tissue into a mammalian recipient, autoimmune diseases and inflammatory conditions due to circulatory pathologies and the treatment thereof, including angioplasty, stent placement, shunt placement or grafting. Unexpectedly, it was found that administration of one or more compounds of formula (I) was effective after the onset of the inflammatory response, e.g., after the subject was afflicted with the pathology or trauma that initiates the inflammatory response.

Tissue or cells comprising ligand bound receptor sites can be used to measure the selectively of test compounds for specific receptor subtypes, the amount of bioactive compound in blood or other physiological fluids, or can be used as a tool to identify potential therapeutic agents for the treatment of diseases or conditions associated with receptor site activation, by contacting said agents with said ligand-receptor complexes, and measuring the extent of displacement of the ligand and/or binding of the agent, or the cellular response to said agent (e.g., cAMP accumulation).

Specific and preferred values listed below for radicals, substituents, and ranges, are for illustration only; they do not exclude other defined values or other values within defined ranges for the radicals and substituents.

Specifically, $(C_1-C_8)$alkyl can be methyl, ethyl, propyl, isopropyl, butyl, iso-butyl, sec-butyl, pentyl, 3-pentyl, hexyl, heptyl, octyl and the like. As used herein, the term "$(C_1-C_8)$alkoxy" can be methoxy, ethoxy, propoxy, isopropoxy, butoxy, iso-butoxy, sec-butoxy, pentoxy, 3-pentoxy, hexyloxy, 1-methylhexyloxy, heptyloxy and the like.

As used herein, the term "cycloalkyl" can be bicycloalkyl (norbornyl, 2.2.2-bicyclooctyl, etc.) and tricycloalkyl(adamantyl, etc.), optionally including 1-2 N, O or S. Cycloalkyl also encompasses (cycloalkyl)alkyl. Thus, $(C_3-C_6)$cycloalkyl can be cyclopropyl, cyclobutyl, cyclopentyl, cyclohexyl and the like. Specifically, $(C_6-C_{12})$bicycloalkyl includes norbornyl, 2.2.2-bicyclooctyl and the like.

As used herein, the term "$(C_1-C_8)$alkoxy" can be methoxy, ethoxy, propoxy, isopropoxy, butoxy, iso-butoxy, sec-butoxy, pentoxy, 3-pentoxy, hexyloxy; and the like.

As used herein, the term "$(C_2-C_6)$alkenyl" can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, and the like.

As used herein, the term "$(C_2-C_6)$alkynyl" can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and the like.

As used herein, the term "$(C_1-C_8)$alkanoyl" can be acetyl, propanoyl, butanoyl, and the like.

As used herein, the term "halo$(C_1-C_8)$alkyl" can be iodomethyl, bromomethyl, chloromethyl, fluoromethyl, trifluoromethyl, 2-chloroethyl, 2-fluoroethyl, 2,2,2-trifluoroethyl, pentafluoroethyl, and the like.

As used herein, the term "hydroxy$(C_1-C_6)$alkyl" can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, 6-hydroxyhexyl, and the like.

As used herein, the term "$(C_1-C_8)$alkylthio" can be methylthio, ethylthio, propylthio, isopropylthio, butylthio, isobutylthio, pentylthio, hexylthio, and the like.

As used herein, the term "aryl includes phenyl, indenyl, indanyl, naphthyl, and the like. In addition, aryl includes ortho-fused bicyclic carbocyclic radicals having about nine to ten ring atoms in which at least one ring is aromatic. The term "aryl" can include radicals of an ortho-fused bicyclic heterocycle of about eight to ten ring atoms derived therefrom, particularly a benz-derivative or one derived by fusing a propylene, trimethylene, or tetramethylene diradical thereto.

As used herein, the term "heteroaryl" can be a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, ($C_1$-$C_8$)alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

As used herein, the  symbol in the heterocyclic X ring denotes that the ring can have one or two double bonds and may be aromatic. Non-limiting examples of X rings include:

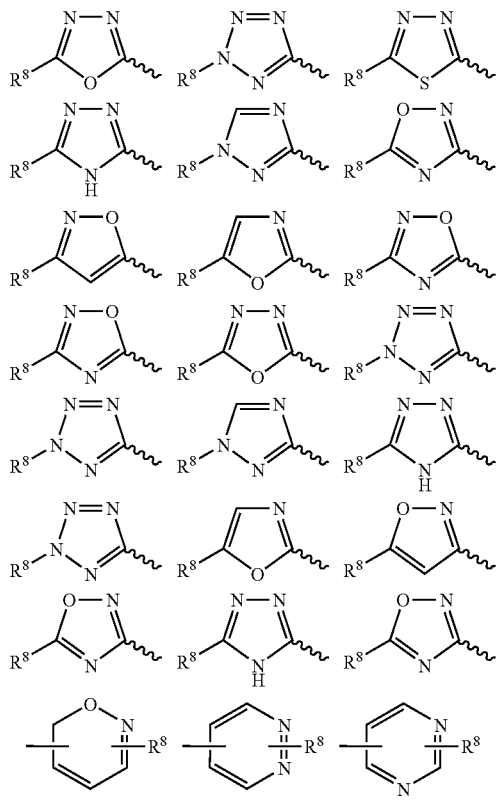

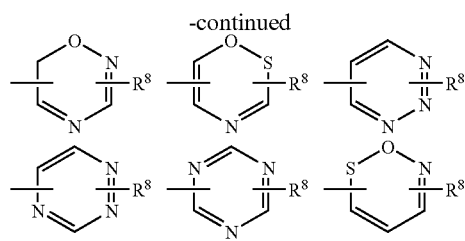

and the like.

The term "heterocycle" generally represents a non aromatic heterocyclic group, having from 3 to about 10 ring atoms, which can be saturated or partially unsaturated, containing at least one heteroatom (e.g., 1, 2, or 3) selected from the group consisting of oxygen, nitrogen, and sulfur. Specific, "heterocycle" groups include monocyclic, bicyclic, or tricyclic groups containing one or more heteroatoms selected from the group consisting of oxygen, nitrogen, and sulfur. A "heterocycle" group also can include one or more oxo groups (=O) attached to a ring atom. Non-limiting examples of heterocycle groups include 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuelidine, thiomorpholine, and the like.

The term "alkylene" refers to a divalent straight or branched hydrocarbon chain (e.g. ethylene —$CH_2$—$CH_2$—).

The term "aryl($C_1$-$C_8$)alkylene" for example includes benzyl, phenethyl, naphthylmethyl and the like.

The carbon atom content of various hydrocarbon-containing moieties is indicated by a prefix designating the minimum and maximum number of carbon atoms in the moiety, i.e., the prefix $C_i$-$C_j$ indicates a moiety of the integer "i" to the integer "j" carbon atoms, inclusive. Thus, for example, ($C_1$-$C_8$)alkyl refers to alkyl of one to eight carbon atoms, inclusive.

The compounds of the present invention are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours and "rt" for room temperature).

A specific value for $R^1$ is hydrogen, —OH, halo, —$CH_2OH$, —OMe, —OAc, —$NH_2$, —NHMe, —$NMe_2$ or —NHAc.

Another specific value for $R^1$ is hydrogen, —OH, —F, —OMe, —OAc, —$NH_2$, —NHMe, —$NMe_2$ or —NHAc.

Another specific value for $R^1$ is hydrogen, —OH, —F, —OMe, or —$NH_2$.

Another specific value for $R^1$ is hydrogen, —OH, —F, or —$NH_2$.

A more specific value for $R^1$ is hydrogen or —OH.

A specific value for $R^2$ is hydrogen, halo, or ($C_1$-$C_8$)alkyl, cyclopropyl, cyclohexyl or benzyl.

Another specific value for $R^2$ is hydrogen, —F, methyl, ethyl or propyl.

Another specific value for $R^2$ is hydrogen or methyl.

A more specific value for $R^2$ is hydrogen.

A specific value for $R^1$, $R^2$ and the carbon atom to which they are attached is carbonyl (C=O).

A specific value for $R^3$ is hydrogen, OH, OMe, OAc, $NH_2$, NHMe, $NMe_2$ or NHAc.

Another specific value for $R^3$ is hydrogen, OH, OMe, or $NH_2$.

Another specific value for $R^3$ is hydrogen, OH, or $NH_2$.

A more specific value for $R^3$ is hydrogen or OH.

A specific value for the ring comprising $R^4$, $R^5$ and the atom to which they are connected is cyclopentane, cyclohexane, piperidine, dihydro-pyridine, tetrahydro-pyridine, pyridine, piperazine, decaline, tetrahydro-pyrazine, dihydro-pyrazine, pyrazine, dihydro-pyrimidine, tetrahydro-pyrimidine, hexahydro-pyrimidine, pyrazine, imidazole, dihydro-imidazole, imidazolidine, pyrazole, dihydro-pyrazole, and pyrazolidine.

A more specific value for the ring comprising $R^4$ and $R^5$ and the atom to which they are connected is, cyclohexane, piperidine or piperazine.

A specific value for $R^6$ is $(C_1-C_8)$alkyl, substituted $(C_1-C_8)$ alkyl, halo, —$OR^a$, —$CO_2R^a$, —$OCO_2R^a$, —$C(=O)R^a$, —$OC(=O)R^a$, —$NR^aR^b$, —$C(=O)NR^aR^b$, —$OC(=O)NR^aR^b$, or aryl.

Another specific value for $R^6$ is $(C_1-C_4)$alkyl, chloro, fluoro, phenyl, —$OR^a$, —$CH_2OR^a$, —$CO_2R^a$, —$CH_2CO_2R^a$, —$OCO_2R^a$, —$CH_2OCO_2R^a$, —$C(=O)R^a$, —$CH_2C(=O)R^a$, —$OC(=O)R^a$, —$CH_2C(=O)R^a$, —$NR^aR^b$, —$CH_2NR^aR^b$, —$C(=O)NR^aR^b$, $CH_2C(=O)NR^aR^b$, —$OC(=O)NR^aR^b$, or —$CH_2C(=O)NR^aR^b$.

Another specific value for $R^6$ is OH, OMe, methyl, ethyl, propyl, isopropyl, n-butyl, sec-butyl, isobutyl, tert-butyl, —$CH_2OH$, phenyl, —OAc, —$CH_2OAc$, —$CO_2H$, —$CO_2Me$, —$CO_2Et$, —$CO_2$—Pr, —$CO_2i$-Bu, —$CO_2t$-Bu, —$OCO_2Me$, $OCO_2Et$, —$C(=O)CH_3$, —$CONH_2$, —CONHMe, —$CONMe_2$, —CONMeEt, —$NH_2$, —NHMe, —$NMe_2$, —NHEt, —$N(Et)_2$, or —$CH_2N(CH_3)_2$.

Another specific value for $R^6$ is OH, OMe, methyl, ethyl, propyl, isopropyl, n-butyl, sec-butyl, isobutyl, tert-butyl, —$CH_2OH$, phenyl, —OAc, —$CH_2OAc$, —$CO_2Me$, —$CO_2Et$, —$CO_2$—Pr, —$CO_2i$-Bu, —$CO_2t$-Bu, —$OCO_2Me$, —$OCO_2Et$, —$CONMe_2$, —CONMeEt.

A specific number of $R^6$ groups substituted on the Z ring is an integer from 1 to about 4.

A specific value for $R^a$ is hydrogen, methyl, ethyl, propyl, isopropyl, n-butyl, sec-butyl, isobutyl, tert-butyl, phenyl or benzyl.

A specific value for $R^b$ is hydrogen, methyl, ethyl, propyl, isopropyl, n-butyl, sec-butyl, isobutyl, tert-butyl, phenyl or benzyl.

Another specific value for $R^a$ is hydrogen, methyl, ethyl, propyl, isopropyl, n-butyl, sec-butyl, isobutyl, or tert-butyl and $R^b$ is hydrogen, or methyl.

Another specific value for $R^a$ and $R^b$ together with the nitrogen to which they are attached, form a pyrrolidino, piperidino, morpholino, or thiomorpholino ring.

Another specific value for $R^a$ and $R^b$ together with the nitrogen to which they are attached, form a pyrrolidino, piperidino, or morpholino, ring.

A specific value for $R^7$ is hydrogen, $(C_1-C_4)$alkyl, aryl, aryl$(C_1-C_8)$alkylene, diaryl$(C_1-C_8)$alkylene, heteroaryl$(C_1-C_8)$alkylene, or diheteroaryl$(C_1-C_8)$alkylene.

Another specific value for $R^7$ is hydrogen, methyl, ethyl, 3-pentyl, phenylCH$_2$CH$_2$—, (phenyl)$_2$CHCH$_2$—, pyridylCH$_2$—, benzyl, or

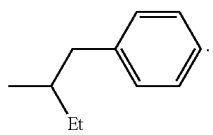

Another specific value for $R^7$ is hydrogen, 3-pentyl, pyridylmethyl, or benzyl.

A specific value for —$N(R^7)_2$ is amino, methylamino, dimethylamino, ethylamino, diethylamino, pentylamino, diphenylethylamino, benzylamino, or

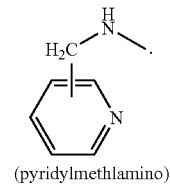

(pyridylmethlamino)

A specific pyridylmethylamino Group is

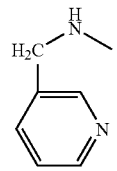

A more specific value for $R^7$ is H.

Another specific value for $N(R^7)_2$ is amino($NH_2$), 3-pentylamino, diphenylethylamino, pyridylmethylamino, benzylamino, or a group having the formula:

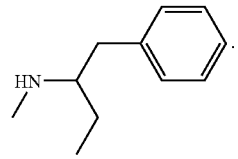

Another specific value for —$N(R^7)_2$ is amino, diphenylethylamino, pentylamino or benzylamino.

A more specific value for $N(R^7)_2$ is amino.

A specific value for X is —$CH_2OR^e$, —$CO_2R^e$, —$CH_2OC(O)R^e$, —$C(O)NR^eR^f$, or —$CH_2N(R^e)(R^f)$.

Another specific value for X is —$CH_2OR^e$ or —$C(O)NR^eR^f$.

Another specific value for X is

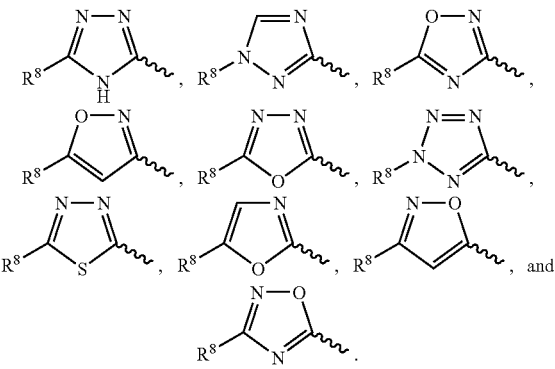

Another specific value for X is

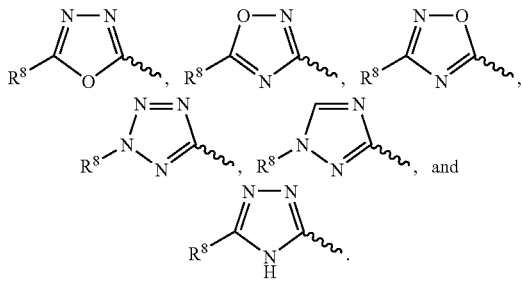

Another specific value for X is

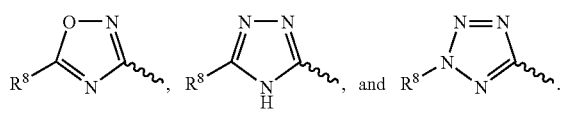

A specific value for $R^8$ is methyl, ethyl, isopropyl, isopropenyl, —CH=CH$_2$, CH$_2$OH, propyl, —CH$_2$—CH=CH$_2$, —CH=CH—CH$_3$, cyclopropyl, cyclopropenyl, cyclopropylmethyl, cyclopropenylmethyl, cyclobutyl, cyclobutenyl, —(CH$_2$)Y(CH$_2$)$_n$H, —(CH$_2$)$_n$COOCH$_3$, —(CH$_2$)$_n$CO(CH$_2$)$_n$H, where Y is O, S, N(CH$_2$)$_n$.

Another specific value for $R^8$ is (C$_1$-C$_3$)alkyl, CH$_2$OH, cyclopropyl, cyclobutyl, cyclopropylmethyl, —(CH$_2$)$_2$CO$_2$CH$_3$, —(CH$_2$)$_{2\text{-}30}$H, —(CH$_2$)$_2$halogen.

A more specific value for $R^8$ is methyl, ethyl, propyl, 2-propenyl, cyclopropyl, cyclobutyl, cyclopropylmethyl, —(CH$_2$)$_2$CO$_2$CH$_3$, —(CH$_2$)$_{2\text{-}3}$OH A more specific value for $R^8$ is methyl, ethyl, cyclopropyl.

A specific value for $R^e$ is cyclopropyl, or cyclobutyl.
A specific value for $R^e$ is cyclopropyl.
A specific value for $R^e$ is cyclobutyl.
A specific value for $R^f$ is hydrogen, or (C$_1$-C$_8$)alkyl.
Another specific value for $R^f$ is hydrogen, methyl, ethyl, or propyl.
Another specific value for $R^f$ is hydrogen, or methyl.
Another specific value for $R^f$ is hydrogen.
A specific value for i is 1.
Another specific value for i is 2.
A specific value for j is 1.
Another specific value for j is 2.
A specific value for m is 0, 1, or 2.
A more specific value for m is 0, or 1.
Specific examples of rings comprising $R^4$, $R^5$ and the atom to which they are connected include:

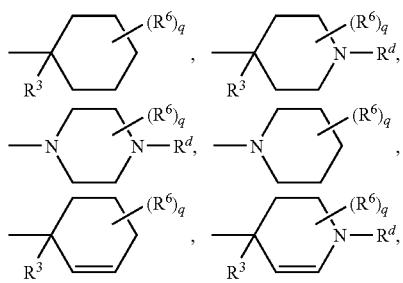

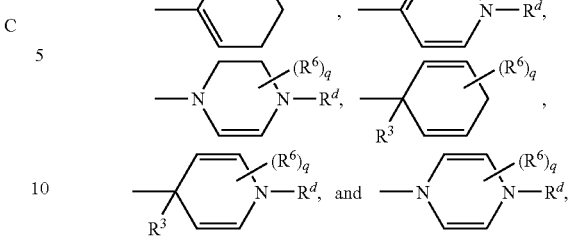

where q is from 1 to 14 and $R^d$ is hydrogen, provided that when q is zero then $R^d$ is not hydrogen.

More specific examples of rings comprising $R^4$, $R^5$ and the atom to which they are connected include:

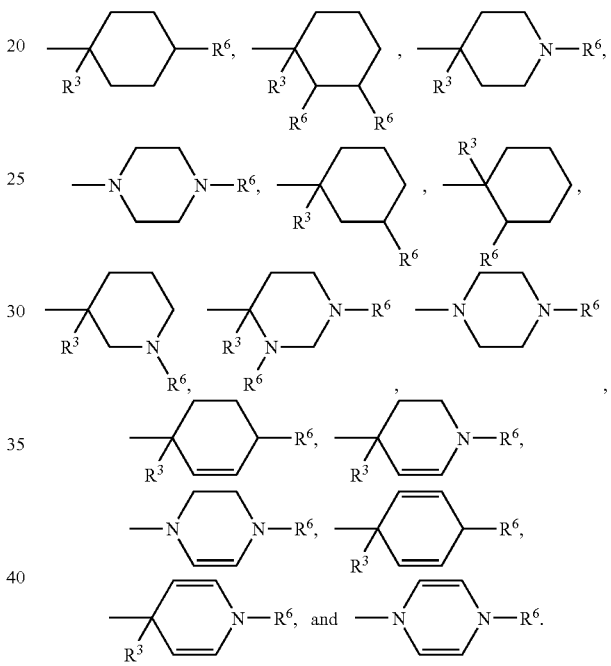

A specific value for the ring comprising —C(R$^3$)R$^4$R$^5$ is 2-methyl cyclohexane, 2,2-dimethylcyclohexane, 2-phenyl-cyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane. 4-cyclohexanecarboxylc acid, 4-cyclohexanecarboxylc acid esters, or 4-methyloxyalkanoyl-cyclohexane.

A specific value for the ring comprising —C(R$^3$)R$^4$R$^5$ is 4-piperidine, 4-piperidine-1-carboxylic acid, 4-piperidine-1-carboxylic acid methyl ester, 4-piperidine-1-carboxylic acid ethyl ester, 4-piperidine-1-carboxylic acid propyl ester, 4-piperidine-1-carboxylic acid tert-butyl ester, 1-piperidine, 1-piperidine-4-carboxylic acid methyl ester, 1-piperidine-4-carboxylic acid ethyl ester, 1-piperidine-4-carboxylic acid propyl ester, 1-piperidine-4-carboxylic acid tert-butyl ester, 1-piperidine-4-carboxylic acid methyl ester, 3-piperidine, 3-piperidene-1-carboxylic acid, 3-piperidine-1-carboxylic acid methyl ester, 3-piperidine-1-carboxylic acid tert-butyl ester, 1,4-piperazine, 4-piperazine-1-carboxylic acid, 4-piperazine-1-carboxylic acid methyl ester, 4-piperazine-1-carboxylic acid ethyl ester, 4-piperazine-1-carboxylic acid propyl ester, 4-piperazine-1-carboxylic acid tert-butylester, 1,3-piperazine, 3-piperazine-1-carboxylic acid, 3-piperazine-1-carboxylic acid methyl ester, 3-piperazine-1-carboxylic acid ethyl ester, 3-piperazine-1-carboxylic acid propyl ester, 3-piperidine-1-carboxylic acid tert-butylester, 1-piperidine-3-carboxylic acid methyl ester, 1-piperidine-3-carboxylic acid ethyl ester, 1-piperidine-3-carboxylic acid propyl ester or 1-piperidine-3-carboxylic acid tert-butyl ester.

A specific value for the ring comprising $R^4$ and $R^5$ is 2-methyl cyclohexane, 2,2-dimethylcyclohexane, 2-phenyl cyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane, 4-piperidine-1-carboxylic acid methyl ester, 4-piperidine-1-carboxylic acid tert-butyl ester 4-piperidine, 4-piperazine-1-carboxylic acid methyl ester, 4-piperidine-1-carboxylic acid tert-butylester, 1-piperidine-4-carboxylic acid methyl ester, 1-piperidine-4-carboxylic acid tert-butyl ester, tert-butylester, 1-piperidine-4-carboxylic acid methyl ester, or 1-piperidine-4-carboxylic acid tert-butyl ester, 3-piperidine-1-carboxylic acid methyl ester, 3-piperidine-1-carboxylic acid tert-butyl ester, 3-piperidine, 3-piperazine-1-carboxylic acid methyl ester, 3-piperidine-1-carboxylic acid tert-butylester, 1-piperidine-3-carboxylic acid methyl ester, 1-piperidine-3-carboxylic acid tert-butyl ester.

Specific compounds of the invention include formula (IA)

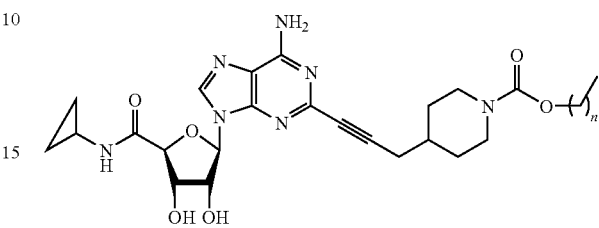

(IA)

In formula (IA) n is 0, 1, 2, 3, 4, 5, 6, 7, 8, 9, 10, 11, 12, 13, 14, 15, 16, 17, or 18. In another group of specific compounds n is, 5, 6, 7, 8, 9, 10, 11, 12, 13, 14, 15, 16, 17, or 18.

Specific compounds of the invention include formula (IB)

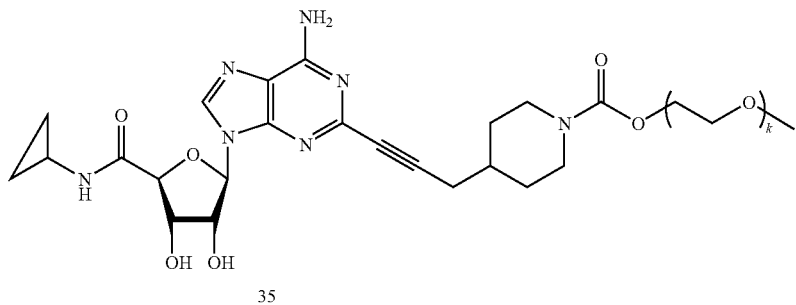

(IB)

In formula (IB) k is 1, 2, 3, 4, 5, 6, 7, 8, 9, 10, 11, 12, 13, 14, 15, 16, 17, or 18.

Specific compounds of the invention include formula (IC)

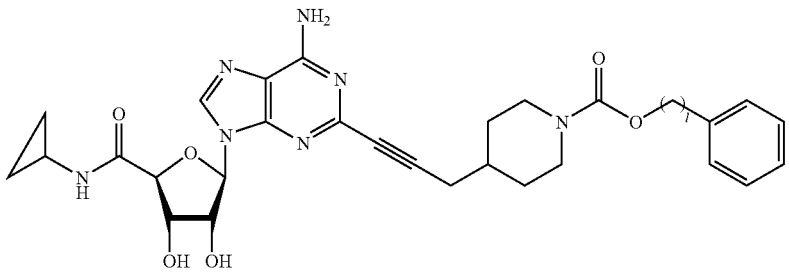

(IC)

In formula (IC) l is 0, 1, 2, 3, or 4.

Other specific compounds of the invention include

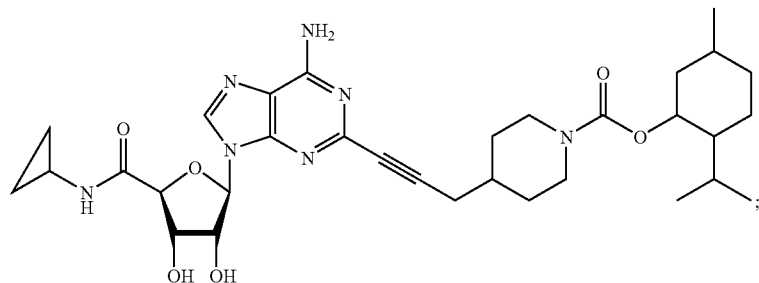

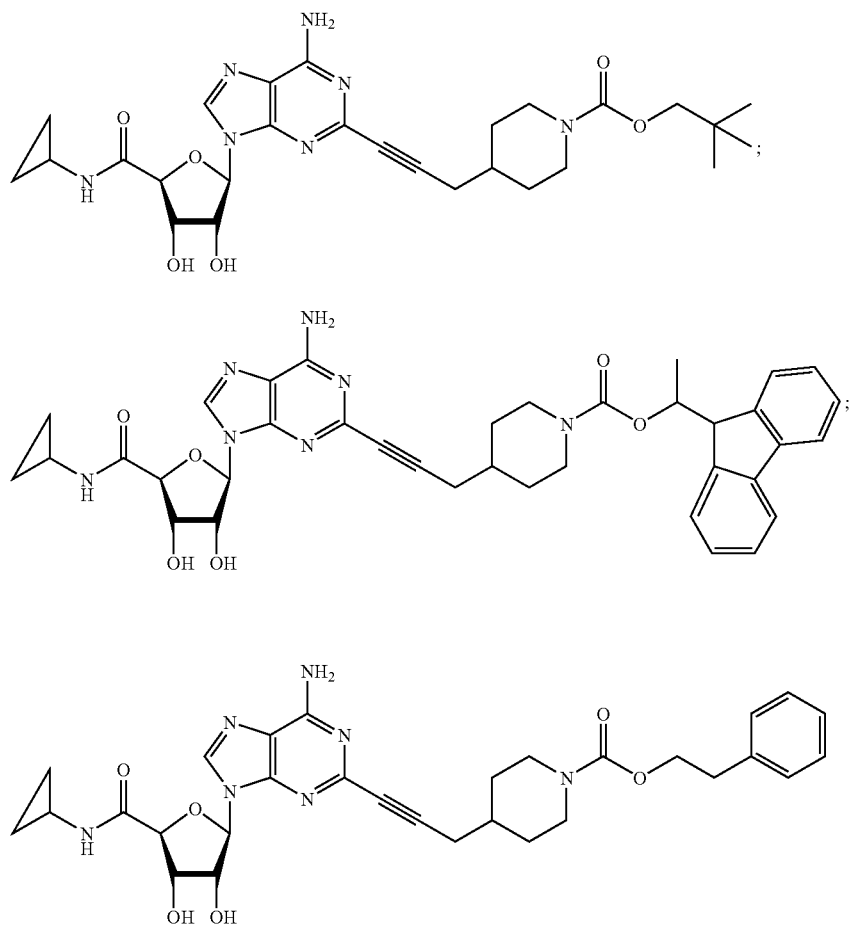
Additional compounds of the invention are depicted in Table 1, below:
TABLE 1
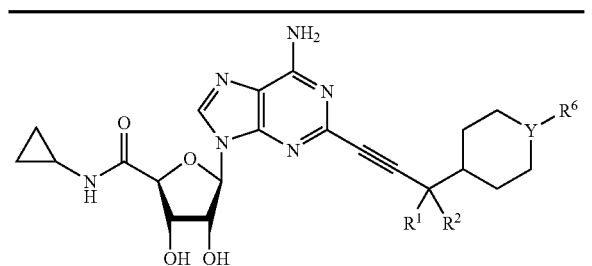
| Compound | R¹ | R² | Y | R⁶ |
|---|---|---|---|---|
| 101 | H | H | CH | CO₂Me |
| 102 | H | H | CH | CO₂Et |
| 103 | H | H | CH | CO₂iPr |
| 104 | H | H | CH | CO₂tBu |
| 105 | H | H | CH | CO₂iBu |
| 106 | H | H | CH | CH₂OH |
| 107 | H | H | CH | CH₂OAc |
| 108 | H | H | N | CO₂Me |
| 109 | H | H | N | CO₂Et |
| 110 | H | H | N | CO₂iPr |
| 111 | H | H | N | CO₂tBu |
| 112 | H | H | N | CO₂iBu |
TABLE 2
| Compound # | R⁶ |
|---|---|
| 201 | 2-CH₃ |
| 202 | 3-CH₃ (R) |
| 203 | 3-CH₃ (S) |
| 204 | 3-Et (R) |
| 205 | 3-Et (S) |
| 206 | 4-Me |
| 207 | 4-Et |
| 208 | 4-Pr |
| 209 | 4-tBu |
| 210 | 4-Phenyl |

TABLE 3

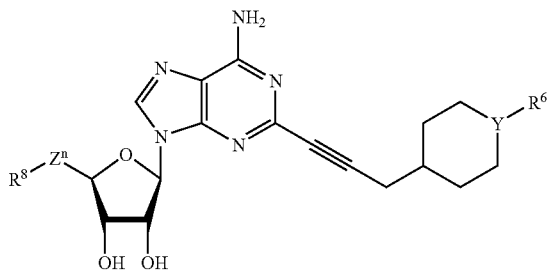

$R^1 = R^2 = H, R^7 = NH_2$

TABLE 3-continued

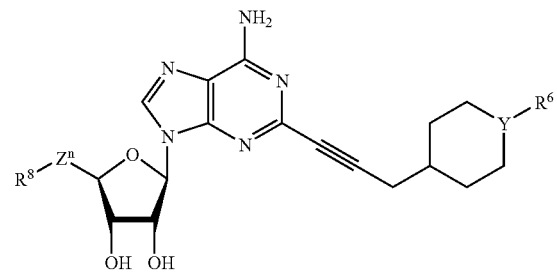

$R^1 = R^2 = H, R^7 = NH_2$

| Compound | $R^8$ | Z | Y | $R^6$ |
|---|---|---|---|---|
| 301 | Methyl | Z1 | CH | $CO_2Me$ |
| 302 | Methyl | Z1 | CH | $CO_2Et$ |
| 303 | Methyl | Z1 | CH | $CO_2iPr$ |
| 304 | Methyl | Z1 | CH | $CO_2tBu$ |
| 305 | Methyl | Z1 | CH | $CO_2iBu$ |
| 306 | Methyl | Z1 | CH | $CH_2OH$ |
| 307 | Methyl | Z1 | CH | $CH_2OAc$ |
| 308 | Methyl | Z1 | N | $CO_2Me$ |
| 309 | Methyl | Z1 | N | $CO_2Et$ |
| 310 | Methyl | Z1 | N | $CO_2iPr$ |
| 311 | Methyl | Z1 | N | $CO_2tBu$ |
| 312 | Methyl | Z1 | N | $CO_2iBu$ |
| 313 | Ethyl | Z1 | CH | $CO_2Me$ |
| 314 | Ethyl | Z1 | CH | $CO_2Et$ |
| 315 | Ethyl | Z1 | CH | $CO_2iPr$ |
| 316 | Ethyl | Z1 | CH | $CO_2tBu$ |
| 317 | Ethyl | Z1 | CH | $CO_2iBu$ |
| 318 | Ethyl | Z1 | CH | $CH_2OH$ |
| 319 | Ethyl | Z1 | CH | $CH_2OAc$ |
| 320 | Ethyl | Z1 | N | $CO_2Me$ |
| 321 | Ethyl | Z1 | N | $CO_2Et$ |
| 322 | Ethyl | Z1 | N | $CO_2iPr$ |
| 323 | Ethyl | Z1 | N | $CO_2tBu$ |
| 324 | Ethyl | Z1 | N | $CO_2iBu$ |
| 325 | Cyclopropyl | Z1 | CH | $CO_2Me$ |
| 326 | Cyclopropyl | Z1 | CH | $CO_2Et$ |
| 327 | Cyclopropyl | Z1 | CH | $CO_2iPr$ |
| 328 | Cyclopropyl | Z1 | CH | $CO_2tBu$ |
| 329 | Cyclopropyl | Z1 | CH | $CO_2iBu$ |
| 330 | Cyclopropyl | Z1 | CH | $CH_2OH$ |
| 331 | Cyclopropyl | Z1 | CH | $CH_2OAc$ |
| 332 | Cyclopropyl | Z1 | N | $CO_2Me$ |
| 333 | Cyclopropyl | Z1 | N | $CO_2Et$ |
| 334 | Cyclopropyl | Z1 | N | $CO_2iPr$ |
| 335 | Cyclopropyl | Z1 | N | $CO_2tBu$ |
| 336 | Cyclopropyl | Z1 | N | $CO_2iBu$ |
| 337 | Methyl | Z2 | CH | $CO_2Me$ |
| 338 | Methyl | Z2 | CH | $CO_2Et$ |
| 339 | Methyl | Z2 | CH | $CO_2iPr$ |
| 340 | Methyl | Z2 | CH | $CO_2tBu$ |
| 341 | Methyl | Z2 | CH | $CO_2iBu$ |
| 342 | Methyl | Z2 | CH | $CH_2OH$ |
| 343 | Methyl | Z2 | CH | $CH_2OAc$ |
| 344 | Methyl | Z2 | N | $CO_2Me$ |
| 345 | Methyl | Z2 | N | $CO_2Et$ |
| 346 | Methyl | Z2 | N | $CO_2iPr$ |
| 347 | Methyl | Z2 | N | $CO_2tBu$ |
| 348 | Methyl | Z2 | N | $CO_2iBu$ |
| 349 | Ethyl | Z2 | CH | $CO_2Me$ |
| 350 | Ethyl | Z2 | CH | $CO_2Et$ |
| 351 | Ethyl | Z2 | CH | $CO_2iPr$ |
| 352 | Ethyl | Z2 | CH | $CO_2tBu$ |
| 353 | Ethyl | Z2 | CH | $CO_2iBu$ |
| 354 | Ethyl | Z2 | CH | $CH_2OH$ |
| 355 | Ethyl | Z2 | CH | $CH_2OAc$ |
| 356 | Ethyl | Z2 | N | $CO_2Me$ |
| 357 | Ethyl | Z2 | N | $CO_2Et$ |
| 358 | Ethyl | Z2 | N | $CO_2iPr$ |
| 359 | Ethyl | Z2 | N | $CO_2tBu$ |
| 360 | Ethyl | Z2 | N | $CO_2iBu$ |
| 361 | Cyclopropyl | Z2 | CH | $CO_2Me$ |
| 362 | Cyclopropyl | Z2 | CH | $CO_2Et$ |
| 363 | Cyclopropyl | Z2 | CH | $CO_2iPr$ |
| 364 | Cyclopropyl | Z2 | CH | $CO_2tBu$ |
| 365 | Cyclopropyl | Z2 | CH | $CO_2iBu$ |
| 366 | Cyclopropyl | Z2 | CH | $CH_2OH$ |
| 367 | Cyclopropyl | Z2 | CH | $CH_2OAc$ |
| 368 | Cyclopropyl | Z2 | N | $CO_2Me$ |
| 369 | Cyclopropyl | Z2 | N | $CO_2Et$ |
| 370 | Cyclopropyl | Z2 | N | $CO_2iPr$ |
| 371 | Cyclopropyl | Z2 | N | $CO_2tBu$ |
| 372 | Methyl | Z3 | CH | $CO_2Me$ |
| 373 | Methyl | Z3 | CH | $CO_2Et$ |
| 374 | Methyl | Z3 | CH | $CO_2iPr$ |
| 375 | Methyl | Z3 | CH | $CO_2tBu$ |
| 376 | Methyl | Z3 | CH | $CO_2iBu$ |
| 377 | Methyl | Z3 | CH | $CH_2OH$ |
| 378 | Methyl | Z3 | CH | $CH_2OAc$ |
| 379 | Methyl | Z3 | N | $CO_2Me$ |
| 380 | Methyl | Z3 | N | $CO_2Et$ |
| 381 | Methyl | Z3 | N | $CO_2iPr$ |
| 382 | Methyl | Z3 | N | $CO_2tBu$ |
| 383 | Methyl | Z3 | N | $CO_2iBu$ |
| 384 | Ethyl | Z3 | CH | $CO_2Me$ |
| 385 | Ethyl | Z3 | CH | $CO_2Et$ |
| 386 | Ethyl | Z3 | CH | $CO_2iPr$ |
| 387 | Ethyl | Z3 | CH | $CO_2tBu$ |
| 388 | Ethyl | Z3 | CH | $CO_2iBu$ |
| 389 | Ethyl | Z3 | CH | $CH_2OH$ |
| 390 | Ethyl | Z3 | CH | $CH_2OAc$ |
| 391 | Ethyl | Z3 | N | $CO_2Me$ |
| 392 | Ethyl | Z3 | N | $CO_2Et$ |
| 393 | Ethyl | Z3 | N | $CO_2iPr$ |
| 394 | Ethyl | Z3 | N | $CO_2tBu$ |
| 395 | Ethyl | Z3 | N | $CO_2iBu$ |
| 396 | Cyclopropyl | Z3 | CH | $CO_2Me$ |
| 397 | Cyclopropyl | Z3 | CH | $CO_2Et$ |
| 398 | Cyclopropyl | Z3 | CH | $CO_2iPr$ |
| 399 | Cyclopropyl | Z3 | CH | $CO_2tBu$ |
| 400 | Cyclopropyl | Z3 | CH | $CO_2iBu$ |
| 401 | Cyclopropyl | Z3 | CH | $CH_2OH$ |
| 402 | Cyclopropyl | Z3 | CH | $CH_2OAc$ |
| 403 | Cyclopropyl | Z3 | N | $CO_2Me$ |
| 404 | Cyclopropyl | Z3 | N | $CO_2Et$ |
| 405 | Cyclopropyl | Z3 | N | $CO_2iPr$ |
| 406 | Cyclopropyl | Z3 | N | $CO_2tBu$ |
| 407 | Cyclopropyl | Z3 | N | $CO_2iBu$ |
| 408 | Methyl | Z4 | CH | $CO_2Me$ |
| 409 | Methyl | Z4 | CH | $CO_2Et$ |
| 410 | Methyl | Z4 | CH | $CO_2iPr$ |
| 411 | Methyl | Z4 | CH | $CO_2tBu$ |
| 412 | Methyl | Z4 | CH | $CO_2iBu$ |
| 413 | Methyl | Z4 | CH | $CH_2OH$ |
| 414 | Methyl | Z4 | CH | $CH_2OAc$ |
| 415 | Methyl | Z4 | N | $CO_2Me$ |
| 416 | Methyl | Z4 | N | $CO_2Et$ |
| 417 | Methyl | Z4 | N | $CO_2iPr$ |
| 418 | Methyl | Z4 | N | $CO_2tBu$ |
| 419 | Methyl | Z4 | N | $CO_2iBu$ |
| 420 | Ethyl | Z4 | CH | $CO_2Me$ |
| 421 | Ethyl | Z4 | CH | $CO_2Et$ |
| 422 | Ethyl | Z4 | CH | $CO_2iPr$ |
| 423 | Ethyl | Z4 | CH | $CO_2tBu$ |
| 424 | Ethyl | Z4 | CH | $CO_2iBu$ |

TABLE 3-continued

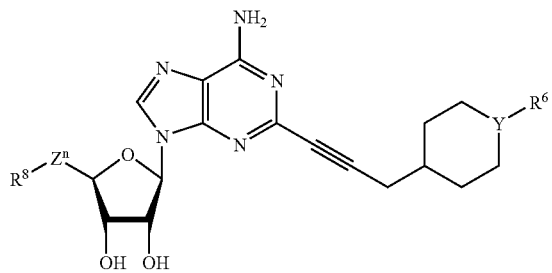

$R^1 = R^2 = H, R^7 = NH_2$

| Compound | $R^8$ | Z | Y | $R^6$ |
|---|---|---|---|---|
| 425 | Ethyl | Z4 | CH | $CH_2OH$ |
| 426 | Ethyl | Z4 | CH | $CH_2OAc$ |
| 427 | Ethyl | Z4 | N | $CO_2Me$ |
| 428 | Ethyl | Z4 | N | $CO_2Et$ |
| 429 | Ethyl | Z4 | N | $CO_2iPr$ |
| 430 | Ethyl | Z4 | N | $CO_2tBu$ |
| 431 | Ethyl | Z4 | N | $CO_2iBu$ |
| 432 | Cyclopropyl | Z4 | CH | $CO_2Me$ |
| 433 | Cyclopropyl | Z4 | CH | $CO_2Et$ |
| 434 | Cyclopropyl | Z4 | CH | $CO_2iPr$ |
| 435 | Cyclopropyl | Z4 | CH | $CO_2tBu$ |
| 436 | Cyclopropyl | Z4 | CH | $CO_2iBu$ |
| 437 | Cyclopropyl | Z4 | CH | $CH_2OH$ |
| 438 | Cyclopropyl | Z4 | CH | $CH_2OAc$ |
| 439 | Cyclopropyl | Z4 | N | $CO_2Me$ |
| 440 | Cyclopropyl | Z4 | N | $CO_2Et$ |
| 441 | Cyclopropyl | Z4 | N | $CO_2iPr$ |
| 442 | Cyclopropyl | Z4 | N | $CO_2tBu$ |
| 443 | Methyl | Z5 | CH | $CO_2Me$ |
| 444 | Methyl | Z5 | CH | $CO_2Et$ |
| 445 | Methyl | Z5 | CH | $CO_2iPr$ |
| 446 | Methyl | Z5 | CH | $CO_2tBu$ |
| 447 | Methyl | Z5 | CH | $CO_2iBu$ |
| 448 | Methyl | Z5 | CH | $CH_2OH$ |
| 449 | Methyl | Z5 | CH | $CH_2OAc$ |
| 450 | Methyl | Z5 | N | $CO_2Me$ |
| 451 | Methyl | Z5 | N | $CO_2Et$ |
| 452 | Methyl | Z5 | N | $CO_2iPr$ |
| 453 | Methyl | Z5 | N | $CO_2tBu$ |
| 454 | Methyl | Z5 | N | $CO_2iBu$ |
| 455 | Ethyl | Z5 | CH | $CO_2Me$ |
| 456 | Ethyl | Z5 | CH | $CO_2Et$ |
| 457 | Ethyl | Z5 | CH | $CO_2iPr$ |
| 458 | Ethyl | Z5 | CH | $CO_2tBu$ |
| 459 | Ethyl | Z5 | CH | $CO_2iBu$ |
| 460 | Ethyl | Z5 | CH | $CH_2OH$ |
| 461 | Ethyl | Z5 | CH | $CH_2OAc$ |
| 462 | Ethyl | Z5 | N | $CO_2Me$ |
| 463 | Ethyl | Z5 | N | $CO_2Et$ |
| 464 | Ethyl | Z5 | N | $CO_2iPr$ |
| 465 | Ethyl | Z5 | N | $CO_2tBu$ |
| 466 | Ethyl | Z5 | N | $CO_2iBu$ |
| 467 | Cyclopropyl | Z5 | CH | $CO_2Me$ |
| 468 | Cyclopropyl | Z5 | CH | $CO_2Et$ |
| 469 | Cyclopropyl | Z5 | CH | $CO_2iPr$ |
| 470 | Cyclopropyl | Z5 | CH | $CO_2tBu$ |
| 471 | Cyclopropyl | Z5 | CH | $CO_2iBu$ |
| 472 | Cyclopropyl | Z5 | CH | $CH_2OH$ |
| 473 | Cyclopropyl | Z5 | CH | $CH_2OAc$ |
| 474 | Cyclopropyl | Z5 | N | $CO_2Me$ |
| 475 | Cyclopropyl | Z5 | N | $CO_2Et$ |
| 476 | Cyclopropyl | Z5 | N | $CO_2iPr$ |
| 477 | Cyclopropyl | Z5 | N | $CO_2tBu$ |
| 478 | Cyclopropyl | Z5 | N | $CO_2iBu$ |

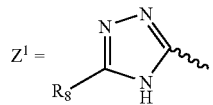

TABLE 3-continued

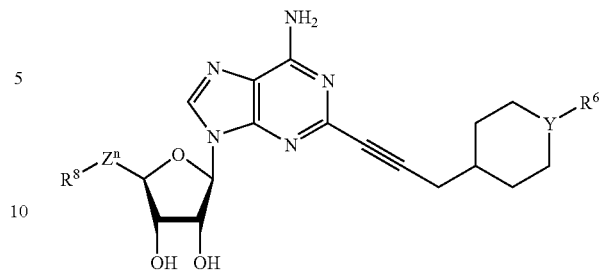

$R^1 = R^2 = H, R^7 = NH_2$

| Compound | $R^8$ | Z | Y | $R^6$ |
|---|---|---|---|---|

$Z^2$ =

$Z^3$ =

$Z^4$ =

$Z^5$ =

TABLE 4

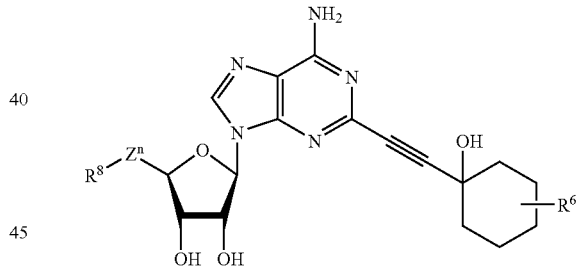

| Compound | $R^8$ | Z | $R^6$ |
|---|---|---|---|
| 501 | Methyl | Z1 | 2-$CH_3$ |
| 502 | Methyl | Z1 | 3-$CH_3$ (R) |
| 503 | Methyl | Z1 | 3-$CH_3$ (S) |
| 504 | Methyl | Z1 | 3-Et (R) |
| 505 | Methyl | Z1 | 3-Et (S) |
| 506 | Methyl | Z1 | 4-Me |
| 507 | Methyl | Z1 | 4-Et |
| 508 | Methyl | Z1 | 4-Pr |
| 509 | Methyl | Z1 | 4-tBu |
| 510 | Methyl | Z1 | 4-Phenyl |
| 511 | Ethyl | Z1 | 2-$CH_3$ |
| 512 | Ethyl | Z1 | 3-$CH_3$ (R) |
| 513 | Ethyl | Z1 | 3-$CH_3$ (S) |
| 514 | Ethyl | Z1 | 3-Et (R) |
| 515 | Ethyl | Z1 | 3-Et (S) |
| 516 | Ethyl | Z1 | 4-Me |
| 517 | Ethyl | Z1 | 4-Et |
| 518 | Ethyl | Z1 | 4-Pr |
| 519 | Ethyl | Z1 | 4-tBu |
| 520 | Ethyl | Z1 | 4-Phenyl |
| 521 | Cyclopropyl | Z1 | 2-$CH_3$ |
| 522 | Cyclopropyl | Z1 | 3-$CH_3$ (R) |

TABLE 4-continued

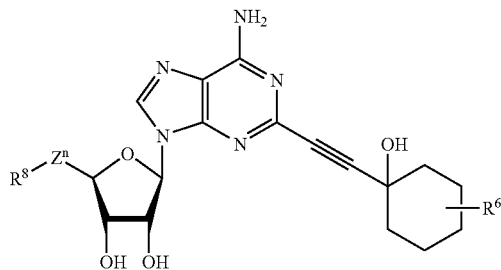

| Compound | R⁸ | Z | R⁶ |
| --- | --- | --- | --- |
| 523 | Cyclopropyl | Z1 | 3-CH₃ (S) |
| 524 | Cyclopropyl | Z1 | 3-Et (R) |
| 525 | Cyclopropyl | Z1 | 3-Et (S) |
| 526 | Cyclopropyl | Z1 | 4-Me |
| 527 | Cyclopropyl | Z1 | 4-Et |
| 528 | Cyclopropyl | Z1 | 4-Pr |
| 529 | Cyclopropyl | Z1 | 4-tBu |
| 530 | Cyclopropyl | Z1 | 4-Phenyl |
| 531 | Methyl | Z2 | 2-CH₃ |
| 532 | Methyl | Z2 | 3-CH₃ (R) |
| 533 | Methyl | Z2 | 3-CH₃ (S) |
| 534 | Methyl | Z2 | 3-Et (R) |
| 535 | Methyl | Z2 | 3-Et (S) |
| 536 | Methyl | Z2 | 4-Me |
| 537 | Methyl | Z2 | 4-Et |
| 538 | Methyl | Z2 | 4-Pr |
| 539 | Methyl | Z2 | 4-tBu |
| 540 | Methyl | Z2 | 4-Phenyl |
| 541 | Ethyl | Z2 | 2-CH₃ |
| 542 | Ethyl | Z2 | 3-CH₃ (R) |
| 543 | Ethyl | Z2 | 3-CH₃ (S) |
| 544 | Ethyl | Z2 | 3-Et (R) |
| 545 | Ethyl | Z2 | 3-Et (S) |
| 546 | Ethyl | Z2 | 4-Me |
| 547 | Ethyl | Z2 | 4-Et |
| 548 | Ethyl | Z2 | 4-Pr |
| 549 | Ethyl | Z2 | 4-tBu |
| 550 | Ethyl | Z2 | 4-Phenyl |
| 551 | Cyclopropyl | Z2 | 2-CH₃ |
| 552 | Cyclopropyl | Z2 | 3-CH₃ (R) |
| 553 | Cyclopropyl | Z2 | 3-CH₃ (S) |
| 554 | Cyclopropyl | Z2 | 3-Et (R) |
| 555 | Cyclopropyl | Z2 | 3-Et (S) |
| 556 | Cyclopropyl | Z2 | 4-Me |
| 557 | Cyclopropyl | Z2 | 4-Et |
| 558 | Cyclopropyl | Z2 | 4-Pr |
| 559 | Cyclopropyl | Z2 | 4-tBu |
| 560 | Cyclopropyl | Z2 | 4-Phenyl |
| 561 | Methyl | Z3 | 2-CH₃ |
| 562 | Methyl | Z3 | 3-CH₃ (R) |
| 563 | Methyl | Z3 | 3-CH₃ (S) |
| 564 | Methyl | Z3 | 3-Et (R) |
| 565 | Methyl | Z3 | 3-Et (S) |
| 566 | Methyl | Z3 | 4-Me |
| 567 | Methyl | Z3 | 4-Et |
| 568 | Methyl | Z3 | 4-Pr |
| 569 | Methyl | Z3 | 4-tBu |
| 570 | Methyl | Z3 | 4-Phenyl |
| 571 | Ethyl | Z3 | 2-CH₃ |
| 572 | Ethyl | Z3 | 3-CH₃ (R) |
| 573 | Ethyl | Z3 | 3-CH₃ (S) |
| 574 | Ethyl | Z3 | 3-Et (R) |
| 575 | Ethyl | Z3 | 3-Et (S) |
| 576 | Ethyl | Z3 | 4-Me |
| 577 | Ethyl | Z3 | 4-Et |
| 578 | Ethyl | Z3 | 4-Pr |
| 579 | Ethyl | Z3 | 4-tBu |
| 580 | Ethyl | Z3 | 4-Phenyl |
| 581 | Cyclopropyl | Z3 | 2-CH₃ |
| 582 | Cyclopropyl | Z3 | 3-CH₃ (R) |
| 583 | Cyclopropyl | Z3 | 3-CH₃ (S) |
| 584 | Cyclopropyl | Z3 | 3-Et (R) |
| 585 | Cyclopropyl | Z3 | 3-Et (S) |
| 586 | Cyclopropyl | Z3 | 4-Me |

TABLE 4-continued

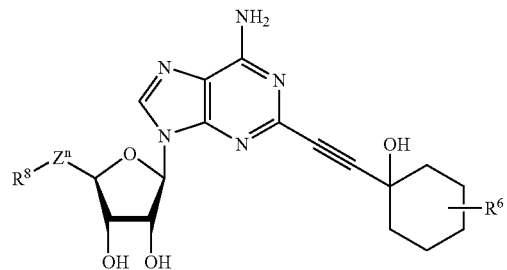

| Compound | R⁸ | Z | R⁶ |
| --- | --- | --- | --- |
| 587 | Cyclopropyl | Z3 | 4-Et |
| 588 | Cyclopropyl | Z3 | 4-Pr |
| 589 | Cyclopropyl | Z3 | 4-tBu |
| 590 | Cyclopropyl | Z3 | 4-Phenyl |
| 591 | Methyl | Z4 | 2-CH₃ |
| 592 | Methyl | Z4 | 3-CH₃ (R) |
| 593 | Methyl | Z4 | 3-CH₃ (S) |
| 594 | Methyl | Z4 | 3-Et (R) |
| 595 | Methyl | Z4 | 3-Et (S) |
| 596 | Methyl | Z4 | 4-Me |
| 597 | Methyl | Z4 | 4-Et |
| 598 | Methyl | Z4 | 4-Pr |
| 599 | Methyl | Z4 | 4-tBu |
| 600 | Methyl | Z4 | 4-Phenyl |
| 601 | Ethyl | Z4 | 2-CH₃ |
| 602 | Ethyl | Z4 | 3-CH₃ (R) |
| 603 | Ethyl | Z4 | 3-CH₃ (S) |
| 604 | Ethyl | Z4 | 3-Et (R) |
| 605 | Ethyl | Z4 | 3-Et (S) |
| 606 | Ethyl | Z4 | 4-Me |
| 607 | Ethyl | Z4 | 4-Et |
| 608 | Ethyl | Z4 | 4-Pr |
| 609 | Ethyl | Z4 | 4-tBu |
| 610 | Ethyl | Z4 | 4-Phenyl |
| 611 | Cyclopropyl | Z4 | 2-CH₃ |
| 612 | Cyclopropyl | Z4 | 3-CH₃ (R) |
| 613 | Cyclopropyl | Z4 | 3-CH₃ (S) |
| 614 | Cyclopropyl | Z4 | 3-Et (R) |
| 615 | Cyclopropyl | Z4 | 3-Et (S) |
| 616 | Cyclopropyl | Z4 | 4-Me |
| 617 | Cyclopropyl | Z4 | 4-Et |
| 618 | Cyclopropyl | Z4 | 4-Pr |
| 619 | Cyclopropyl | Z4 | 4-tBu |
| 620 | Cyclopropyl | Z4 | 4-Phenyl |
| 621 | Methyl | Z5 | 2-CH₃ |
| 622 | Methyl | Z5 | 3-CH₃ (R) |
| 623 | Methyl | Z5 | 3-CH₃ (S) |
| 624 | Methyl | Z5 | 3-Et (R) |
| 625 | Methyl | Z5 | 3-Et (S) |
| 626 | Methyl | Z5 | 4-Me |
| 627 | Methyl | Z5 | 4-Et |
| 628 | Methyl | Z5 | 4-Pr |
| 629 | Methyl | Z5 | 4-tBu |
| 630 | Methyl | Z5 | 4-Phenyl |
| 631 | Ethyl | Z5 | 2-CH₃ |
| 632 | Ethyl | Z5 | 3-CH₃ (R) |
| 633 | Ethyl | Z5 | 3-CH₃ (S) |
| 634 | Ethyl | Z5 | 3-Et (R) |
| 635 | Ethyl | Z5 | 3-Et (S) |
| 636 | Ethyl | Z5 | 4-Me |
| 637 | Ethyl | Z5 | 4-Et |
| 638 | Ethyl | Z5 | 4-Pr |
| 639 | Ethyl | Z5 | 4-tBu |
| 640 | Ethyl | Z5 | 4-Phenyl |
| 641 | Cyclopropyl | Z5 | 2-CH₃ |
| 642 | Cyclopropyl | Z5 | 3-CH₃ (R) |
| 643 | Cyclopropyl | Z5 | 3-CH₃ (S) |
| 644 | Cyclopropyl | Z5 | 3-Et (R) |
| 645 | Cyclopropyl | Z5 | 3-Et (S) |
| 646 | Cyclopropyl | Z5 | 4-Me |
| 647 | Cyclopropyl | Z5 | 4-Et |
| 648 | Cyclopropyl | Z5 | 4-Pr |

TABLE 4-continued

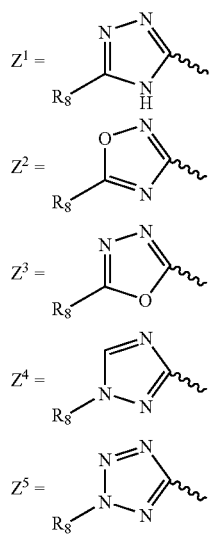

| Compound | R⁸ | Z | R⁶ |
|---|---|---|---|
| 649 | Cyclopropyl | Z5 | 4-tBu |
| 650 | Cyclopropyl | Z5 | 4-Phenyl |

$Z^1$ = [triazole structure with $R_8$]

$Z^2$ = [oxadiazole structure with $R_8$]

$Z^3$ = [oxadiazole structure with $R_8$]

$Z^4$ = [triazole structure with $R_8$]

$Z^5$ = [triazole structure with $R_8$]

The following abbreviations have been used herein:

| | |
|---|---|
| 2-Aas | 2-alkynyladenosines; |
| ¹²⁵I-ABA | N⁶-(4-amino-3-¹²⁵iodo-benzyl)adenosine |
| APCI | Atmospheric pressure chemical ionization |
| ATL146e | 4-{3-[6-Amino-9-(5-ethylcarbamoyl-3,4-dihydroxy-tetrahydro-furan-2-yl)-9H-purin-2-yl]-prop-2-ynyl}cyclohexanecarboxylic acid methyl ester; |
| CCPA | 2-chloro-N⁶-cyclopentyladenosine; |
| CGS21680 | 2-[4-(2-carboxyethyl)phenethylamino]-5'-N-ethyl-carboxamidoadenosine; |
| Cl-IB-MECA | N⁶-3-iodo-2-chlorobenzyladenosine-5'-N-methyluronamide; |
| CPA | N⁶-cyclopentyladenosine |
| DMF | dimethylformamide |
| DMSO | dimethylsulfoxide |
| DMSO-d₆ | deuterated dimethylsulfoxide |
| EtOAc | ethyl acetate |
| eq | equivalent |
| GPCR | G protein coupled receptor; hA₂ₐAR, Recombinant human A₂ₐ adenosine receptor; |
| IADO | 2-Iodoadenosine |
| ¹²⁵I-APE, | 2-[2-(4-amino-3-[¹²⁵I]iodophenyl)ethylamino]adenosine; NECA, 5'-N-ethylcarboxamidoadenosine; |
| IB-MECA | N⁶-3-iodobenzyladenosine-5'-N-methyluronamide; |
| 2-Iodoadenosine | 5-(6-amino-2-iodo-purin-9-yl)-3,4-dihydroxytetra-hydro-furan-2carboxylic acid ethylamide |
| HPLC | high-performance liquid chromatography |
| HRMS | high-resolution mass spectrometry |
| ¹²⁵I-ZM241385, | ¹²⁵I-4-(2-[7-amino-2-[2-furyl][1,2,4]triazolo[2,3-a][1,3,5]-triazin-5-yl-amino]ethyl)phenol; |
| INECA | 2-iodo-N-ethylcarboxamidoadenosine |
| LC/MS | liquid chromatography/mass spectrometry |
| m.p. | melting point |
| MHz | megahertz |
| MRS 1220, | N-(9-chloro-2-furan-2-yl-[1,2,4]triazolo[1,5-c]-quinazolin-5-yl)-2-phenylacetamide; |
| MS | mass spectrometry |
| NECA | N-ethylcarboxamidoadenosine |
| NMR | nuclear magnetic resonance |
| RP-HPLC | reverse phase high-performance liquid chromatography |
| TBAF | tetrabutylammonium fluoride |
| TBS | tert-butyldimethylsilyl |
| TBDMSCl | tert-butyldimethylsilylchloride |
| TEA | triethylamine |
| TFA | trifluoroacetic acid |
| THF | tetrahydrofuan |
| TLC | thin layer chromatography |
| p-TSOH | para-toluenesulfonic acid |
| XAC | 8-(4-((2-a-minoethyl)aminocarbonyl-methyloxy)-phenyl)-1-3-dipropylxanthine; |

Specific Type IV phosphodiesterase (PDE) inhibitors useful in practicing the instant invention include racemic and optically active 4-(polyalkoxyphenyl)-2-pyrrolidones of the following formula:

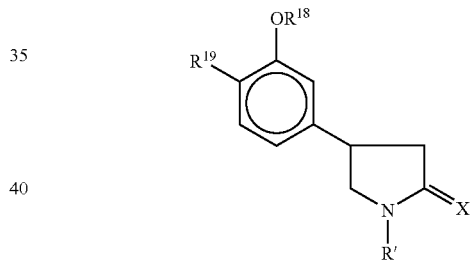

wherein RN, $R^{18}$, $R^{19}$ and X are as disclosed and described in U.S. Pat. No. 4,193,926. Rolipram is an example of a suitable Type IV PDE inhibitor included within the above formula.

Additional non-limiting examples of PDE IV inhibitors useful in practicing the instant invention include but are not limited to compounds having the following formulas and variations thereof.

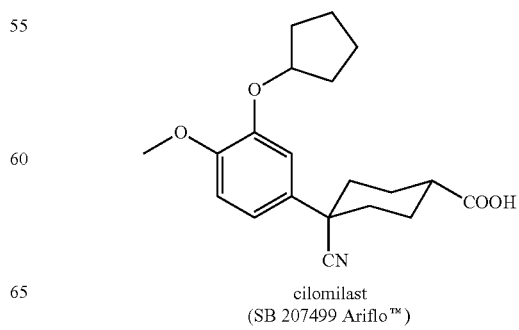

cilomilast
(SB 207499 Ariflo™)

-continued
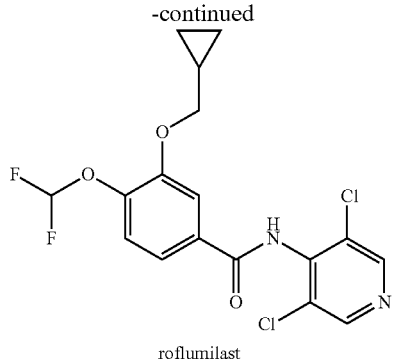
roflumilast
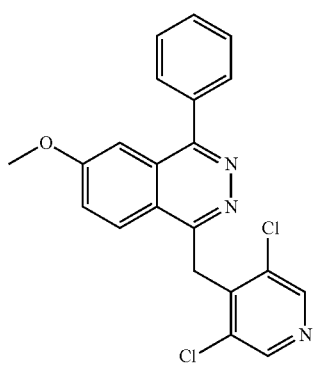
YM976
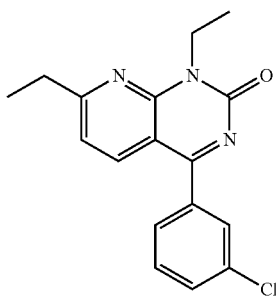
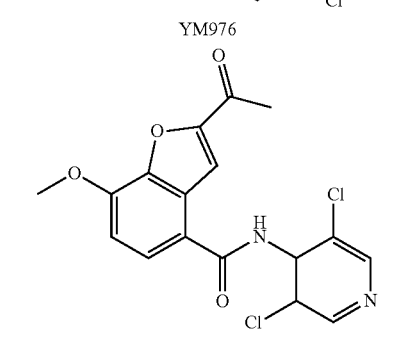
L-791, 943
-continued
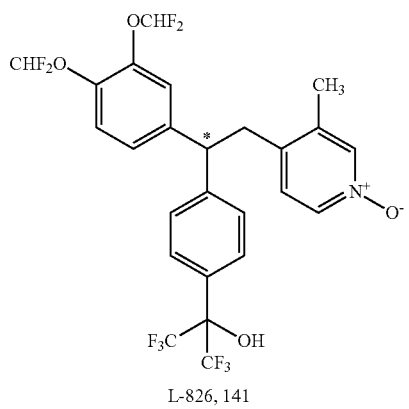
L-826, 141
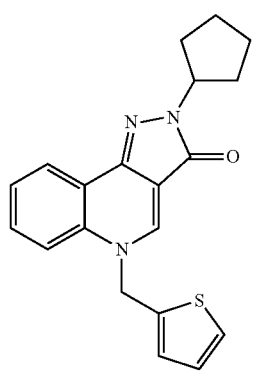
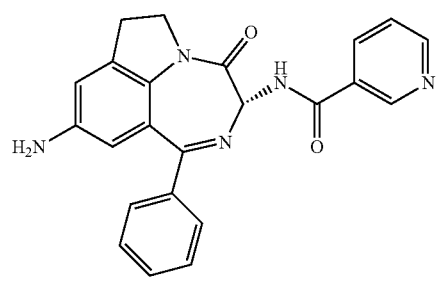
Cl-1004
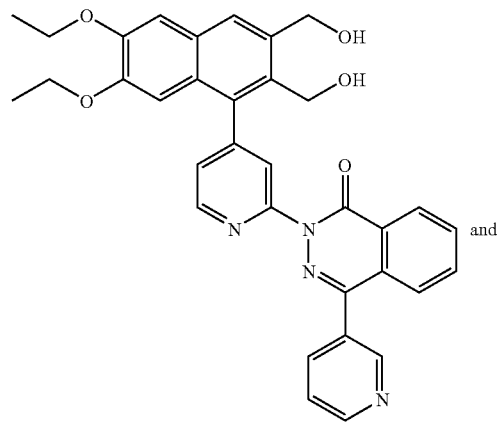 and
T-2585

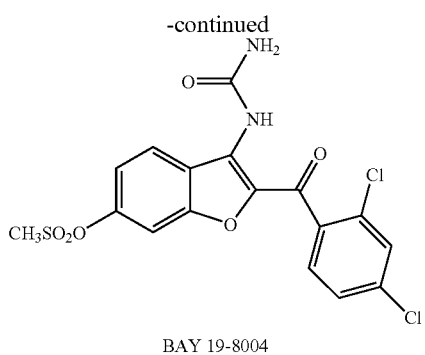

BAY 19-8004

The present invention further provides pharmaceutical compositions that include a compound of Formula (I) in combination with one of more members selected from the group consisting of the following: (a) Leukotriene biosynthesis inhibitors, 5-lipoxygenase (5-LO) inhibitors, and 5-lipoxygenase activating protein (FLAP) antagonists selected from the group consisting of zileuton; ABT-761; fenleuton; tepoxalin; Abbott-79175; Abbott-85761; N-(5-substituted)-thiophene-2-alkylsulfonamides of Formula (5.2.8); 2,6-di-tert-butylphenol hydrazones of Formula (5.2.10); Zeneca ZD-2138 of Formula (5.2.11); SB-210661 of Formula (5.2.12); pyridinyl-substituted 2-cyanonaphthalene compound L-739,010; 2-cyanoquinoline compound L-746,530; indole and quinoline compounds MK-591, MK-886, and BAY×1005; (b) Receptor antagonists for leukotrienes LTB4, LTC4, LTD4, and LTE4 selected from the group consisting of phenothiazin-3-one compound L-651,392; amidino compound CGS-25019c; benzoxazolamine compound ontazolast; benzenecarboximidamide compound BIIL 284/260; compounds zafirlukast, ablukast, montelukast, pranlukast, verlukast (MK-679), RG-12525, Ro-245913, iralukast (CGP 45715A), and BAY×7195; (d) 5-Lipoxygenase (5-LO) inhibitors; and 5-lipoxygenase activating protein (FLAP) antagonists; (e) Dual inhibitors of 5-lipoxygenase (5-LO) and antagonists of platelet activating factor (PAF); (f) Theophylline and aminophylline; (g) COX-1 inhibitors (NSAIDs); and nitric oxide NSAIDs; (h) COX-2 selective inhibitor rofecoxib; (i) Inhaled glucocorticoids with reduced systemic side effects selected from the group consisting of prednisone, predniso lone, flunisolide, triamcinolone acetonide, beclomethasone dipropionate, budesonide, fluticasone propionate, and mometasone furoate; (j) Platelet activating factor (PAF) antagonists; (k) Monoclonal antibodies active against endogenous inflammatory entities; (l) Anti-tumor necrosis factor (TNFαc) agents selected from the group consisting of etanercept, infliximab, and D2E7; (m) Adhesion molecule inhibitors including VLA-4 antagonists; (n) Immunosuppressive agents selected from the group consisting of cyclosporine, azathioprine, and methotrexate; or (O) anti-gout agents selected from the group consisting of colchicines.

Compounds of the invention can generally be prepared as illustrated in Schemes 1A and 1B below. Starting materials can be prepared by procedures described in these schemes, procedures described in the General methods below or by procedures that would be well known to one of ordinary skill in organic chemistry. The variables used in Schemes 1A and Scheme 1B are as defined herein or as in the claims.

The preparation of alkynyl cycloalkanols is illustrated in Scheme 1A. A solution of an appropriate cycloalkanone (where j is from 0-5) is prepared in a solvent such as THF. A solution of a suitable ethynylmagnesium halide compound in a solvent is added to the cycloalkanone. After addition, the solution is allowed to stir at about 20° C. for about 20 hours. The reaction is monitored via TLC until the starting material is consumed. The reaction is quenched with water, filtered over a plug of sand and silica, washed with a solvent, such as EtOAc, and evaporated to provide the product. Typically, two products are formed, the isomers formed by the axial/equatorial addition of the alkyne (where m is as defined above, and the sum of m1 and m2 is from 0 to about 7) to the ketone. The compounds are purified via flash chromatography using EtOAc/Hexanes to provide the product.

Scheme 1A
General Route to Synthesis of Alkyne Precursors

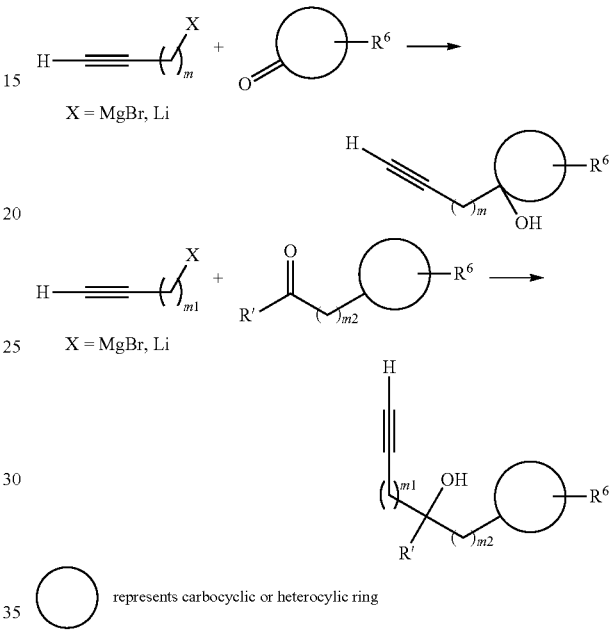

○ represents carbocyclic or heterocylic ring

The preparation of 2-alkynyladenosines is illustrated in Scheme 1B. A flame-dried round bottom under nitrogen is charged with 5-(6-Amino-2-iodo-purin-9-yl)-3,4-dihydroxytetrahydrofuran-2-carboxylic acid ethylamide(NECA 2-Iodoadenosine) and a solvent such as DMF. The appropriate alkyne, wherein R is a —$(CR^1R^2)_m$ Z group, is dissolved in acetonitrile followed by TEA, 5 mole % $Pd(PPh_3)_4$, and CuI. All solvents are thoroughly degassed.

The solution is allowed to stir for about 24 hours at room temperature, and monitored until complete by HPLC. If the reaction is not complete after this time, additional catalyst, CuI, and TEA are added. After the reaction is complete, the solvents are removed under high-vacuum and the residue taken up in a small amount of DMF. This product is isolated using preparative silica TLC. The product is purified by RP-HPLC.

Scheme 1B

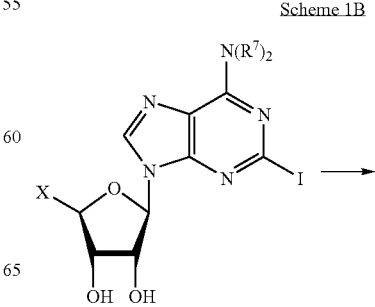

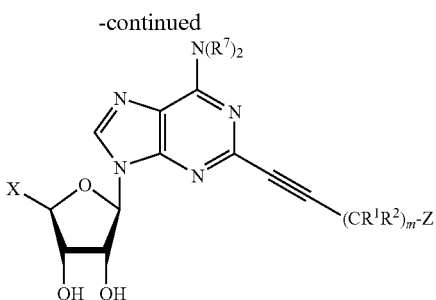

Examples of pharmaceutically acceptable salts are organic acid addition salts formed with acids that form a physiological acceptable anion, for example, tosylate, methanesulfonate, malate, acetate, citrate, malonate, tart rate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid, a liquid or in a dermatological patch.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions, which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949. Useful dosages of Type IV PDE inhibitors are known to the art. For example, see, U.S. Pat. No. 5,877,180, Col. 12.

Generally, the concentration of the compound(s) of formula (I) in a liquid composition, such as a lotion, will be from about 0.1-25% wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 μg/kg, e.g., from about 10 to about 75 μg/kg of body weight per day, such as 3 to about 50 μg per kilogram body weight of the recipient per day, preferably in the range of 6 to 90 μg/kg/day, most preferably in the range of 15 to 60 μg/kg/day.

The compound is conveniently administered in unit dosage form; for example, containing 5 to 1000 μg. conveniently 10 to 750 μg. most conveniently, 50 to 500 μg of active ingredient per unit dosage form.

Ideally, the active ingredient should be administered to achieve peak plasma concentrations of the active compound of from about 0.1 to about 10 nM, preferably, about 0.2 to 10 nM, most preferably, about 0.5 to about 5 nM. This may be achieved, for example, by the intravenous injection of a 0.05 to 5% solution of the active ingredient, optionally in saline, or orally administered as a bolus containing about 1-100 μg of the active ingredient. Desirable blood levels may be maintained by continuous infusion to provide about 0.01-5.0 μg/kg/hr or by intermittent infusions containing about 0.4-15 μg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. For example, it is desirable to administer the present compositions intravenously over an extended period of time following the insult that gives rise to inflammation.

The ability of a given compound of the invention to act as an $A_{2A}$ adenosine receptor agonist (or antagonist) may be determined using pharmacological models which are well known to the art, or using tests described below.

The present compounds and compositions containing them are administered as pharmacological stressors and used in conjunction with any one of several noninvasive diagnostic procedures to measure aspects of myocardial perfusion. For example, intravenous adenosine may be used in conjunction with thallium-201 myocardial perfusion imaging to assess the severity of myocardial ischemia. In this case, any one of several different radiopharmaceuticals may be substituted for thallium-201 (e.g., technetium-99m-labeled radiopharmaceuticals (ie: Tc-99m-sestamibi, Tc-99m-teboroxime), iodine-123-labeled radiopharmaceuticals such as I-123-IPPA or BMIPP, rubidium-82, nitrogen-13, etc. . . . ). Similarly, one of the present compounds may be administered as a pharmacological stressor in conjunction with radionuclide ventriculography to assess the severity of myocardial contractile dysfunction. In this case, radionuclide ventriculographic studies may be first pass or gated equilibrium studies of the right and/or left ventricle. Similarly, a compound of formula (I) may be administered as a pharmacological stressor in conjunction with echocardiography to assess the presence of regional wall motion abnormalities. Similarly, the active compound may be administered as a pharmacological stressor in conjunction with invasive measurements of coronary blood flow such as by intracardiac catheter to assess the functional significance of stenotic coronary vessels.

The method typically involves the administration of one or more compounds of formula (I) by intravenous infusion in doses which are effective to provide coronary artery dilation (approximately 0.25-500, preferably 1-250 mcg/kg/min). However, its use in the invasive setting may involve the intracoronary administration of the drug in bolus doses of 0.5-50 mcg.

Preferred methods comprise the use of a compound of formula (I) as a substitute for exercise in conjunction with myocardial perfusion imaging to detect the presence and/or assess the severity of coronary artery disease in humans wherein myocardial perfusion imaging is performed by any one of several techniques including radiopharmaceutical myocardial perfusion imaging using planar scintigraphy or single photon emission computed tomography (SPECT), positron emission tomograph (PET), nuclear magnetic resonance (NMR) imaging, perfusion contrast echocardiography, digital subtraction angiography (DSA), or ultrafast X-ray computed tomography (CINE CT).

A method is also provided comprising the use of a compound of formula (I) as a substitute for exercise in conjunction with imaging to detect the presence and/or assess the severity of ischemic ventricular dysfunction in humans wherein ischemic ventricular dysfunction is measured by any one of several imaging techniques including echocardiography, contrast ventriculography, or radionuclide ventriculography. The myocardial dysfunction can be coronary artery disease, ventricular dysfunction, differences in blood flow through disease-free coronary vessels and stenotic coronary vessels and the like A method is also provided comprising the use of a compound of formula (I) as a coronary hyperemic agent in conjunction with means for measuring coronary blood flow velocity to assess the vasodilatory capacity (reserve capacity) of coronary arteries in humans wherein coronary blood flow velocity is measured by any one of several techniques including Doppler flow catheter or digital subtraction angiography.

The invention will be further described by reference to the following detailed examples, which are given for illustration of the invention, and are not intended to be limiting thereof.

DESCRIPTION OF PREFERRED EMBODIMENTS

All melting points were determined with a Thomas Hoover capillary melting point apparatus and are uncorrected. Nuclear magnetic resonance spectra for proton ($^1$H NMR) were recorded on a 300 MHz GE spectrophotometer. The chemical shift values are expressed in ppm (parts per million) relative to tetramethylsilane. For data reporting, s=singlet, d=doublet, t=triplet, q=quartet, and m=multiplet. Mass spectra were measured on a Finnigan LcQ Classic. High resolution mass spectrometry (HRMS) data was provided by the Nebraska Center for Mass Spectrometry. Analytical HPLC was done on a Waters 2690 Separation Module with a Waters Symmetry C8 (2.1×150 mm) column operated at room temperature. Compounds were eluted at 200 µL/min with 70:30 acetonitrile:water, containing 0.5% acetic acid, with UV detection at 214 nm using a Waters 486 Tunable Detector. Preparative HPLC was performed on a Shimadzu Discovery HPLC with a Shim-pack VP-ODS $C_{18}$ (20×100 mm) column operated at room temperature. Compounds were eluted at 30 mL/min with a gradient 20-80% of water (containing 0.1% TFA) to methanol over 15 minutes with UV detection at 214 nm using a SPD10A VP Tunable detector. All final compounds presented here were determined to be greater than 98% pure by HPLC. Flash chromatography was performed on Silicyle 60A gel (230-400 mesh) or using reusable chromatography columns and system from RT Scientific, Manchester N.H. Analytical thin-layer chromatography was done on Merck Kieselgel 60 F254 aluminum sheets. Preparative thin-layer chromatography was done using 1000 micron Analtech Uniplate with silica gel. All reactions were done under a nitrogen atmosphere in flame-dried glassware unless otherwise stated.

General Method 1: Preparation of Alkynyl Cyclohexanols

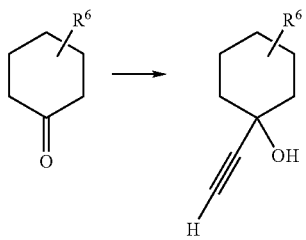

To a solution of 10 mmol of the appropriate cyclohexanone in 50 mL of THF was added 60 mL (30 mmol) of 0.5 M ethynylmagnesium bromide in THF. The solution was allowed to stir at 20° C. for 20 h, at which time TLC indicated that all the starting material had been consumed. The reaction was quenched with 5 mL of water, filtered over a plug of sand and silica, washed with EtOAc, and evaporated to yield a yellow oil usually containing two spots on TLC w/20% EtOAc/Hexanes which were visualized with Vanillin. These two products were usually the different isomers formed by the axial/equatorial addition of the alkyne to the ketone. The compounds were purified via flash chromatography using 10% EtOAc/Hexanes to yield clear oils or white solids in 50-80% yields.

General Method 2: Preparation of Propargyl Piperadines and Piperazines

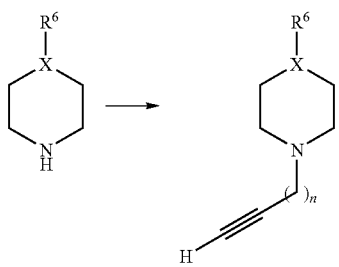

X = CH, N

To a solution of 10.0 mmol of the appropriate piperazine or piperadine in 20 mL acetonitrile were added 12.0 mmol of propargyl bromide (80% stabilized in toluene) and 50.0 mmol of anhydrous potassium carbonate. The reaction mixture was filtered, and evaporated to dryness. The residue was taken up in 50 mL of dichloromethane/water and the organic removed. The aqueous was washed with an additional 3×25 mL dichloromethane. The organic was then dried using anhydrous sodium sulfate, filtered, and concentrated to yield crude product which was purified using column chromatography.

General Method 3: Preparation of Modified Piperadines and Piperazines

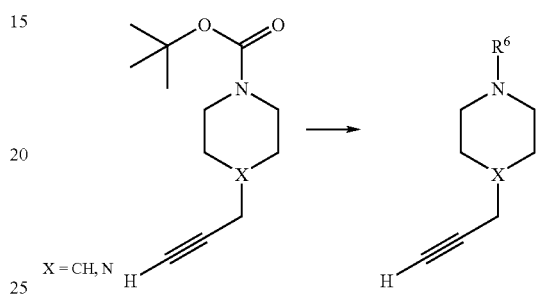

X = CH, N

To 100 mg of the appropriate Boc-protected piperazine or piperadine, JR3275/JR3255 respectively, was added 2-4 mL of neat TFA. The solution was allowed to stir for 6 hours, after which time the TFA was removed under reduced pressure to yield a yellow oil. This oil was taken up in 10 mL of dichloromethane to which was added 10-fold excess of TEA and 3 equivalents of the appropriate electrophile. The yellow solution was allowed to stir at r.t. for 12 hours, after which time the solvents were removed and the product purified using a 1.1× 30 cm 14 g RTSI column with a 5%-30% gradient of ethyl acetate/hexanes.

General Method 4: Preparation of 2-AAs (2-alkynyladenosines)

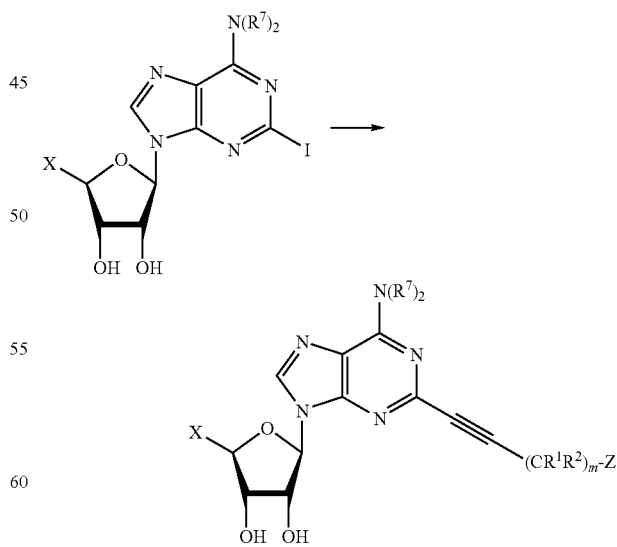

A flame dried 25 mL round bottom under nitrogen was charged with 2-Iodo adenosine analog (40 mg) and dissolved in 2 mL of DMF. The appropriate alkyne (approx 0.1 mL) was then added followed by 4 mL of acetonitrile and 0.1 mL of TEA. All three solvents had been degassed with nitrogen for at least 24 hours. To this solution was added 5 mole percent Pd(PPh$_3$)$_4$ and 6 mole % copper iodide. The yellowish solution was allowed to stir for 24 hours at room temperature, or until complete by HPLC. If the reaction was not complete at this time, additional catalyst, CuI, and TEA were added. After the reaction was complete, the solvents were removed under high-vacuum and the red/black residue taken back up in a small amount of DMF. This solution was added to a preparative silica TLC plate (Analtech 1000 microns, 20 cm×20 cm) and eluted first with 120 mL of 40% Hexanes/CH$_2$Cl$_2$, and then again after addition of 40 mL of MeOH. The UV active band (usually yellow in color) in the middle of the plate is collected, slowly washed with 4×25 mL 20% MeOH/CH$_2$Cl$_2$, and concentrated. This product is then purified by RP-HPLC to yield solids after trituration with anhydrous ethyl ether.

Scheme 1: Preparation of 5′ ester analogs:

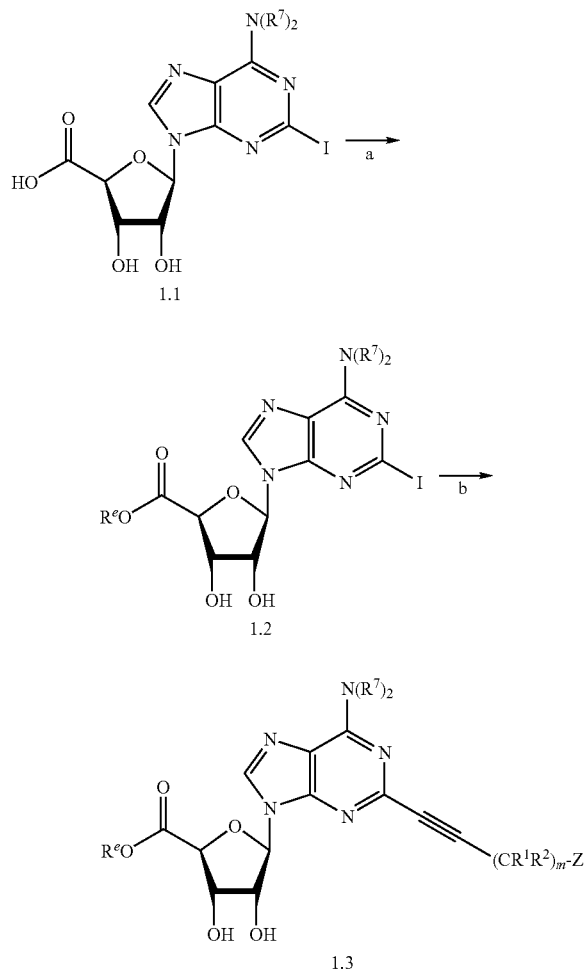

a) SOCl$_2$, R$^e$OH  b) Pd(PPH$_3$)$_4$, CuI, TEA, DMF, CH$_3$CN, alkyne

To a cooled solution of compound 1.1 in alcohol is added about 5 equivalents of ice-cooled thionyl chloride. This solution is allowed to stir, gradually coming to room temperature for about 12 hours. The solvent is then removed en vacuo to yield 1.2 as a white solid. This solid is then treated according to general method 4 to yield compound 1.3.

Scheme 2: Preparation of 5′ amide analogs:

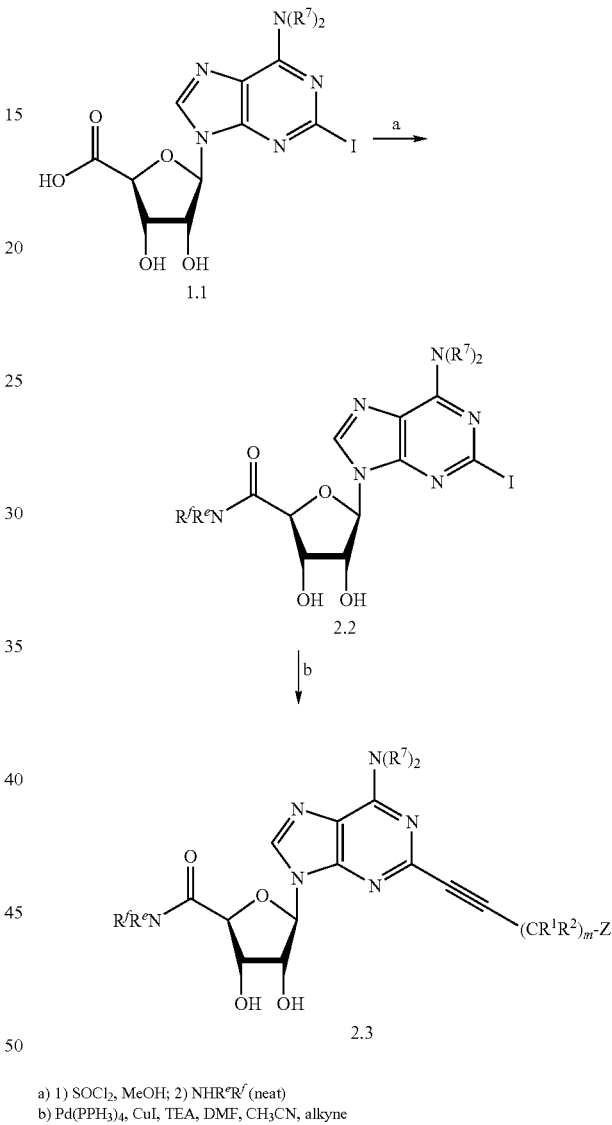

a) 1) SOCl$_2$, MeOH; 2) NHR$^e$R$^f$ (neat)
b) Pd(PPH$_3$)$_4$, CuI, TEA, DMF, CH$_3$CN, alkyne To a cooled solution of compound 1.1 in methanol is added about 5 equivalents of ice-cooled thionyl chloride. This solution is allowed to stir, gradually coming to r.t for about 12 hours. The solvent is then removed en vacuo to yield compound 1.2, which is dissolved in the appropriate amine(N-HR$_a$R$_b$) at 0° C. and allowed to stir for several hours or until complete. The solvent is then removed under vacuum and the product purified via crystallization or chromatography using a gradient of methanol and dichloromethane to afford 2.2 as a white solid. This solid is then treated according to general method 4 to yield compound 2.3.

Scheme 3: Preparation of 4' triazoles:

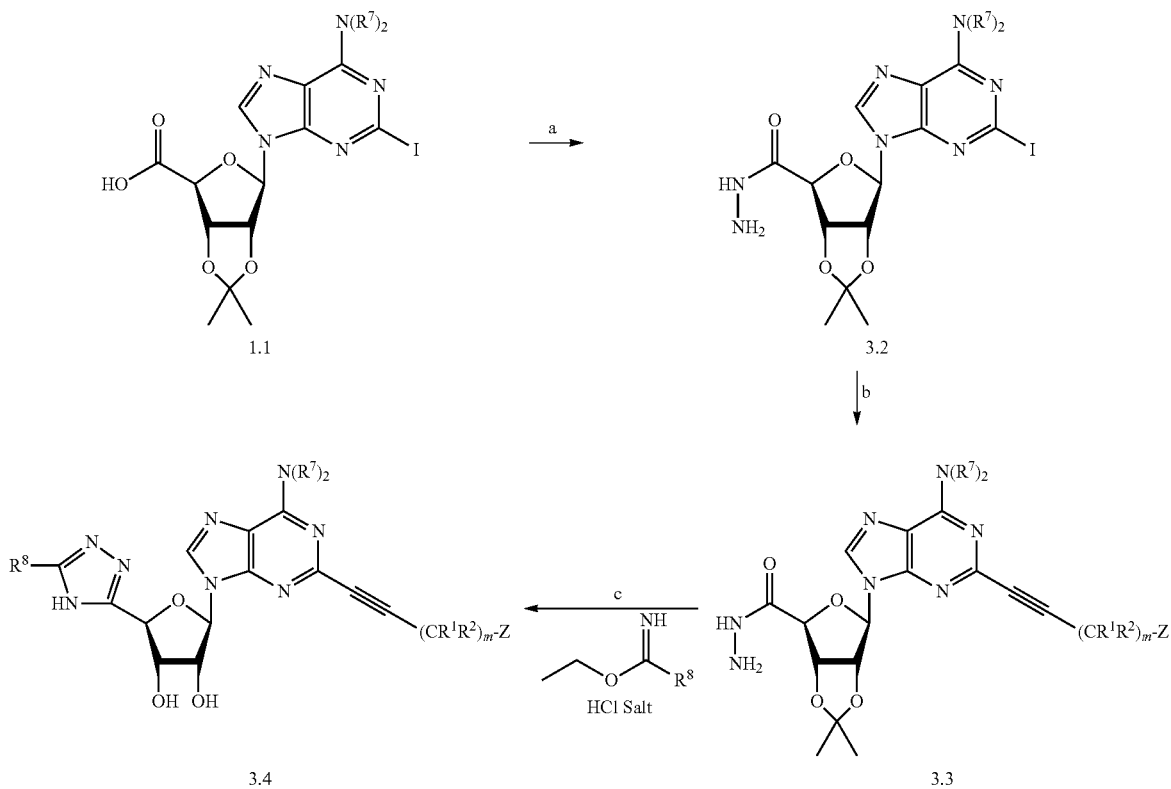

a) HBTU, DIPEA, DMF, H$_2$NNNH$_2$ H$_2$O b) Pd(PPH$_3$)$_4$, CuI, TEA, DMF, CH$_3$CN, alkyne
c) 1) EtOH, 80 C.; 2) Formic Acid, 50%

Hydrazine hydrate (1 equiv) is added to a stirred solution of 1.1 (1 equiv) in dry DMF, HBTU (1 equiv) and DIEA (2.5 equiv) and the solution is allowed to stir for about 24 hours. After extractive work-up, 3.2 can be isolated. 3.2 can be treated according to general method 4 to afford 3.3 which can then be dissolved in EtOH and treated with ethylacetimidate hydrochloride and TEA and refluxed for about 16 h to yield 3.4 after chromatography and deprotection using 50% formic acid for 6 h.

Scheme 4: Preparation of 4'-1,2,4-oxadiazoles

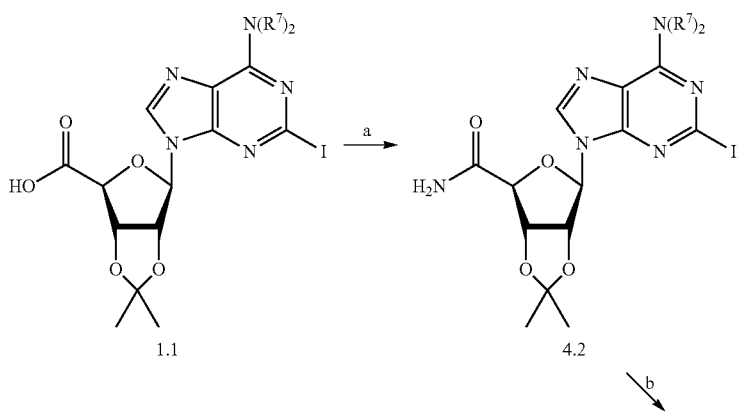

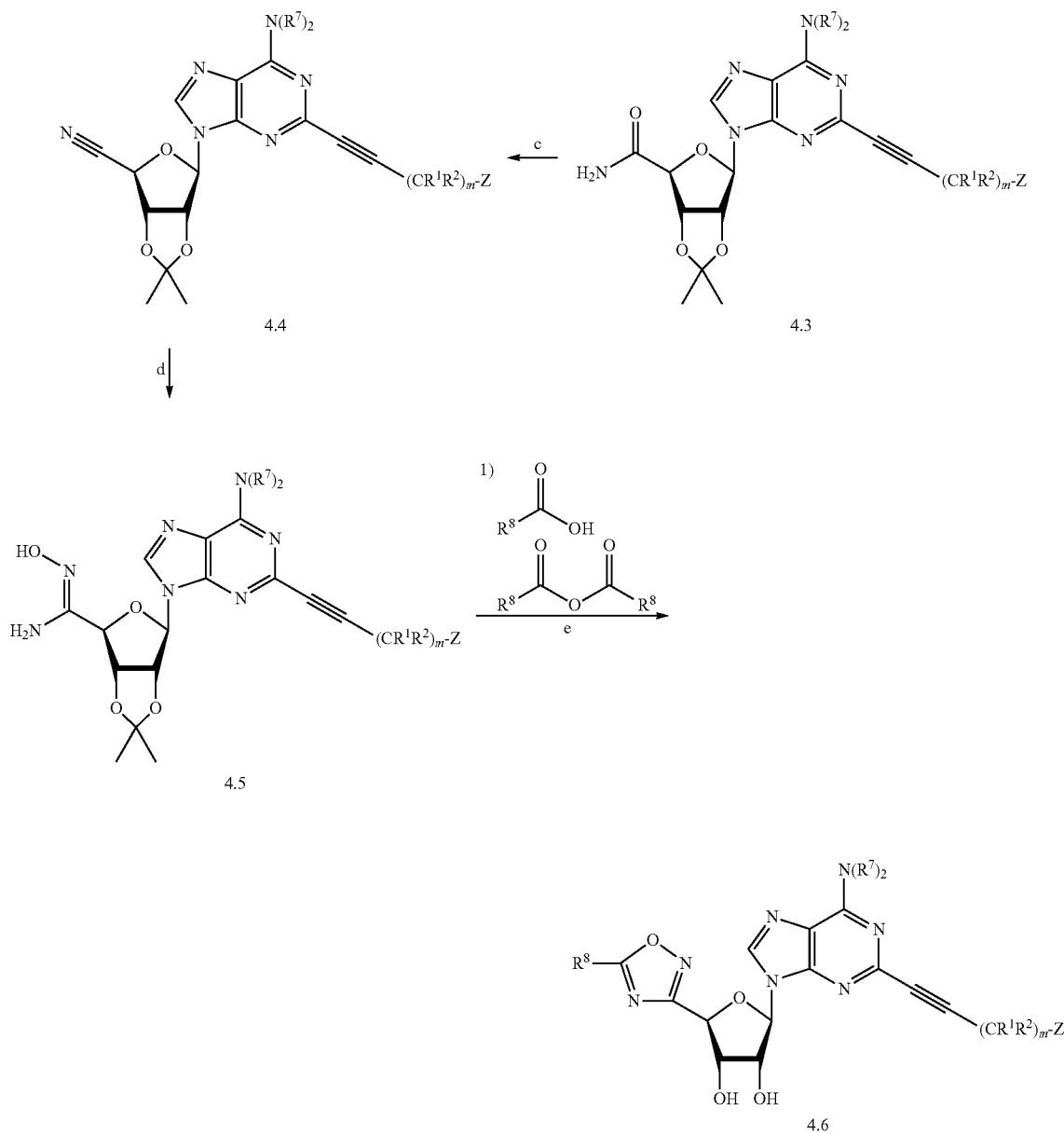

a) 1) TEA, CH$_2$Cl$_2$, pivaloyl chloride, 0 C.; 2) ammonia b) Pd(PPH$_3$)$_4$, CuI, TEA, DMF, CH$_3$CN, alkyne c) TEA, DMAP, CH$_3$CN, DMF, POCl$_3$ d) NH$_2$OH HCl, K$_2$CO$_3$, EtOH, 80 C. e) 1) 90 C. 2) 50% formic acid, 60 C.

Pivaloyl chloride is added to a cooled solution of 1.1 in DCM and TEA and allowed to stir for several hours. Ammonia gas is the bubbled through the solution to afford 4.2 after isolation and purification. 4.2 can be treated according to general method 4 to afford 4.3 which is then taken up in anhydrous acetonitrile and TEA and DMAP are added. To the ice-cooled solution is cautiously added POCl$_3$. After stirring for about 30 minutes, DMF is added to the solution and the mixture heated to 95 C for about 24 h. Purification affords 4.4, to which is added potassium carbonate and hydroxylamine hydrochloride after dissolution in EtOH. This solution is refluxed for about 24 h to yield 4.5 after purification. Treatment of 4.5 with the appropriate carboxylic acid/anhydride pair affords 4.6 after reflux and deprotection using 50% formic acid.

Scheme 5: Preparation of 4'-1,3,4 oxadiazoles

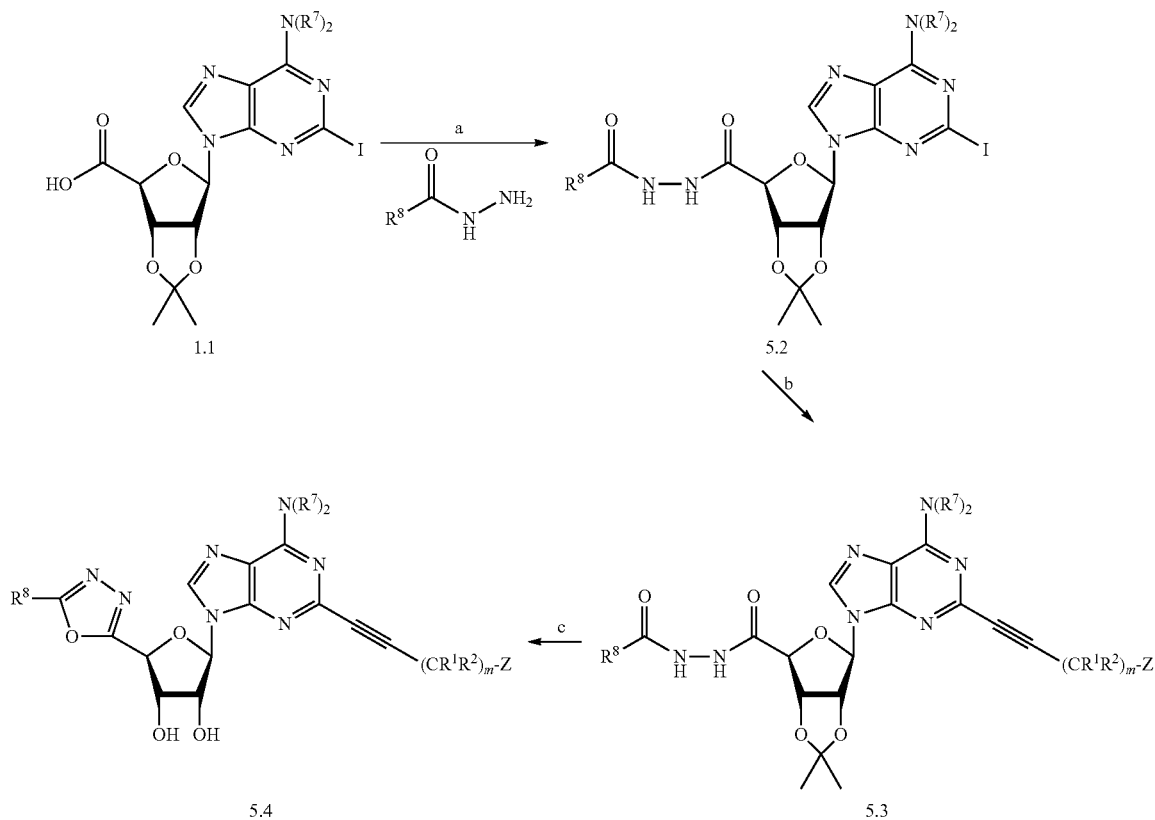

a) 1) DIEA, THF, pivaloyl chloride, 0 C.; 2) THF, 3 days b) Pd(PPH$_3$)$_4$, CuI, TEA, DMF, CH$_3$CN, alkyne c) 1) DMF, POCl$_3$ 2) 50% formic acid, 60 C.

Pivaloyl chloride is added to a solution of 1.1 in THF and DIEA at 0° C. After stirring for several hours the appropriate hydrazide is added and the mixture allowed to stir for about 3 days to yield 5.2. This product can be treated according to general method 4 to afford 5.3 which is dissolved in DMF and treated with POCl$_3$ at 0° C. for several hours to yield 5.4 after purification and deprotection with 50% formic acid.

Scheme 6: Preparation of 4'-1,3 oxazole

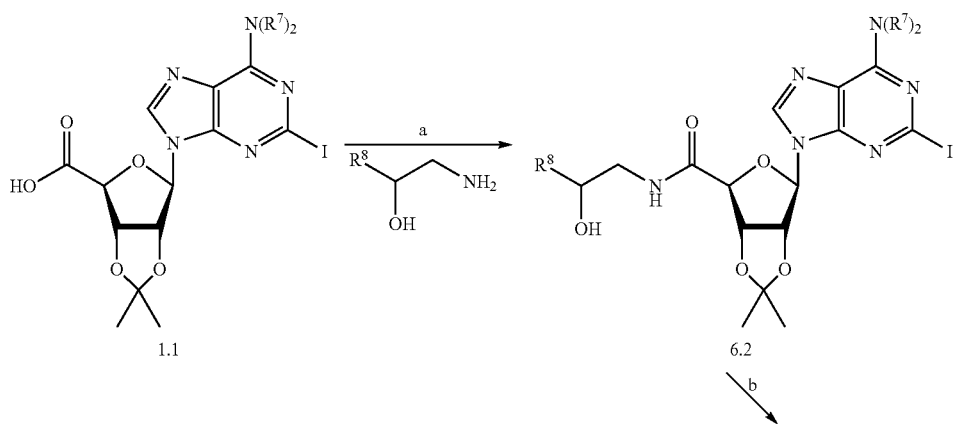

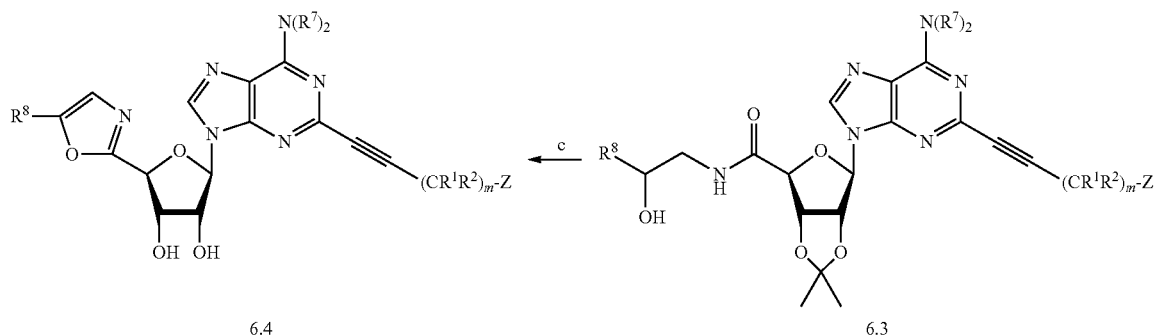

a) 1) DIEA, DCM, pivaloyl chloride, 0 C.; 2) THF, b) Pd(PPH₃)₄, CuI, TEA, DMF, CH₃CN, alkyne c) 1) PDC, DCM, 4A sieves, AcOH; 2) POCl₃, Toluene, Reflux; 3) 50% formic acid, 60 C.

Pivaloyl chloride is added to a solution of 1.1 in DCM and DIEA at 0° C. After stirring for several hours the appropriate 1,2-hydroxylamine is added and the mixture allowed to stir for about 24 h to yield 6.2. This product can be treated according to general method 4 to afford 6.3. This product is dissolved in DCM and treated with PDC, 4 Å molecular sieves, and AcOH to convert the alcohol to the ketone. This intermediate is then converted to 6.4 by reflux in toluene after treatment with POCl₃ and subsequent heating in 50% formic acid for 6 h Scheme 7: Preparation of 4'-1,3,4 thiadiazole

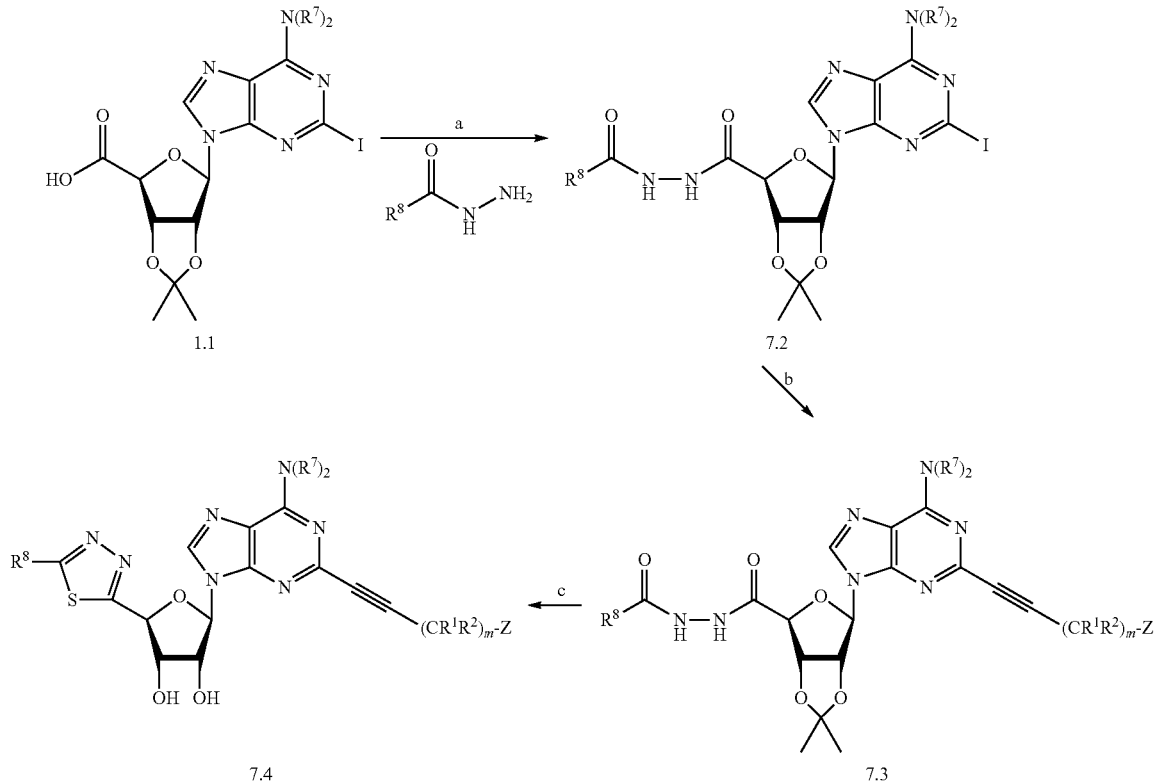

a) 1) DIEA, THF, pivaloyl chloride, 0 C.; 2) DMF, r.t. 3 h b) Pd(PPH₃)₄, CuI, TEA, DMF, CH₃CN, alkyne c) 1) Lawessons reagent, CH₃CN, 50 C., 18 h; 2) 50% formic acid, 60 C.

Pivaloyl chloride is added to a solution of 1.1 in THF and DIEA at 0° C. After stirring for several hours the appropriate hydrazide is added and the mixture is allowed to stir for several additional hours to yield 7.2. This product can be treated according to general method 4 to afford 7.3 which is dissolved in acetonitrile and treated with Lawessons reagent at 50° C. for about 1 day to yield 7.4 after purification and deprotection with 50% formic acid for 6 hours.

Scheme 8: Preparation of 4′-tetrazole

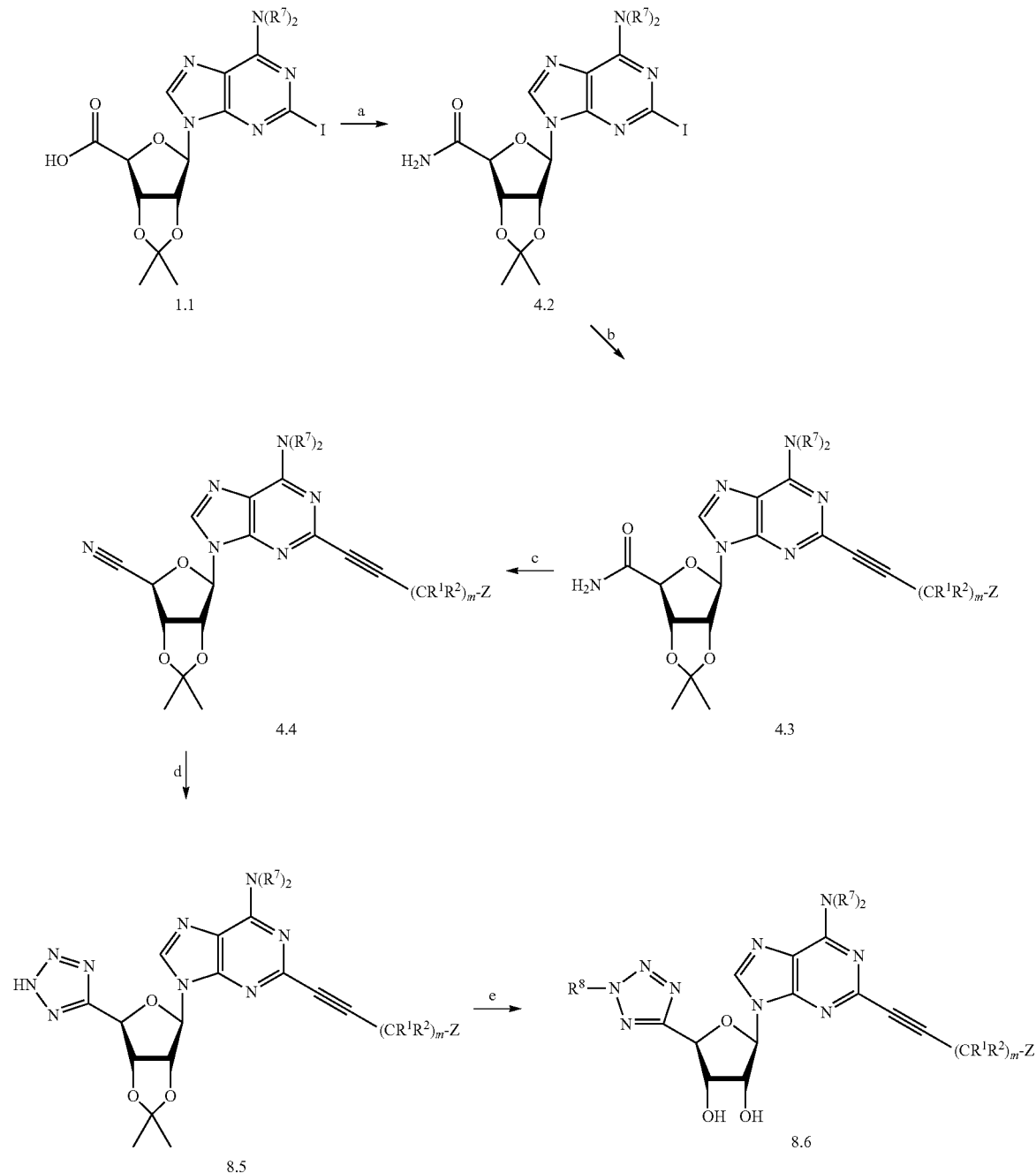

a) 1) TEA, CH$_2$Cl$_2$, pivaloyl chloride, 0 C.; 2) ammonia b) Pd(PPH$_3$)$_4$, CuI, TEA, DMF, CH$_3$CN, alkyne c) TEA, DMAP, CH$_3$CN, DMF, POCl$_3$ d) TMSN$_3$, toluene e) 1) R$_a$I, K$_2$CO$_3$, DMF; 2) 50% formic acid, 60 C.

Pivaloyl chloride is added to a cooled solution of 1.1 in DCM and TEA and allowed to stir for several hours. Ammonia gas is the bubbled through the solution to afford 4.2 after isolation and purification. 4.2 is then taken up in anhydrous acetonitrile and TEA and DMAP are added. To the ice-cooled solution is cautiously added POCl$_3$. After stirring for about 30 minutes, DMF is added to the solution and the mixture heated to 95 C for about 24 h. Purification affords 4.4, to which is added toluene, azidotrimethylsilane, and dibutyltin oxide and the mixture is heated to 6° C. for about 15 hours to afford 8.5. Treatment of 8.5 with the appropriate alkyl halide and potassium carbonate affords 8.6 after reflux and deprotection with 50% formic acid for 6 h.

Preparation 1: [4-(tert-Butyl-dimethyl-silanyloxymethyl)-cyclohexyl]-methanol (83)

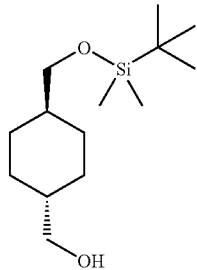

To a 100 mL-flask containing 79 (4.0 g, 27.8 mmol) in DMF (40 mL) was added TBDMSCl (3.56 g, 23.6 mmol) and imidazole (3.79 g, 55.6 mmol). The reaction was allowed to stir at 25° C. for 16 hours after which time saturated aqueous LiBr (50 mL) was added and the reaction extracted with ether (2×50 mL). The ether layers were pooled and extracted again with LiBr (2×35 mL). The ether layer became clear. The ether layer was then concentrated in vacuo and the product purified by flash chromatography, on a silica gel column, eluting with 1:2 ether/petroleum ether to yield 83 (3.80 g, 62%) as a homogenous oil. $^1$H NMR (CDCl$_3$) δ 3.46 (d, J=6.2 Hz, 2H), 3.39 (d, J=6.2 Hz, 2H), 1.95-1.72 (m, 4H), 1.65 (m, 1H), 1.40 (m, 1H), 1.03-0.89 (m, 4H), 0.88 (s, 9H), 0.04 (s, 6H); $^{13}$C NMR (CDCl$_3$) δ 69.2, 69.1, 41.2, 41.1, 29.5, 26.5, 18.9, −4.8; APCI m/z (rel intensity) 259 (MH$^+$, 100).

Preparation 2: Toluene-4-sulfonic acid 4-(tert-butyl-dimethyl-silanyloxymethyl)-cyclohexylmethyl ester (84)

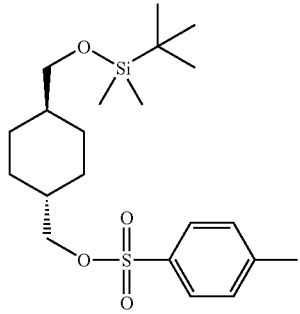

To a 100 mL-flask containing 83 (3.4 g, 13.2 mmol) in CHCl$_3$ (30 µL) was added tosyl chloride (3.26 g, 17.1 mmol) and pyridine (3.2 mL, 39.6 mmol). The reaction was allowed to stir at 25° C. for 14 hours after which time the reaction was concentrated in vacuo to yield a wet white solid. To this solid was added ether (50 mL) and the solid was filtered and subsequently washed with additional ether (2×50 mL). The ether layers were pooled, concentrated in vacuo to yield a clear oil which was purified by flash chromatography, on a silica gel column, eluting with 1:4 ether/petroleum ether to yield 84 (4.5 g, 83%) as a white solid. $^1$H NMR (CDCl$_3$) δ 7.78 (d, J=7.7, 2H), 7.33 (d, J=7.7 Hz, 2H), 3, 81 (d, J=6.2 Hz, 2H), 3.37 (d, J=6.2 Hz, 2H), 2.44 (s, 3H), 1.95-1.72 (m, 4H), 1.65 (m, 1H), 1.40 (m, 1H), 1.03-0.89 (m, 4H), 0.88 (s, 9H), 0.04 (s, 6H); $^{13}$C NMR (CDCl$_3$) δ 145.1, 133.7, 130.3, 128.4, 75.8, 68.9, 40.7, 38.0, 29.1, 26.5, 22.1, 18.9, −4.9; APCI m/z (rel intensity) 413 (MH$^+$, 100).

Preparation 3: (4-Prop-2-ynyl-cyclohexyl)-methanol (86)

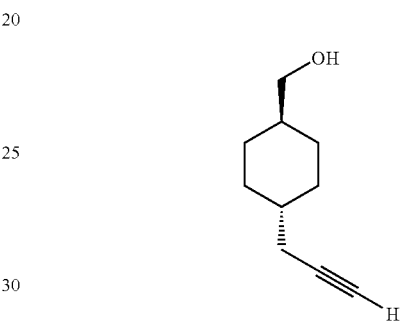

A 3-neck 250 mL-flask equipped with a gas inlet tube and dry-ice condenser was cooled to −78° C. and charged with liquid ammonia (40 mL). To the reaction mixture was added lithium wire (600 mg, 86.4 mmol) generating a deep blue solution. The mixture was allowed to stir for 1 hour. Acetylene, passed through a charcoal drying tube, was added to the ammonia until all the lithium had reacted and the solution turned colorless, at which time the flow of acetylene was stopped, the acetylene-inlet tube and condenser removed and the flask outfitted with a thermometer. DMSO (20 mL) was added and the ammonia evaporated with a warm water bath until the mixture reached a temperature of 30° C. The solution was stirred at this temperature for 2 hours until the solution stopped bubbling. The mixture was cooled to 5° C. and compound 84 (11.25 g, 27.3 mmol), in DMSO (10 mL), was added. The temperature was maintained at 5° C. The mixture was allowed to stir at 5° C. for 0.5 hours. Then the solution was gradually warmed to room temperature and stirred for an additional 18 hours. The brown/black reaction mixture was poured slowly over ice (300 g) and extracted with ether (4×100 mL), dried with anhydrous sodium sulfate, and concentrated in vacuo to yield a yellow oil. The oil was subsequently dissolved in THF (200 mL) and changed to a brownish color upon addition of TBAF hydrate (11.20 g, 35.5 mmol). The solution was allowed to stir for 24 hours 2 under N$_2$ atmosphere. After stirring, the reaction was quenched with water (200 mL) and extracted with ether (3×100 mL). The ether extracts were combined and concentrated in vacuo. The crude product was purified by chromatography, on a silica gel column, eluting with 1:1 ether/petroleum ether to yield 86 (3.91 g, 93%) as a yellow oil. $^1$H NMR (CDCl$_3$) δ 3.45 (d, J=6.2, 2H), 2.10 (d, J=6.2, 2H), 1.9 (s, 1H), 1.94-1.69 (m, 4H), 1.52-1.34 (m, 2H), 1.16-0.83 (m, 4H); $^{13}$C NMR (CDCl$_3$) δ 83.8, 69.5, 69.0, 40.8, 37.7, 32.3, 29.7, 26.5.

Preparation 4: (4-prop-2-ynylcyclohexyl)methyl acetate (87)

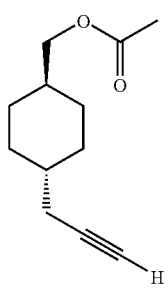

To a solution of 960 mg (6.31 mmol) of 86 in 6 mL DMF was added 0.62 mL (7.57 mmol) pyridine and 0.78 mL (8.27 mmol) acetic anhydride. The reaction was allowed to stir overnight at room temperature. After 16 hours, starting material still remained. The reaction mixture was heated at 75° C. for 3 hours. The solvent was removed under reduced pressure to yield a yellow oil which was purified by flash chromatography, on silica gel, eluting with 1:3 ether/petroleum ether to yield 1.12 g (91%) of 87 as an oil. $^1$H NMR (CDCl$_3$) δ 3.87 (d, J=6.2 Hz, 2H), 2.06 (d, J=4.3 Hz, 2H), 2.03 (s, 3H), 1.98-1.93 (m, 1H), 1.92-1.83 (m, 2H), 1.83-1.74 (m, 2H), 1.63-1.36 (m, 2H), 1.12-0.90 (m, 4H); $^{13}$C NMR (CDCl$_3$) δ 171.7, 83.7, 69.9, 69.6, 37.4, 37.3, 32.1, 29.7, 26.5, 21.4; APCI m/z (rel intensity) 195 (M$^+$, 30), 153 (M$^+$, 70), 135 (M$^+$, 100).

Preparation 5: 4-prop-2-ynyl-cyclohexanecarboxylic acid (88)

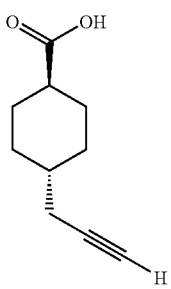

A solution of chromium trioxide (600 mg, 6.0 mmol) in 1.5 M H$_2$SO$_4$ (2.6 mL, 150 mmol) was cooled to 5° C. and added to a solution of 86 (280 mg, 1.84 mmol) in acetone (15 mL). The mixture was allowed to warm to room temperature and allowed to stir overnight. Isopropanol (4 mL) was added to the green/black solution, which turned light blue after 1 hr. After adding water (15 mL), the solution was extracted with CHCl$_3$ (6×25 mL). The organic layers were pooled and concentrated in vacuo to yield a white solid. The solid was dissolved in ether (50 mL) and extracted with 1 M NaOH (2×30 mL). The basic extracts were pooled, acidified w/10% HCl, and re-extracted with ether (3×30 mL). The ether layers were combined, dried with sodium sulfate and concentrated in vacuo to yield a white solid. The product was recrystallized from acetone/water to yield 88 (222 mg, 73%) as white needles: mp 84-85° C.; $^1$H NMR (CDCl$_3$) δ 2.30-2.23 (m, 1H), 2.17-2.11 (m, 2H), 2.07-2.03 (m, 2H), 1.97-1.91 (m, 3H), 1.51-1.39 (m, 3H), 1.13-1.01 (m, 2H); $^{13}$C NMR (CDCl$_3$) δ 182.5, 83.8, 69.6, 40.7, 37.7, 32.3, 29.6, 26.5; APCI m/z (rel intensity) 165 (M$^-$, 100).

Preparation 6: Methyl 4-prop-2-ynylcyclohexanecarboxylate (89)

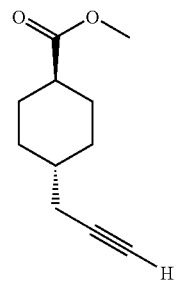

To a solution of 88 (240 mg, 1.45 mmol) in 7:3 CH$_2$Cl$_2$:MeOH (10 mL) was added TMS Diazomethane (2.0 M in hexanes) (0.9 mL, 1.8 mmol) in 0.2 ml aliquots until the color remained yellow. The reaction was allowed to stir for an additional 0.25 hours at room temperature. After stirring, glacial acetic acid was added dropwise until the solution became colorless. The reaction was concentrated in vacuo to an oil which was purified by flash chromatography on silica gel using ether:petroleum ether (1:9) to yield 89 (210 mg, 80%) as a clear oil. $^1$H NMR (CDCl$_3$) δ 3.60 (s, 3H), 2.25-2.13 (m, 1H), 2.08-1.94 (m, 3H), 1.95-1.90 (m, 2H), 1.49-1.31 (m, 3H), 1.10-0.93 (m, 2H); $^{13}$C NMR (CDCl$_3$) δ 176.7, 83.3, 69.8, 51.9, 43.4, 36.7, 31.9, 29.2, 26.3; APCI m/z (rel intensity) 181 (MH$^+$, 100).

Preparation 7: Trans[4-(1-Propargyl)cyclohexylmethyl]methyl carbonate (90)

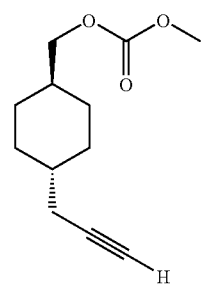

Yield: 345 mg, 81%. $^1$H NMR (CDCl$_3$) δ 0.98-1.07, 1.40-1.52, 1.57-1.70, 1.78-1.93 (4×m, 10H, cyclohexyl), 1.96 (t, 1H, acetylene), 2.10 (dd, 2H, —C$_6$H$_{10}$CH$_2$CCH), 3.78 (s, 3H, —OCH$_3$), 3.96 (d, —C$_6$H$_{10}$CH$_2$O—).

Preparation 8: Trans[4-(1-Propargyl)cyclohexylmethyl] iso-butyl carbonate (91)

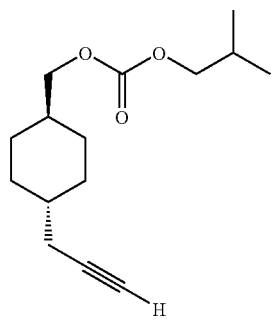

Yield: 433 mg, 83%. $^1$H NMR (CDCl$_3$) δ 0.95 (d, 4H, —OCH$_2$CH(CH$_3$)$_2$), 0.98-1.09, 1.40-1.51, 1.57-1.70, 1.78-

1.93 (4×m, 10H, cyclohexyl), 1.94-2.04 (m, 1H, —OCH₂CH(CH₃)₂), 1.96 (t, 1H, acetylene), 2.10 (dd, 2H, —C₆H₁₀CH₂CCH), 3.91, 3.95 (2×d, 4H, —OCH₂CH(CH₃)₂, —C₆H₁₀CH₂O—).

Preparation 9:
Trans[4-(1-Propargyl)cyclohexylmethyl]benzyl carbonate (92)

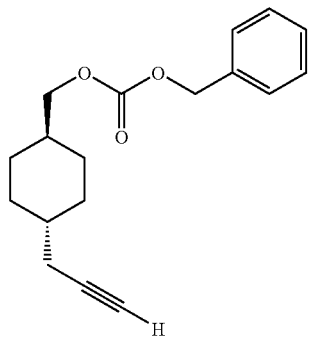

Yield: 340 mg, 69%. ¹H NMR (CDCl₃) δ 0.97-1.08, 1.40-1.49, 1.55-1.69, 1.77-1.93 (4×m, 10H, cyclohexyl), 1.96 (t, 1H, acetylene), 2.10 (dd, 2H, —C₆H₁₀CH₂CCH), 3.98 (d, —C₆H₁₀CH₂O—), 5.15 (s, 2H, —OCH₂Ph), 7.33-7.40 (m, 5H, Ar).

Preparation 10: 4-(Toluene-4-sulfonyloxymethyl)-piperidine-1-carboxylic acid tert-butyl ester (JR3215)

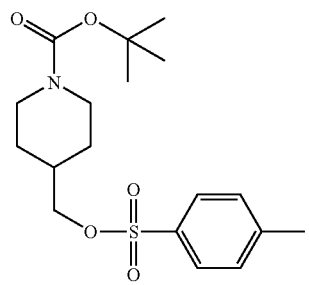

A solution of N-Boc-4-piperidinemethanol, 5.0 g (23.2 mmol) in chloroform, 50 mL, was prepared. Toluene sulfonyl chloride, 5.75 g (30.2 mmol), in 5.6 mL of pyridine (69.6 mmol) was added. The solution was stirred under nitrogen allowed to stir for 24 hours. Standard workup and chromatographic purification provided the title compound. Yield 6.0 g Preparation 11: (R)-1-Ethynyl-(R)-3-methyl-cyclohexanol (JR3217A), (S)-1-Ethynyl-(R)-3-methyl-cyclohexanol (JR3217B)

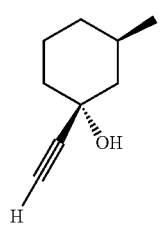

JR3217A

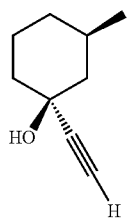

JR3217B

To a solution of 1.0 g (8.9 mmol) (R)-(+)-3-methyl-cyclohexanone in 50 mL of THF was added 54 mL (26.7 mmol) of 0.5 M ethynylmagnesium bromide in THF. The solution was allowed to stir at 20° C. for 20 hours. Analysis by TLC indicated that the starting material had been consumed. The reaction was quenched with 5 mL of water, filtered over a plug of sand and silica, washed with EtOAc, and evaporated to yield 1.15 g of a yellow oil containing two spots (r.f.'s 0.33 (minor, JR3217A) and 0.25 (major, JR3217B), 20% EtOAc/Hexanes) which were visualized with Vanillin. The compound was purified via flash chromatography using 10% EtOAc/Hexanes (225 mL silica) to provide JR3217A and JR3217B.

Preparation 12:
1-Prop-2-ynyl-piperidine-2-carboxylic acid methyl ester (JR3249)

The title compound was prepared starting with 4.0 g (22.3 mmol) of methylpipecolinate hydrochloride according to general method 2.

Preparation 13:
1-Prop-2-ynyl-piperidine-4-carboxylic acid methyl ester (JR3245)

To a solution of methyl isonipecotate 3.5 g (24.4 mmol, 3.30 mL) in 100 mL dichloromethane was added TEA (1.5 eq, 36.6 mmol, 5.1 mL), propargyl bromide (3.0 eq, 73.2 mmol, 6.5 ml), at room temperature for 36 hrs. The reaction was quenched with 35 mL water to yield to provide a clear solution. The solution was extracted with dichloromethane 2×25 mL, dried with Na₂SO₄, and the solvent evaporated to provide a yellow oil. r.f. (40% EtOAc/Hexanes) 0.26 stains faint white with Vanillin, starting material r.f. 0.05 stains yellow with Vanillin. The product appeared pure after extraction.

Preparation 14:
1-Prop-2-ynyl-piperidine-4-carboxylic acid ethyl ester (JR3271)

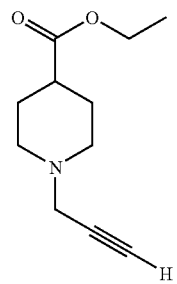

The title compound was prepared starting with 2.0 g (12.7 mmol) of ethyl isonipecotate according to general method 2.

Preparation 15:
4-Prop-2-ynyl-piperazine-1-carboxylic acid tert-butyl ester (JR3275)

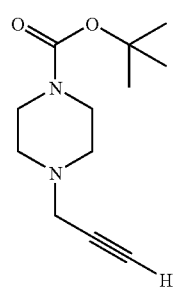

To a solution of 10.0 g (54.8 mmol) of tert-butyl-1-piperazine carboxylate in 60 mL acetonitile was added 5.20 mL (60.4 mmol) propargyl bromide and 37.9 g (274 mmol) anhydrous potassium carbonate. Additional propargyl bromide, 1.5 mL, was added after stirring for 36 hours at room temperature. The residue was evaporated to dryness. Dichloromethane, 50 mL, and water, 50 mL, were added. The reaction mixture was extracted with $CH_2Cl_2$, 4×40 mL, dried over magnesium sulfate, and evaporate to provide a brown oil. The oil was dissolved in dichloromethane and purify with a RT Scientific system using hexane/ethyl acetate gradient to yield 5.5 g (46%) of yellow oil, which ultimately crystallized upon standing.

Preparation 16:
4-Cyanomethyl-piperazine-1-carboxylic acid ethyl ester (JR3287)

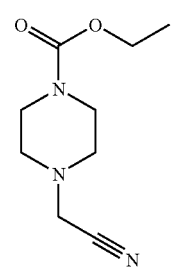

To a solution of 3 g (19.0 mmol) of ethyl N-piperazinecarboxylate in 25 mL of $CH_3CN$ was added 1.57 g (1.32 mL 20.1 mmol) of 2-chloroacetonitrile and 15.6 g (95 mmol) $K_2CO_3.1½H_2O$. The suspension was stirred at room temperature for 16 hours. The reaction was analyzed using TLC (35% Ethyl acetate/Hexanes, product r.f. 0.38 vs. s.m. r.f. of 0.02). The analysis indicated the reaction was complete. The golden yellow solution was evaporated to dryness. The residue was extracted with $CH_2Cl_2/H_2O$, dried with $MgSO_4$, and concentrated.

Preparation 17:
1-Cyclohexyl-4-prop-2-ynyl-piperazine (JR4019)

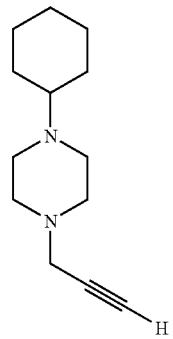

The title compound was prepared starting with 3 g (17.9 mmol) of 1-cyclohexylpiperazine according to general method 2

Preparation 18: 1-Prop-2-ynyl-piperazine (JR4029)

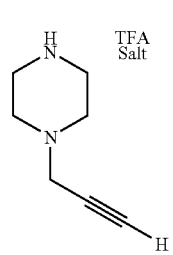

To a flame-dried 25 mL round bottom flask under nitrogen was added 2.1 g of 4-Prop-2-ynyl-piperazine-1-carboxylic acid tert-butyl ester. To this solid was added 5 mL of 98% TFA in 1 mL portions. The solution turned wine red, bubbled and smoked. The additional portions of TFA were added when this activity subsided. After the third portion of TFA had been added only minimal bubbling occurred. The solution was allowed to stir under nitrogen at room temperature for an additional hour and evaporated under reduced pressure to yield the product as a thick red syrup. Assumed quantitative yield of 1.16 g. The residue was suspended in 20 mL dichloromethane and used immediately without further purification for the preparation of compounds JR4031, JR4033, and JR4035.

Preparation 19: 4-Prop-2-ynyl-piperazine-1-carboxylic acid methyl ester (JR4031)

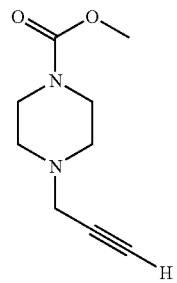

The title compound was prepared starting with 385 mg (3.1 mmol) of JR4029 and using methylchloroformate according to general method 3.

Preparation 20: 4-Prop-2-ynyl-piperazine-1-carboxylic acid isobutyl ester (JR4035)

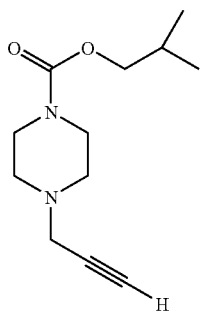

The title compound was prepared starting with 385 mg (3.1 mmol) of JR4029 and using isobutylchloroformate according to general method 3.

Preparation 21: 3,3-Dimethyl-1-(4-prop-2-ynyl-piperidin-1-yl)-butan-1-one (JR4041)

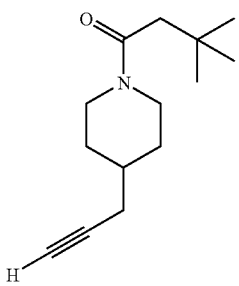

The title compound was prepared starting with tert-butyl ester (JR3257) and using tert-butylacetylchloride according to general method 3.

Preparation 22: 1-(4-Prop-2-ynyl-piperazin-1-yl)-ethanone (JR4043)

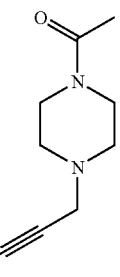

The title compound was prepared starting with 385 mg (3.1 mmol) of JR4029 and using acetyl chloride according to general method 3.

The following intermediate compounds are prepared using the general method 1 described herein and the appropriate starting materials.

(R)-1-Ethynyl-3-tert-butyl-cyclohexanol (JR3255A), (S)-1-Ethynyl-3-tert-butyl-cyclohexanol (JR3255B)

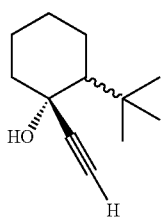

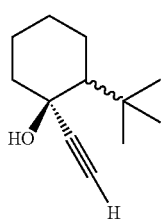

Toluene-4-sulfonic acid 4-prop-2-ynyl-cyclohexylmethyl ester (JR3077)

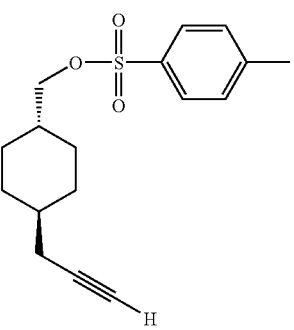

65
1-Ethyl-4-prop-2-ynyl-cyclohexane (JR3083)
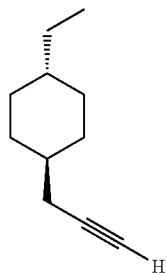
1-(4-Prop-2-ynyl-cyclohexyl)-ethanone (JR3115)
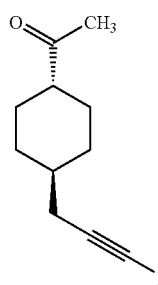
1,1-Dicyclohexyl-prop-2-yn-1-ol (JR3127)
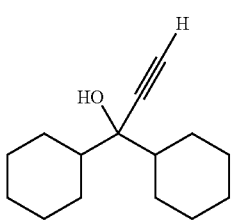
1-Cyclohexyl-prop-2-yn-1-ol (JR3129)
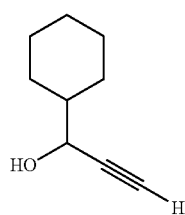
66
4-Ethyl-1-ethynyl-cyclohexanol (JR3143)
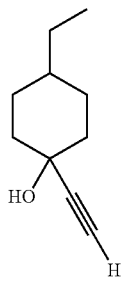
1-Ethynyl-3-methyl-cyclohexanol
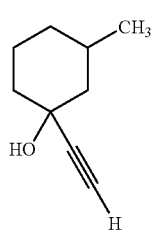
1-Ethynyl-3,3,5,5-tetramethyl-cyclohexanol (JR3151)
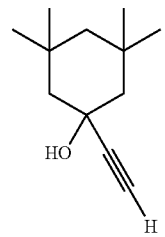
1-Ethynyl-4-phenyl-cyclohexanol (JR3153)
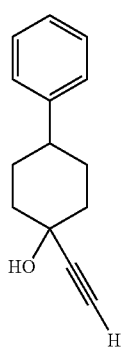

67

1-Ethynyl-2-methyl-cyclohexanol (JR3167B)

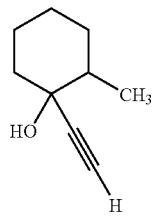

1-Ethynyl-2-methyl-cyclohexanol (JR3167B)

4-tert-Butyl-1-ethynyl-cyclohexanol (JR3191)

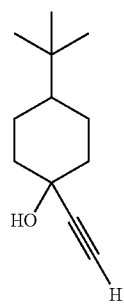

JR3191

1-Ethynyl-3,3-dimethyl-cyclohexanol (JR3193)

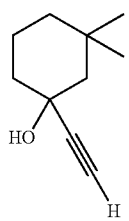

JR3193

4-Hydroxymethyl-piperidine-1-carboxylic acid tert-butyl ester (JR3199)

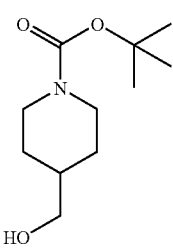

JR3199

68

4-Prop-2-ynyl-piperazine-1-carboxylic acid ethyl ester (JR3211)

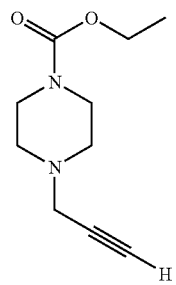

JR3211

4-Prop-2-ynyl-piperidine-1-carboxylic acid tert-butyl ester (JR3257)

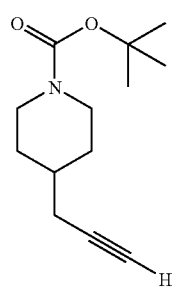

JR3257

4-Prop-2-ynyl-piperidine-1-carboxylic acid ethyl ester (JR3267B)

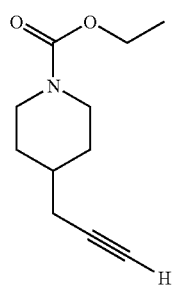

JR3267B 2-(4-Prop-2-ynyl-piperazin-1-yl)-pyrimidine (JR3277)

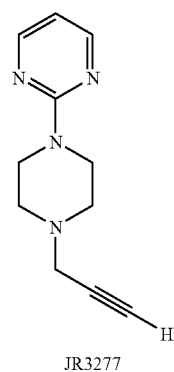

JR3277

1-(4-Prop-2-ynyl-piperidin-1-yl)-ethanone (JR4037)

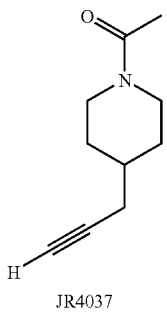

JR4037

2,2-Dimethyl-1-(4-prop-2-ynyl-piperidin-1-yl)-propan-1-one (JR4039)

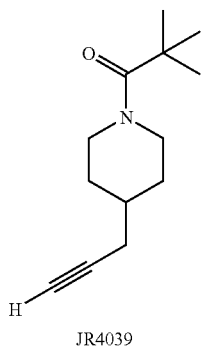

JR4039

Example 1

4-{3-[6-Amino-9-(5-cyclopropylcarbamoyl-3,4-dihydroxy-tetrahydro-furan-2-yl)-9H-purin-2-yl]-prop-2-ynyl}-cyclohexanecarboxylic acid methyl ester

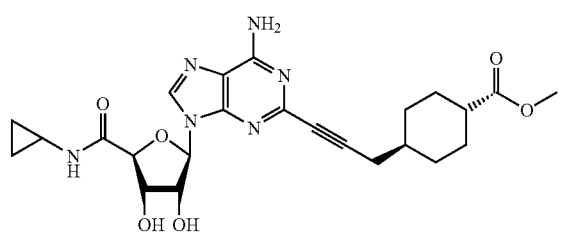

MS: m/z 499.3 (M+H)+.

Example 2

4-{3-[6-Amino-9-(5-cyclopropylcarbamoyl-3,4-dihydroxy-tetrahydro-furan-2-yl)-9H-purin-2-yl]-prop-2-ynyl}-piperidine-1-carboxylic acid methyl ester

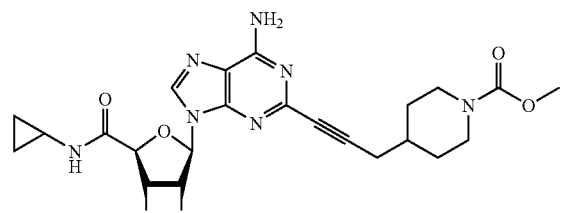

MS: m/z 500.4 (M + H)+.

Example 3

5-[6-Amino-2-(1-hydroxy-3-methyl-cyclohexylethynyl)-purin-9-yl]-3,4-dihydroxy-tetrahydro-furan-2-carboxylic acid cyclopropylamide

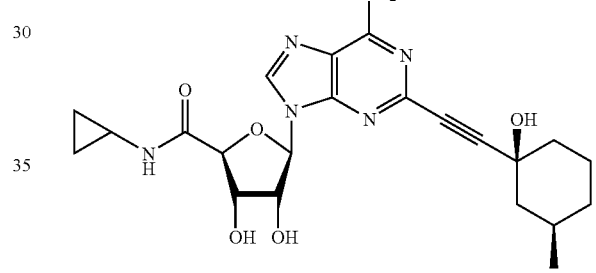

MS: m/z 457.4 (M + H)+.

Example 4

5-(6-Amino-2-iodo-purin-9-yl)-3,4-dihydroxy-tetrahydro-furan-2-carboxylic acid cyclopropylamide

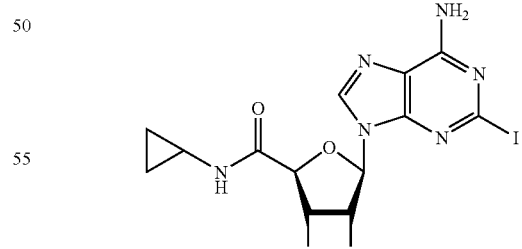

Example 5

Cell Culture and Membrane Preparation

Sf9 cells were cultured in Grace's medium supplemented with 10% fetal bovine serum, 2.5 µg/ml amphotericin B and 50 µg/ml gentamycin in an atmosphere of 50% $N_2$/50% $O_2$. Viral infection was performed at a density of $2.5 \times 10^6$ cells/mL with a multiplicity of infection of two for each virus used. Infected cells were harvested 3 days post-infection and washed twice in insect PBS (PBS pH 6.3). Cells were then resuspended in lysis buffer (20 mM HEPES pH 7.5, 150 mM NaCl, 3 mM $MgCl_2$, 1 mM β-mercaptoethanol (BME), 5 µg/mL leupeptin, 5 µg/mL pepstatin A, 1 µg/mL aprotinin, and 0.1 mM PMSF) and snap frozen for storage at −80° C. Cells were thawed on ice, brought to 30 mL total volume in lysis buffer, and burst by $N_2$ cavitation (600 psi for 20 minutes). A low-speed centrifugation was performed to remove any unlysed cells (1000×g for 10 minutes), followed by a high-speed centrifugation (17,000×g for 30 minutes). The pellet from the final centrifugation was homogenized in buffer containing 20 mM HEPES pH 8, 100mM NaCl, 1% glycerol, 2 µg/mL leupeptin, 2 µg/mL pepstatin A, 2 µg/mL Aprotinin, 0.1 mM PMSF, and 10 µM GDP using a small glass homogenizer followed by passage through a 26 gauge needle. Membranes were aliquoted, snap frozen in liquid $N_2$, and stored at −80° C. Membranes from cells stably expressing the human $A_1$ AR(CHO K1 cells) or $A_3$ AR(HEK 293 cells) were prepared as described (Robeva et al., 1996).

Example 6

Radioligand Binding Assays

Radioligand binding to recombinant human $A_{2A}$ receptors in Sf9 cell membranes was performed using either the radio labeled agonist, $^{125}$I-APE (Luthin et al., 1995) or the radio labeled antagonist, $^{125}$I-ZM241385 ($^{125}$I-ZM). To detect the high affinity, GTPγS-sensitive state of $A_1$ and $A_3$AR, we used the agonist, $^{125}$I-ABA (Linden et al., 1985; Linden et al., 1993). Binding experiments were performed in triplicate with 5 µg ($A_{2A}$) or 25 µg ($A_1$ and $A_3$) membrane protein in a total volume of 0.1 mL HE buffer (20 mM HEPES and 1 mM EDTA) with 1 U/mL adenosine deaminase and 5 mM $MgCl_2$ with or without 50 µM GTPγS. Membranes were incubated with radioligands at room temperature for three hours (for agonists) or two hours (for antagonists) in Millipore Multiscreen® 96-well GF/C filter plates and assays were terminated by rapid filtration on a cell harvester (Brandel, Gaithersburg, Md.) followed by 4×150 µl washes over 30 seconds with ice cold 10 mM Tris-HCl, pH 7.4, 10 mM $MgCl_2$. Non-specific binding was measured in the presence of 50 µM NECA. Competition binding assays were performed as described (Robeva et al., 1996) using 0.5-1 nM $^{125}$I-APE, $^{125}$I-ZM241385, or $^{125}$I-ABA. We found that it was sometimes important to change pipette tips following each serial dilution to prevent transfer on tips of potent hydrophobic compounds. The Ki values for competing compound binding to a single site were derived from $IC_{50}$ values with correction for radioligand and competing compound depletion as described previously (Linden, 1982).

Linden J (1982) Calculating the Dissociation Constant of an Unlabeled Compound From the Concentration Required to Displace Radiolabel Binding by 50%. J Cycl Nucl Res 8: 163-172.

Linden J, Patel A and Sadek S (1985) [$^{125}$I]Aminobenzyladenosine, a New Radioligand With Improved Specific Binding to Adenosine Receptors in Heart. Circ Res 56: 279-284.

Linden J, Taylor H E, Robeva A S, Tucker A L, Stehle J H, Rivkees S A, Fink J S and Reppert S M (1993) Molecular Cloning and Functional Expression of a Sheep $A_3$ Adenosine Receptor With Widespread Tissue Distribution. Mol Pharmacol 44: 524-532.

Luthin D R, Olsson R A, Thompson R D, Sawmiller D R and Linden J (1995) Characterization of Two Affinity States of Adenosine $A_{2A}$ Receptors With a New Radioligand, 2-[2-(4-Amino-3-[$^{125}$I]Iodophenyl)Ethylamino]Adenosine. Mol Pharmacol 47: 307-313.

Robeva A S, Woodard R, Luthin D R, Taylor H E and Linden J (1996) Double Tagging Recombinant $A_1$- and $A_{2A}$-Adenosine Receptors With Hexahistidine and the FLAG Epitope. Development of an Efficient Generic Protein Purification Procedure. Biochem Pharmacol 51: 545-555.

Chemiluminescence Methods: Luminol enhanced chemiluminescence, a measure of neutrophil oxidative activity, is dependent upon both superoxide production and mobilization of the granule enzyme myeloperoxidase. The light is emitted from unstable high-energy oxygen species such as hypochlorous acid and singlet oxygen generated by activated neutrophils.

Purified human neutrophils (2×106/ml) suspended in Hanks balanced salt solution containing 0.1% human serum albumin (HA), adenosine deaminase (1 U/mL) and rolipram (100 nM) were incubated (37° C.) in a water bath for 15 min with or without rhTNF(10 U/ml). Following incubation 100 L aliquots of the PMN were transferred to wells (White walled clear bottom 96 well tissue culture plates Costar #3670; 2 wells/condition) containing 501 HA and luminol (final concentration 100 M) with or without adenosine agonist (final agonist concentrations 0.01-1000 nM). The plate was incubated 5 min (37° C.) and then fMLP (501 in HA; final concentration IM) was added to all wells.

Peak chemiluminescence was determined with a Victor 1420 Multilabel Counter in the chemiluminescence mode using the Wallace Workstation software. Data are presented as peak chemiluminescence as percent of activity in the absence of an adenosine agonist. The $EC_{50}$ was determined using PRISM software. All compounds were tested with PMNs from three separate donors. The results are summarized in Table 5.

TABLE 5

Binding Affinity And Selectivity For $A_{2A}$ Agonists

| Compound | $A_1$ (nM) | $A_{2A}$ (nM) | $A_3$ (nM) | Functional (nM)[1] | Functional + Roli (nM)[2] |
|---|---|---|---|---|---|
| Example 1 | 32 | .58 | 34 | 2.0 | 0.20 |
| Example 2 | 57 | .7 | 247 | 2.0 | 0.20 |
| Example 3 | 1.5 | .5 | 3 | 0.3 | 0.04 |
| Example 4 | 33 | 0.6 | 45 | 2.0 | 0.20 |

[1] Human neutrophil experiment as described in Example 7 without Rolipram.
[2] Human neutrophil experiment as described in Example 7 with Rolipram.

Example 7

Effect of $A_{2A}$ Agonists on Neutrophil Oxidative Activity

A. Materials.

f-met-leu-phe (fMLP), luminol, superoxide dismutase, cytochrome C, fibrinogen, adenosine deaminase, and trypan blue were obtained from Sigma Chemical. Ficoll-hypaque was purchased from ICN (Aurora, Ohio), and Cardinal Scientific (Santa Fe, N. Mex.) and Accurate Chemicals and Scientific (Westerbury, N.Y.). Endotoxin (lipopolysaccharide; *E. coli* K235) was from List Biologicals (Campbell, Calif.). Hanks balanced salt solution (HBSS), and *limulus amebocyte* lysate assay kit were from BioWittaker (Walkersville, Md.). Human serum albumin (HSA) was from Cutter Biological (Elkhart, Ind.). Recombinant human tumor necrosis factor-alpha was supplied by Dianippon Pharmaceutical Co. Ltd. (Osaka, Japan). ZM241385 (4-(2-[7-amino-2-(2-furyl) [1,2,4]triazolo[2,3-a][1,3,5]triazin-5-yl amino]ethyl)phenol) was a gift from Simon Poucher, Zeneca Pharmaceuticals, Cheshire, UK. Stock solutions (1 mM and 10 mM in DMSO) were made and stored at −20° C.

B. Human Neutrophil Preparation

Purified neutrophils (~98% neutrophils and >95% viable by trypan blue exclusion) containing <1 platelet per 5 neutrophils and <50 pg/ml endotoxin (*limulus* amebocyte lysate assay) were obtained from normal heparinized (10 U/ml) venous blood by a one step Ficoll-hypaque separation procedure (A. Ferrante et al., *J. Immunol. Meth.*, 36, 109 (1980)).

C. Release of Inflammatory Reactive Oxygen Species from Primed and Stimulated Human Neutrophils Chemiluminescence Luminol-enhanced chemiluminescence, a measure of neutrophil oxidative activity, is dependent upon both superoxide production and mobilization of the lysosomal granule enzyme myeloperoxidase. The light is emitted from unstable high-energy oxygen species generated by activated neutrophils. Purified neutrophils ($5-10\times10^5$/ml) were incubated in Hanks balanced salt solution containing 0.1% human serum albumin (1 ml) with the tested $A_{2A}$ agonist with or without rolipram and with or without tumor necrosis factor-alpha (1 U/ml) for 30 minutes at 37° C. in a shaking water bath. Then luminol ($1\times10^{-4}$ M) enhanced f-met-leu-phe (1 mcM) stimulated chemiluminescence was read with a Chronologo Photometer (Crono-log Corp., Havertown, Pa.) at 37° C. for 2-4 minutes. Chemiluminescence is reported as relative peak light emitted (=height of the curve) compared to samples with tumor necrosis factor-alpha and without agonist or rolipram.

Example 8

In Vivo Rat Blood Pressure Experiments

Sprague-Dawley rats (mean weights, 250-300 grams) were anthesthetized and jugular and carotid catheters are implanted ipsilaterally and the animals are allowed to recover 24-48 hours. Prior to each experiment a baseline blood pressure reading is established for 30 minutes with each drug injection being preceded by a vehicle control. Drugs are injected bolus I.V. through a jugular catheter in a 200 microliter volume of saline and the catheter is flushed with an additional 300 microliters of saline. To measure blood pressure, a central line from the carotid catheter is attached to the pressure transducer of a Digi-Med Blood Pressure Analyzer. Systolic pressure, diastolic pressure, mean pressure, and heart rate are all recorded in real time at 30-60 second intervals. Data is recorded until mean blood pressure has returned to baseline and remained constant for 20 minutes. The data is presented as a fraction of the mean blood pressure averaged over the 10 minutes immediately prior to drug injection. The blood pressures are recorded and plotted over time as a means of determining potency of the compounds as well as biological half-life.

The compounds of examples 1 and 2 were tested against a control compound, illustrated below:

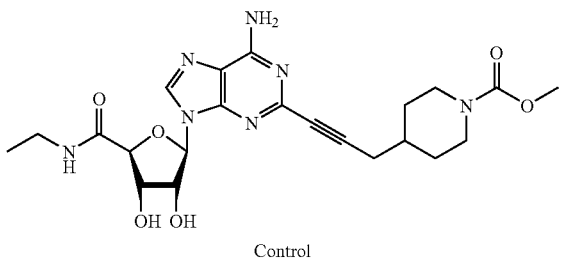

Control

Figure 2:
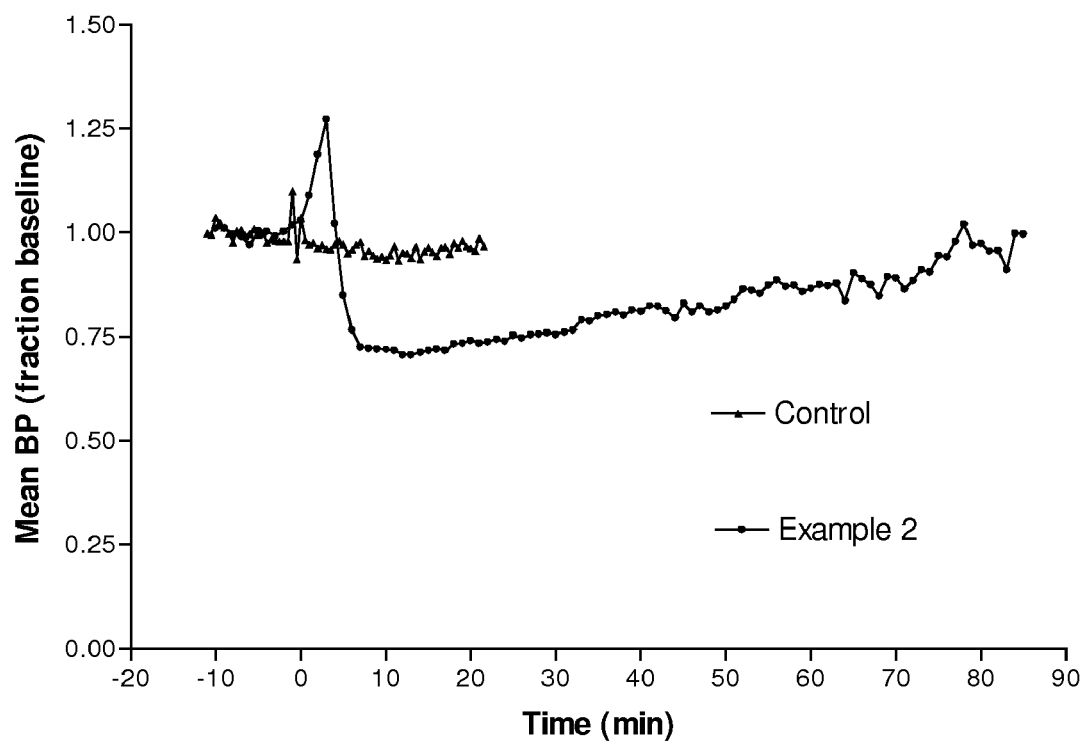
FIG. 2 is an illustration of the duration of action of $A_{2A}$ agonists by monitoring the reduction of blood pressure in rats after administration of compounds of the present invention orally compared with other $A_{2A}$ agonists.

The results are illustrated in FIGS. 1-2.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A composition comprising a compound of formula

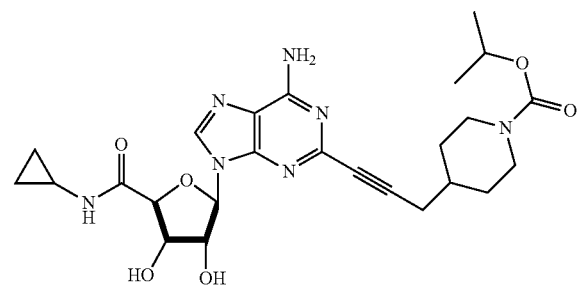

or a pharmaceutically acceptable salt thereof and a pharmaceutically acceptable diluent or carrier.

2. A composition a compound of the formula

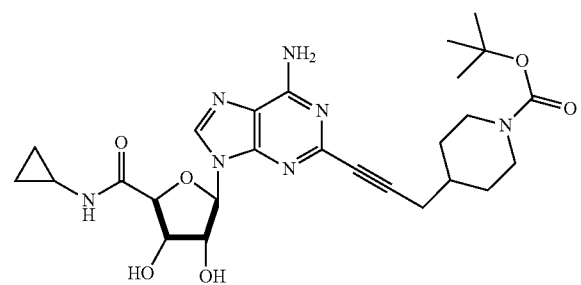

or a pharmaceutically acceptable salt thereof and a pharmaceutically acceptable diluent or carrier.

3. A composition comprising a compound of formula

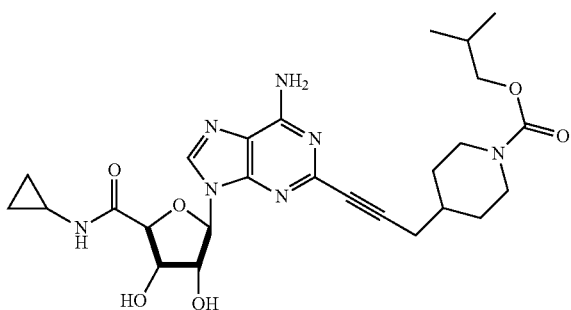

or a pharmaceutically acceptable salt thereof and a pharmaceutically acceptable diluent or carrier.

4. A composition comprising a compound of formula

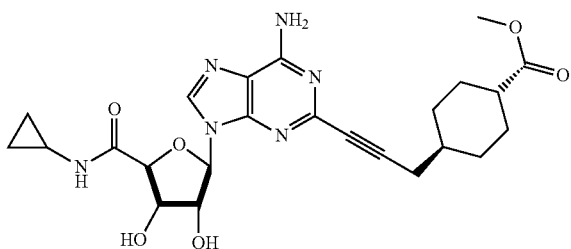

or a pharmaceutically acceptable salt thereof and a pharmaceutically acceptable diluent or carrier.

5. A composition comprising a compound of formula

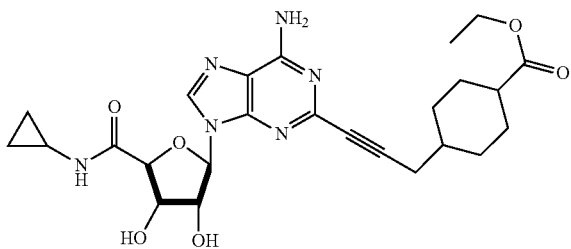

or a stereoisomer or a pharmaceutically acceptable salt thereof and a pharmaceutically acceptable diluent or carrier.

6. A composition comprising a compound of formula

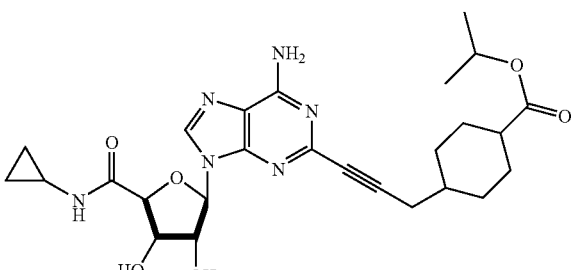

or a stereoisomer or a pharmaceutically acceptable salt thereof and a pharmaceutically acceptable diluent or carrier.

7. A composition comprising a compound of formula

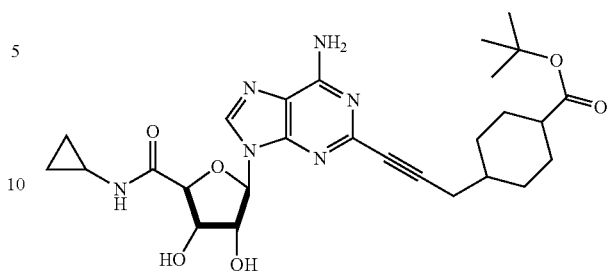

or a stereoisomer or a pharmaceutically acceptable salt thereof and a pharmaceutically acceptable diluent or carrier.

8. A composition comprising a compound of formula

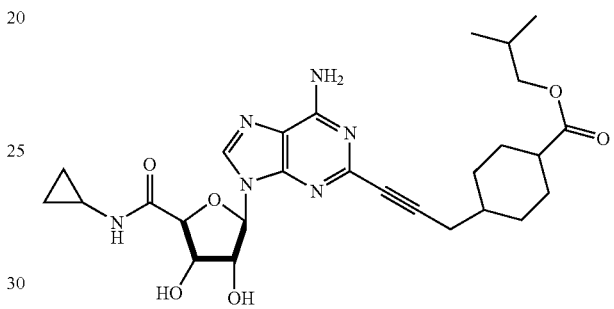

or a stereoisomer or a pharmaceutically acceptable salt thereof and a pharmaceutically acceptable diluent or carrier.

9. A composition comprising a compound of formula

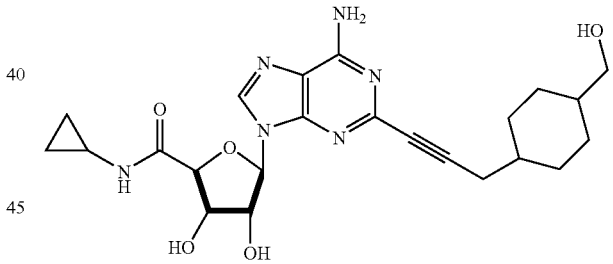

or a stereoisomer or a pharmaceutically acceptable salt thereof and a pharmaceutically acceptable diluent or carrier.

10. A composition comprising a compound of formula

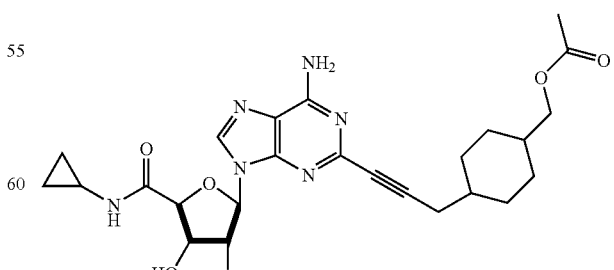

or a stereoisomer or a pharmaceutically acceptable salt thereof and a pharmaceutically acceptable diluent or carrier.

11. A composition comprising a compound of formula

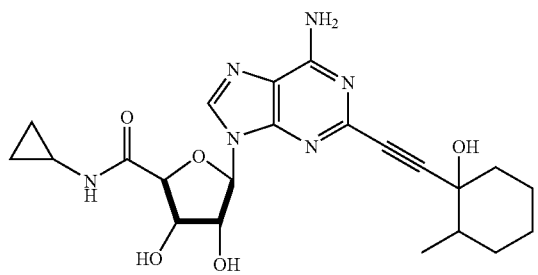

or a stereoisomer or a pharmaceutically acceptable salt thereof and a pharmaceutically acceptable diluent or carrier.

12. A composition comprising a compound of formula

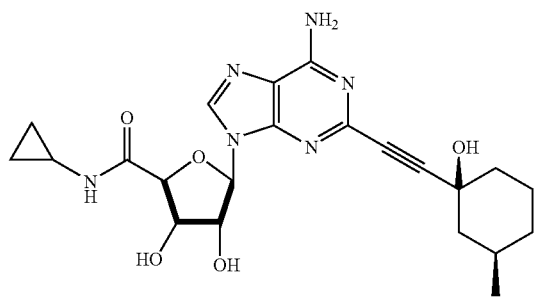

or a pharmaceutically acceptable salt thereof and a pharmaceutically acceptable diluent or carrier.

13. A composition comprising a compound of formula

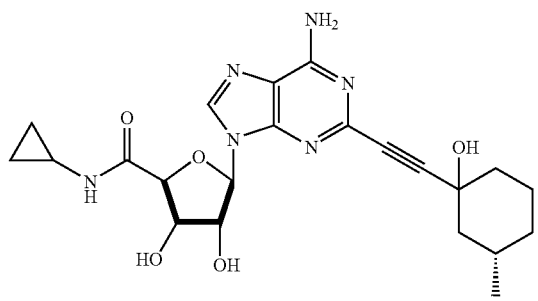

or a stereoisomer or a pharmaceutically acceptable salt thereof and a pharmaceutically acceptable diluent or carrier.

14. A composition comprising a compound of formula

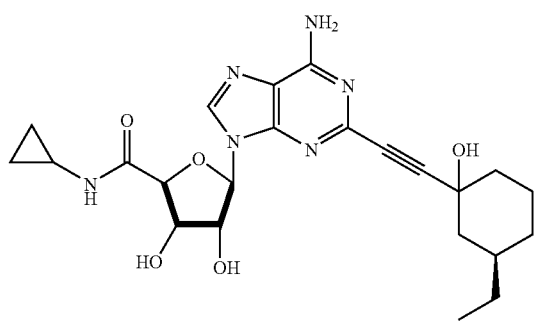

or a stereoisomer or a pharmaceutically acceptable salt thereof and a pharmaceutically acceptable diluent or carrier.

15. A composition comprising a compound of formula

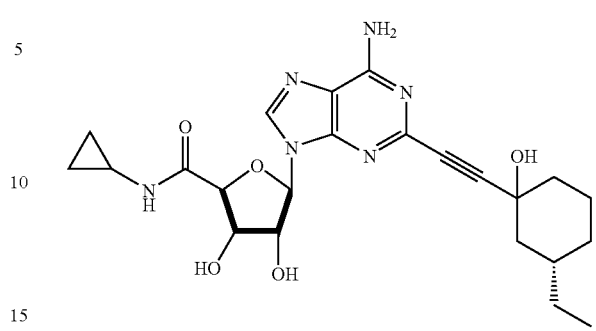

or a stereoisomer or a pharmaceutically acceptable salt thereof and a pharmaceutically acceptable diluent or carrier.

16. A composition comprising a compound of formula

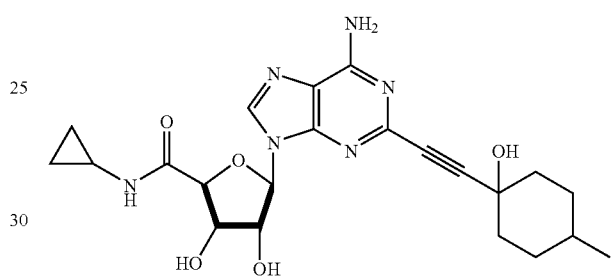

or a stereoisomer or a pharmaceutically acceptable salt thereof and a pharmaceutically acceptable diluent or carrier.

17. A composition comprising a compound of formula

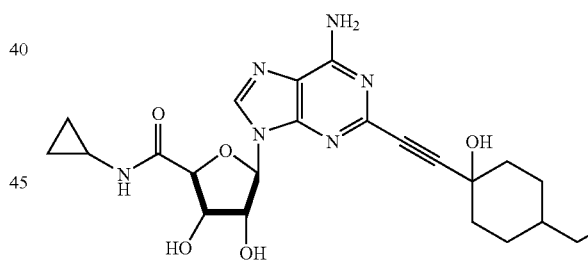

or a stereoisomer or a pharmaceutically acceptable salt thereof and a pharmaceutically acceptable diluent or carrier.

18. A composition comprising a compound of formula

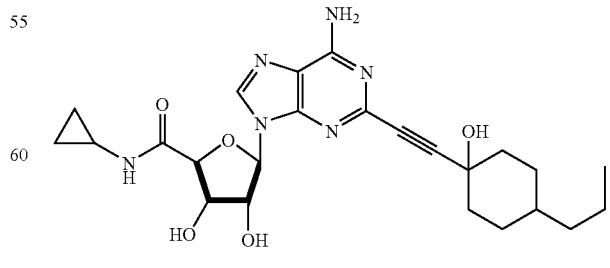

or a stereoisomer or a pharmaceutically acceptable salt thereof and a pharmaceutically acceptable diluent or carrier.

19. A composition comprising a compound of formula
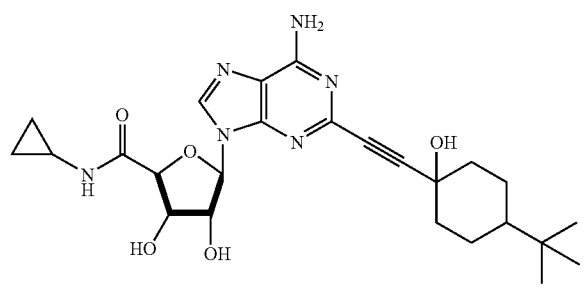
or a stereoisomer or a pharmaceutically acceptable salt thereof and a pharmaceutically acceptable diluent or carrier.
20. A composition comprising a compound of formula
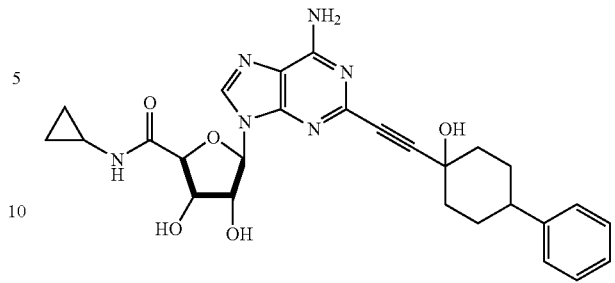
or a stereoisomer or a pharmaceutically acceptable salt thereof and a pharmaceutically acceptable diluent or carrier.
* * * * *

UNITED STATES PATENT AND TRADEMARK OFFICE
CERTIFICATE OF CORRECTION

PATENT NO. : 7,989,431 B2  Page 1 of 1
APPLICATION NO. : 12/487235
DATED : August 2, 2011
INVENTOR(S) : Jayson M. Rieger et al.

It is certified that error appears in the above-identified patent and that said Letters Patent is hereby corrected as shown below:

In column 74, line 51, in Claim 2, delete "A composition a compound of" and insert
-- A composition comprising a compound of --, therefor.

Signed and Sealed this
Third Day of January, 2012

David J. Kappos
*Director of the United States Patent and Trademark Office*